(12) United States Patent
Hardy et al.

(10) Patent No.: US 8,227,413 B2
(45) Date of Patent: Jul. 24, 2012

(54) COMPOSITIONS AND METHODS FOR INDUCING ANGIOGENESIS

(75) Inventors: Britta Hardy, Tel-Aviv (IL); Alexander Battler, Ramat-HaSharon (IL); Annat Raiter, Kfar-Saba (IL); Chana Weiss, Givat Shmuel (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 426 days.

(21) Appl. No.: 12/311,866

(22) PCT Filed: Oct. 18, 2007

(86) PCT No.: PCT/IL2007/001256
§ 371 (c)(1),
(2), (4) Date: Apr. 16, 2009

(87) PCT Pub. No.: WO2008/047370
PCT Pub. Date: Apr. 24, 2008

(65) Prior Publication Data
US 2010/0322856 A1   Dec. 23, 2010

Related U.S. Application Data

(60) Provisional application No. 60/852,645, filed on Oct. 19, 2006, provisional application No. 60/897,498, filed on Jan. 26, 2007.

(51) Int. Cl.
*A61K 38/00* (2006.01)
*A61K 38/04* (2006.01)
*C07K 14/515* (2006.01)
*C07K 5/00* (2006.01)
*C07K 7/00* (2006.01)
*C07K 16/00* (2006.01)
*C07K 17/00* (2006.01)
*A61P 35/00* (2006.01)

(52) U.S. Cl. ....... 514/13.3; 530/327; 530/328; 530/329; 530/330

(58) Field of Classification Search .................. None
See application file for complete search history.

(56) References Cited

U.S. PATENT DOCUMENTS

| | | |
|---|---|---|
| 6,638,911 B1 | 10/2003 | Blaschuk et al. |
| 7,473,682 B2 | 1/2009 | Hardy et al. |
| 2005/0112168 A1 | 5/2005 | Puzas |
| 2007/0082849 A1 | 4/2007 | Hardy et al. |
| 2007/0166350 A1 | 7/2007 | Hamilton et al. |
| 2009/0163405 A1 | 6/2009 | Hardy et al. |
| 2010/0322856 A1 | 12/2010 | Hardy et al. |

FOREIGN PATENT DOCUMENTS

| | | |
|---|---|---|
| EP | 1136082 | 9/2001 |
| FR | 2814744 | 4/2002 |
| WO | WO 97/07202 | 2/1997 |
| WO | WO 00/32631 | 6/2000 |
| WO | WO 02/02593 | 1/2002 |
| WO | WO 02/057299 | 7/2002 |
| WO | WO 03/014329 | 2/2003 |
| WO | WO 03/037172 | 5/2003 |
| WO | WO 03/065881 | 8/2003 |
| WO | WO 03/072593 | 9/2003 |
| WO | WO 2005/039616 | 5/2005 |
| WO | WO 2006/039173 | 4/2006 |
| WO | WO 2007/149529 | 12/2007 |
| WO | WO 2008/047370 | 2/2008 |
| WO | WO 2008/047370 | 4/2008 |
| WO | WO 2010/052715 | 5/2010 |

OTHER PUBLICATIONS

Sporn et al. Chemoprevention of cancer. Carcinogenesis. 2000. vol. 21, Nol. 3, pp. 525-530.*
Voskoglou-Nomikos et al. Clinical Predictive Value of the in Vitro Cell Line, Human Xenograft and Mouse Allograft Preclinical Cancer Models. Clinical Cancer Research, 2003. vol. 9, pp. 4227-4239.*
Zips et al. New Anticancer Agents: In Vitro and In Vivo Evaluation. Review. in vivo, 2005, vol. 19, pp. 1-8.*
Communication Pursuant to Article 94(3) EPC Dated May 18, 2009 From the European Patent Office Re.: Application No. 04791852.9.
International Preliminary Report on Patentability Dated May 11, 2006 From the International Bureau of WIPO Re.: Application No. PCT/IL2004/000992.
International Preliminary Report on Patentability Dated Apr. 30, 2009 From the International Bureau of WIPO Re.: Application No. PCT/IL2007/001256.
International Search Report Dated Mar. 28, 2008 From the International Searching Authority Re.: Application No. PCT/IL2007/001256.
Notice of Allowance Dated Aug. 25, 2008 From the US Patent and Trademark Office Re.: U.S. Appl. No. 10/577,679.
Office Action Dated Mar. 10, 2009 From the Israeli Patent Office Re.: Application No. 175197 and Its Translation Into English.
Official Action Dated Jul. 12, 2007 From the US Patent and Trademark Office Re.: U.S. Appl. No. 10/577,679.
Official Action Dated Jan. 22, 2008 From the US Patent and Trademark Office Re.: U.S. Appl. No. 10/577,679.
Official Action Dated Mar. 29, 2007 From the US Patent and Trademark Office Re.: U.S. Appl. No. 10/577,679.
Written Opinion Dated Mar. 28, 2008 From the International Searching Authority Re.: Application No. PCT/IL2007/001256.
Bainbridge et al. "A Peptide Encoded by Exon 6 of VEGF (EG3306) Inhibits VEGF-IncludedAngiogenesis In Vitro and Ischaemic Retinal Neovascularisation In Vivo", Biochemical and Biophysical Research Communications, 302: 793-799, 2003.
Binétruy-Tournaire et al. "Identification of a Peptide Blocking Vascular Endothelial Growth Factor (VEGF)-Mediated Angiogenesis", The EMBO Journal, 19(7): 1525-1533, 2000.
Bruneel et al. "Proteomics of Human Umbilical Vein Endothelial Cells Applied to Etoposide-Induced Apoptosis", Proteomics, 5(15): 3876-3884, 2005. Abstract.

(Continued)

Primary Examiner — Marcela M Cordero Garcia

(57) ABSTRACT

An isolated peptide comprising an amino acid sequence HWRR as set forth by SEQ ID NO:5, the peptide consists of 4 or 5 amino acids, is provided. Also provided are methods of treating angiogenesis-related pathologies using the peptide of the invention or pharmaceutical compositions comprising same.

24 Claims, 36 Drawing Sheets
(35 of 36 Drawing Sheet(s) Filed in Color)

OTHER PUBLICATIONS

Conway et al. "Molecular Mechanisms of Blood Vessel Growth", Cardiovascular Research, 49: 507-521, 2001.
Davidson et al. "Kringle 5 of Human Plasminogen Induces Apoptosis of Endothelial and Tumor Cells Through Surface-Expressed Glucose-Regulated Protein 78", Cancer Research, 65(11): 4663-4672, 2005.
Dong et al. "Vascular Targeting and Antiangiogenesis Agents Induce Drug Resistance Effector GRP78 Within the Tumor Microenvironment", Cancer Research, 65(13): 5785-5791, 2005.
George et al "Circulating Endothelial Progenitor Cells in Patients With Unstable Angina: Association With Systemic Inflammation", European Heart Journal, 25: 1003-1008, 2004.
George et al "Circulating Endothelial Progenitor Cells in Patients with Unstable Angina: Association With Systemic Inflammation",European Heart Journal 25:1003-1008 (2004).
Giordano et al. "Biopanning and Rapid Analysis of Selective Interactive Ligands", Nature Medicine, 11(7): 1249-1253, 2001.
Hardy et al. "Angiogenesis Induced by Novel Peptides Selected From a Phage Display Library by Screening Human Vascular Endothelial Cells Under Different Physiological Conditions", Peptides, 28(3): 691-701, 2007.
Hardy et al. "Therapeutic Angiogenesis of Mouse Hind Limb Ischemia by Novel Peptide Activationg GRP78 Receptor on Endothelial Cells", Biochemical Pharmacology, 75(4): 891-899, 2008.
Hetian et al. "A Novel Peptide Isolated From a Phage Display Library Inhibits Tumor Growth and Metastasis by Blocking the Binding of Vascular Endothelial Growth Factor to Its Kinase Domain Receptor", The Journal of Biological Chemistry, 277(45): 43137-43142, 2002.
Khurana et al "Endothelial Activation and Neointimal Hyperplasia: A Double-Edged Sword", E. Deindl and C. Kupatt (eds.), Therapeutic Neovascularization—Quo Vadis?, 75-84.
Khurana et al "Endothelial Activation and Neointimal Hyperplasia: A Double-Edged Sword", Therapeutic Neovascularization—Qua Vadis?, Chap.4: 75-84, 2007.
Koomägi et al. "Glucose-Related Protein (GRP78) and Its Relationship to the Drug-Resistance Proteins P170, GST-Pi, LRP56 and Angiogenesis in Non-Small Cell Lung Carcinomas", Anticancer Research, 19(5B): 4333-4336, 1999. Abstract.
Koshikawa et al. "Hypoxia Selects for High-Metastatic Lewis Lung Carcinoma Cells Overexpressing Mel-1 and Exhibiting Reduced Apoptotic Potential in Solid Tumors", Oncogene, 25(6): 917-928, 2006. Abstract.
Liu et al. "Combinatorial Peptide Library Methods for Immunobiology Research", Experimental Hematology, 31: 11-30, 2003.
Mahler et al. "A Population of Autoantibodies Against a Centromere-Associated Protein A Major Epitope Motif Cross-Reacts With Related Cryptic Epitopes on Other Nuclear Autoantigens and on the Epstein-Barr Nuclear Antigen 1", Journal of Molecular Medicine, 79: 722-731, 2001. Table 2.
Puzas "Human TRAP Peptide SEQ ID No. 24", Database Geneseq 'Online!, Database Accession No. ABR44764, 2003. Abstract.
Ramarao "Human Sperm Activator Peptide (Husap), Sperm 5 Pro.", Database Geneseq 'Online!, Database Accession No. AAE32981, 2003. Abstract.
Trochon et al. "Endothelial Metalloprototease-Disintegrin Protein (ADAM) Is Implicated in Angiogenesis In Vitro", Angiogenesis, 2(3): 277-285, 1998. Abstract.
Zhang et al. "Neuroblastoma Tumor Cell-Binding Peptides Identified Through Random Peptide Phage Display", Cancer Letters, 171: 153-164, 2001.
Communication Pursuant to Article 94(3) EPC Dated Jan. 19, 2011 From the European Patent Office Re. Application No. 07827230.9.
Additional Response Dated Sep. 20, 2010 to Examination Report of Feb. 15, 2010 From the Government of India, Patent Office Re.: Application No. 1885/CHENP/2006.
Response Dated Sep. 15, 2010 to Examination Report of Feb. 15, 2010 From the Government of India, Patent Office Re.: Application No. 1885/CHENP/2006.
Official Action Dated May 5, 2011 From the US Patent and Trademark Office Re.: U.S. Appl. No. 12/292,876.
International Search Report and the Written Opinion Dated Feb. 10, 2011 From the International Searching Authority Re. Application No. PCT/IL2009/001046.
Khurana et al "Endothelial Activialion and Neointimal Hyperplasia: A Double-Edged Sword", E. Deindl and C. Kupatt (eds.), Therapeutic Neovascularization—Quo Vadis?, 75-84.
Shirota et al. "Fabrication of Endothelial Progenitor Cell (EPC)-Seeded Intravascular Stent Devices and In Vitro Endothelialization on Hybrid Vascular Tissue", Biomaterials, XP004420020, 24(13): 2295-2302, Jun. 1, 2003.
Translation of Notice of Reason for Rejection Dated Jun. 4, 2010 From the Japanese Patent Office Re. Application No. 2006-537555.
Koivunen et al. "Selection of Peptides Binding to the α5β1 Integrin From Phage Display Library", The Journal of Biological Chemistry, 268(27): 20205-20210, Sep. 25, 1993.
Koshikawa et al. "Hypoxia Selects for High-Metastatic Lewis Lung Carcinoma Cells Overexpressing Mc1-1 and Exhibiting Reduced Apoptotic Potential in Solid Tumors", Oncogene, 25(6): 917-928, 2006. Abstract.
Examination Report Dated Nov. 22, 2010 From the Government of India, Patent Office Re.: Application No. 1885/CHENP/2006.
Response Dated Jan. 19, 2011 to Examination Report of Nov. 22, 2010 From the Government of India, Patent Office Re.: Application No. 1885/CHENP/2006.
Hardy et al. "Therapeutic Angiogenesis of Mouse Hind Limb Ischemia by Novel Peptide Activating GRP78 Receptor on Endothelial Cells", Biochemical Pharmacology, 75: 891-899, 2008.
Official Action Dated Jun. 29, 2011 From the US Patent and Trademark Office Re.: U.S. Appl. No. 12/292,876.
Zitzmann et al. "Arginine-Glycine-Aspartic Acid (RGD)—Peptide Binds to Both Tumor and Tumor-Endothelial Cells In Vivo", Cancer Research, 62: 5139-5143, Sep. 15, 2002.
Examination Report Dated Feb. 15, 2010 From the Government of India, Patent Office Re.: Application No. 1885/CHENP/2006.
International Preliminary Report on Patentability Dated May 19, 2011 From the International Bureau of WIPO Re. Application No. PCT/IL2009/001046.
Response Dated May 19, 2011 to Communication Pursuant to Article 94(3) EPC of Jan. 19, 2011 From the European Patent Office Re. Application No. 07827230.9.
Official Action Dated Nov. 29, 2011 From the US Patent and Trademark Office Re.: U.S. Appl. No. 12/292,876.
Weis et al. "Tumor Angiogenesis: Molecular Pathways and Therapeutic Targets", Nature Medicine, 17(11): 1359-1370, Nov. 2011.

* cited by examiner

|  | Amino acid number |
|---|---|
| Metalloprotease domain | 207-696 |
| Zink-binding concensus motif | 349-259 |
| NOVEL Angiogenic Peptide (HWRRAHLLPRLP) | 286-297 |
| Disintegrin-like domain | 421-508 |
| Cell attachment site (RGD) | 484-486 |
| EGF like domain | 657-685 |

SEQ ID NO:1

```
MRLALLWALG LLGAGSPLPS WPLPNIGGTE EQQAESEKAP REPLEPQVLQ DDLPISLKKV 70         80         90        100        110        120
LQTSLPEPLR IKLELDGDSH ILELLQNREL VPGRPTLVWY QPDGTRVVSE GHTLENCCYQ 130        140        150        160        170        180
GRVRGYAGSW VSICTCSGLR GLVVLTPERS YTLEQGPGDL QGPPIISRIQ DLHLPGHTCA 190        200        210        220        230        240
LSWRESVHTQ TPPEHPLGQR HIRRRRDVVT ETKTVELVIV ADHSEAQKYR DFQHLLNRTL 250        260        270        280        290        300
EVALLLDTFF RPLNVRVALV GLEAWTQRDL VEISPNPAVT LENFLHWRRA HLLPRLPHDS 310        320        330        340        350        360
AQLVTGTSFS GPTVGMAIQN SICSPDFSGG VNMDHSTSIL GVASSIAHEL GHSLGLDHDL 370        380        390        400        410        420
PGNSCPCPGP APAKTCIMEA STDFLPGLNF SNCSRRALEK ALLDGMGSCL FERLPSLPPM 430        440        450        460        470        480
AAFCGNMFVE PGEQCDCGFL DDCVDPCCDS LTCQLRPGAQ CASDGPCCQN CQLRPSGWQC 490        500        510        520        530        540
RPTRGDCDLP EFCPGDSSQC PPDVSLGDGE PCAGGQAVCM HGRCASYAQQ CQSLWGPGAQ 550        560        570        580        590        600
PAAPLCLQTA NTRGNAFGSC GRNPSGSYVS CTPRDAICGQ LQCQTGRTQP LLGSIRDLLW 610        620        630        640        650        660
ETIDVNGTEL NCSWVHLDLG SDVAQPLLTL PGTACGPGLV CIDHRCQRVD LLGAQECRSK 670        680        690        700        710        720
CHGHGVCDSN RHCYCEEGWA PPDCTTQLKA TSSLTTGLLL SLLVLLVLVM LGASYWYRAR 730        740        750        760        770        780
LHQRLCQLKG PTCQYRAAQS GPSERPGPPQ RALLARGTKS QGPAKPPPPR KPLPADPQGR 790        800        810
CPSGDLPGPG AGIPPLVVPS RPAPPPPTVS SLYL
```

Fig. 2b

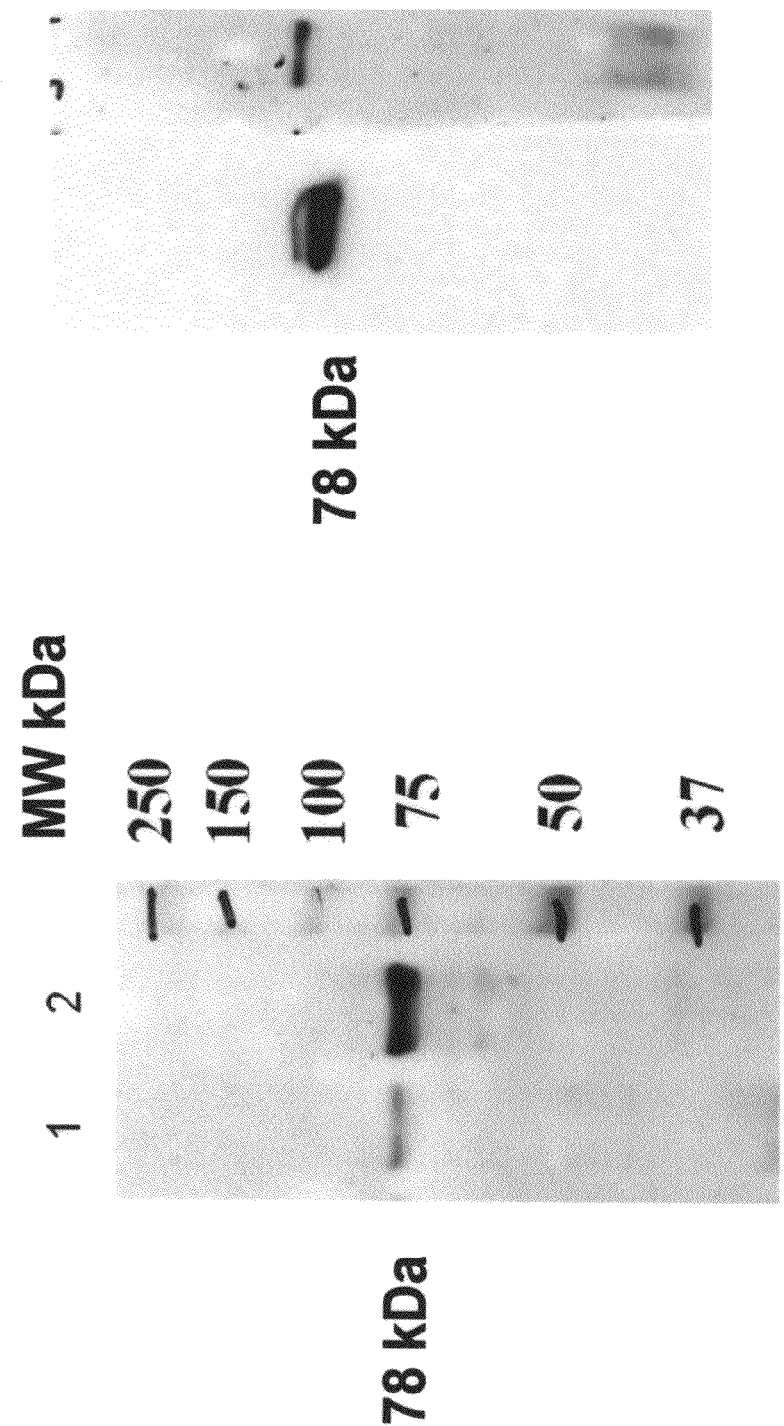

HT-29 colon carcinoma

MCF7 breast carcinoma

K562

SK-28 melanoma

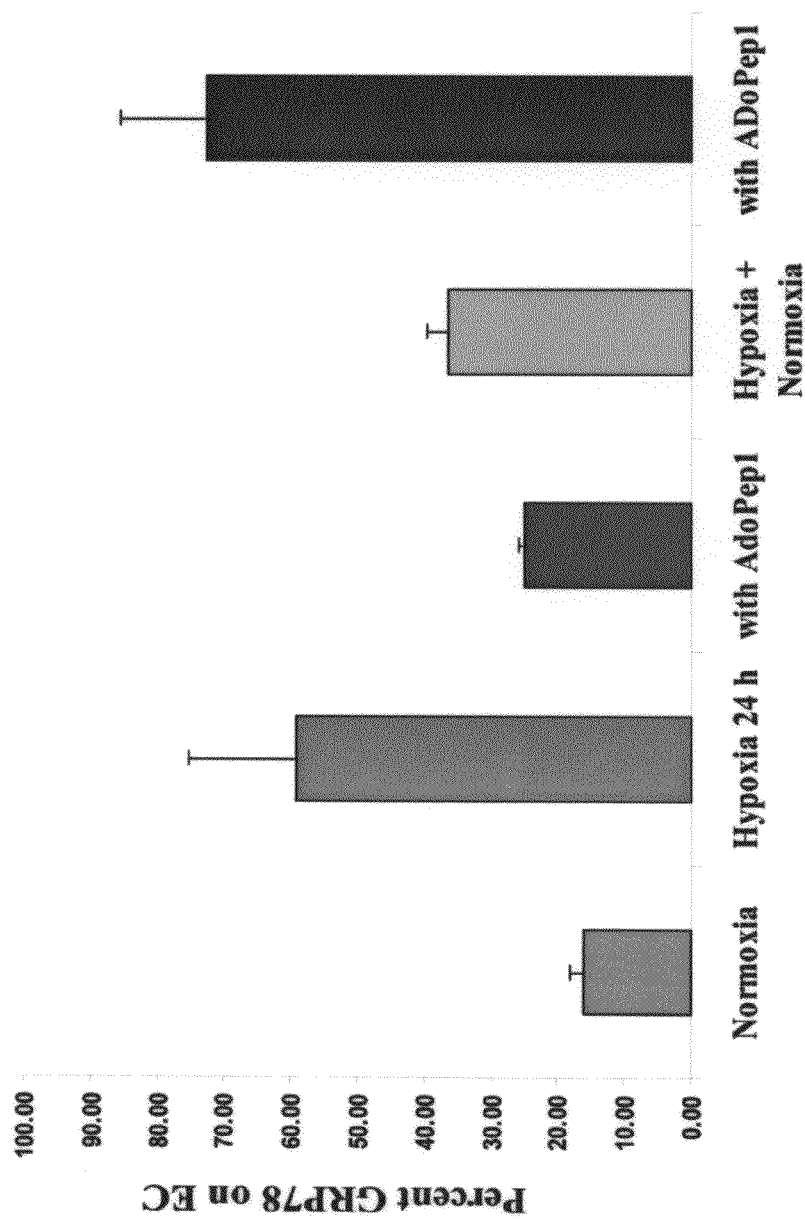

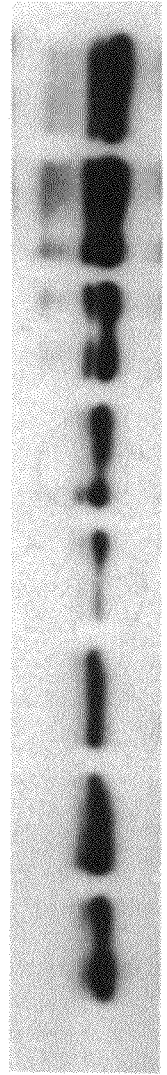
Fig. 32a
Fig. 32b

SEQUENCE LISTING

<160> NUMBER OF SEQ ID NOS: 98

<210> SEQ ID NO 1
<211> LENGTH: 814
<212> TYPE: PRT
<213> ORGANISM: Homo sapiens

<400> SEQUENCE: 1

```
Met Arg Leu Ala Leu Leu Trp Ala Leu Gly Leu Leu Gly Ala Gly Ser
1               5                   10                  15

Pro Leu Pro Ser Trp Pro Leu Pro Asn Ile Gly Gly Thr Glu Glu Gln
            20                  25                  30

Gln Ala Glu Ser Glu Lys Ala Pro Arg Glu Pro Leu Glu Pro Gln Val
        35                  40                  45

Leu Gln Asp Asp Leu Pro Ile Ser Leu Lys Lys Val Leu Gln Thr Ser
    50                  55                  60

Leu Pro Glu Pro Leu Arg Ile Lys Leu Glu Leu Asp Gly Asp Ser His
65                  70                  75                  80

Ile Leu Glu Leu Leu Gln Asn Arg Glu Leu Val Pro Gly Arg Pro Thr
                85                  90                  95

Leu Val Trp Tyr Gln Pro Asp Gly Thr Arg Val Val Ser Glu Gly His
            100                 105                 110

Thr Leu Glu Asn Cys Cys Tyr Gln Gly Arg Val Arg Gly Tyr Ala Gly
        115                 120                 125

Ser Trp Val Ser Ile Cys Thr Cys Ser Gly Leu Arg Gly Leu Val Val
    130                 135                 140

Leu Thr Pro Glu Arg Ser Tyr Thr Leu Glu Gln Gly Pro Gly Asp Leu
145                 150                 155                 160

Gln Gly Pro Pro Ile Ile Ser Arg Ile Gln Asp Leu His Leu Pro Gly
                165                 170                 175

His Thr Cys Ala Leu Ser Trp Arg Glu Ser Val His Thr Gln Thr Pro
            180                 185                 190

Pro Glu His Pro Leu Gly Gln Arg His Ile Arg Arg Arg Arg Asp Val
        195                 200                 205

Val Thr Glu Thr Lys Thr Val Glu Leu Val Ile Val Ala Asp His Ser
    210                 215                 220

Glu Ala Gln Lys Tyr Arg Asp Phe Gln His Leu Leu Asn Arg Thr Leu
225                 230                 235                 240

Glu Val Ala Leu Leu Leu Asp Thr Phe Phe Arg Pro Leu Asn Val Arg
                245                 250                 255

Val Ala Leu Val Gly Leu Glu Ala Trp Thr Gln Arg Asp Leu Val Glu
            260                 265                 270

Ile Ser Pro Asn Pro Ala Val Thr Leu Glu Asn Phe Leu His Trp Arg
        275                 280                 285

Arg Ala His Leu Leu Pro Arg Leu Pro His Asp Ser Ala Gln Leu Val
    290                 295                 300

Thr Gly Thr Ser Phe Ser Gly Pro Thr Val Gly Met Ala Ile Gln Asn
305                 310                 315                 320

Ser Ile Cys Ser Pro Asp Phe Ser Gly Gly Val Asn Met Asp His Ser
                325                 330                 335

Thr Ser Ile Leu Gly Val Ala Ser Ser Ile Ala His Glu Leu Gly His
            340                 345                 350

Ser Leu Gly Leu Asp His Asp Leu Pro Gly Asn Ser Cys Pro Cys Pro
        355                 360                 365
```

-continued

```
Gly Pro Ala Pro Ala Lys Thr Cys Ile Met Glu Ala Ser Thr Asp Phe
        370                 375                 380

Leu Pro Gly Leu Asn Phe Ser Asn Cys Ser Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
            420                 425                 430

Glu Gln Cys Asp Cys Gly Phe Leu Asp Asp Cys Val Asp Pro Cys Cys
        435                 440                 445

Asp Ser Leu Thr Cys Gln Leu Arg Pro Gly Ala Gln Cys Ala Ser Asp
        450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
            500                 505                 510

Ala Gly Gly Gln Ala Val Cys Met His Gly Arg Cys Ala Ser Tyr Ala
            515                 520                 525

Gln Gln Cys Gln Ser Leu Trp Gly Pro Gly Ala Gln Pro Ala Ala Pro
        530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
            580                 585                 590

Gly Ser Ile Arg Asp Leu Leu Trp Glu Thr Ile Asp Val Asn Gly Thr
        595                 600                 605

Glu Leu Asn Cys Ser Trp Val His Leu Asp Leu Gly Ser Asp Val Ala
        610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
            660                 665                 670

Cys Tyr Cys Glu Glu Gly Trp Ala Pro Pro Asp Cys Thr Thr Gln Leu
            675                 680                 685

Lys Ala Thr Ser Ser Leu Thr Thr Gly Leu Leu Leu Ser Leu Leu Val
        690                 695                 700

Leu Leu Val Leu Val Met Leu Gly Ala Ser Tyr Trp Tyr Arg Ala Arg
705                 710                 715                 720

Leu His Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
            740                 745                 750

Leu Leu Ala Arg Gly Thr Lys Ser Gln Gly Pro Ala Lys Pro Pro Pro
        755                 760                 765

Pro Arg Lys Pro Leu Pro Ala Asp Pro Gln Gly Arg Cys Pro Ser Gly
770                 775                 780
```

```
Asp Leu Pro Gly Pro Gly Ala Gly Ile Pro Pro Leu Val Val Pro Ser
785                 790                 795                 800

Arg Pro Ala Pro Pro Pro Thr Val Ser Ser Leu Tyr Leu
                805                 810
```

<210> SEQ ID NO 2
<211> LENGTH: 12
<212> TYPE: PRT
<213> ORGANISM: Artificial sequence
<220> FEATURE:
<223> OTHER INFORMATION: Synthetic peptide

<400> SEQUENCE: 2

```
His Trp Arg Arg Ala His Leu Leu Pro Arg Leu Pro
1               5                   10
```

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

```
Glu Asn Phe Leu His Trp Arg Arg Ala His Leu Leu
1               5                   10
```

<210> SEQ ID NO 4
<211> LENGTH: 12
<212> TYPE: PRT
<213> ORGANISM: Artificial sequence
<220> FEATURE:
<223> OTHER INFORMATION: Synthetic peptide

<400> SEQUENCE: 4

```
Ala Val Thr Leu Glu Asn Phe Leu His Trp Arg Arg
1               5                   10
```

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

```
His Trp Arg Arg
1
```

<210> SEQ ID NO 6
<211> LENGTH: 5
<212> TYPE: PRT
<213> ORGANISM: Artificial sequence
<220> FEATURE:
<223> OTHER INFORMATION: Synthetic peptide

<400> SEQUENCE: 6

```
Ala His Leu Leu Pro
1               5
```

<210> SEQ ID NO 7
<211> LENGTH: 5
<212> TYPE: PRT
<213> ORGANISM: Artificial sequence
<220> FEATURE:
<223> OTHER INFORMATION: Synthetic peptide -continued

```
<400> SEQUENCE: 7

His Trp Arg Arg Pro
1               5

<210> SEQ ID NO 8
<211> LENGTH: 5
<212> TYPE: PRT
<213> ORGANISM: Artificial sequence
<220> FEATURE:
<223> OTHER INFORMATION: Synthetic peptide

<400> SEQUENCE: 8

His Trp Arg Arg Ala
1               5

<210> SEQ ID NO 9
<211> LENGTH: 654
<212> TYPE: PRT
<213> ORGANISM: Homo sapiens

<400> SEQUENCE: 9

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285
```

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
530                 535                 540

Ala Glu Lys Phe Ala Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
                565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
        595                 600                 605

Gln Asp Ala Asp Ile Glu Asp Phe Lys Ala Lys Lys Lys Glu Leu Glu
        610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
                645                 650

<210> SEQ ID NO 10
<211> LENGTH: 12
<212> TYPE: PRT
<213> ORGANISM: Artificial sequence
<220> FEATURE:
<223> OTHER INFORMATION: Synthetic peptide

```
<400> SEQUENCE: 10

Arg Tyr His Leu Ile Pro Arg Gly Trp Asp His Ser
1               5                   10

<210> SEQ ID NO 11
<211> LENGTH: 12
<212> TYPE: PRT
<213> ORGANISM: Artificial sequence
<220> FEATURE:
<223> OTHER INFORMATION: Synthetic peptide

<400> SEQUENCE: 11

Tyr Pro His Ile Asp Ser Leu Gly His Trp Arg Arg
1               5                   10

<210> SEQ ID NO 12
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 12

Ala Lys Phe Glu Glu Leu Asn Met Asp Leu Phe Arg
1               5                   10

<210> SEQ ID NO 13
<211> LENGTH: 15
<212> TYPE: PRT
<213> ORGANISM: Artificial sequence
<220> FEATURE:
<223> OTHER INFORMATION: GRP78 peptide identified by mass spectrometry

<400> SEQUENCE: 13

Lys Ser Asp Ile Asp Glu Ile Val Leu Val Gly Gly Ser Thr Arg
1               5                   10                  15

<210> SEQ ID NO 14
<211> LENGTH: 10
<212> TYPE: PRT
<213> ORGANISM: Artificial sequence
<220> FEATURE:
<223> OTHER INFORMATION: GRP78 peptide identified by mass spectrometry

<400> SEQUENCE: 14

Val Tyr Glu Gly Glu Arg Pro Leu Thr Lys
1               5                   10

<210> SEQ ID NO 15
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 15

Asp Ala Gly Thr Ile Ala Gly Leu Asn Val Met Arg
1               5                   10

<210> SEQ ID NO 16
<211> LENGTH: 11
<212> TYPE: PRT
<213> ORGANISM: Artificial sequence
<220> FEATURE:
<223> OTHER INFORMATION: GRP78 peptide identified by mass spectrometry
```

```
<400> SEQUENCE: 16

Val Glu Ile Ile Ala Asn Asp Gln Gly Asn Arg
1               5                   10

<210> SEQ ID NO 17
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 17

Asp Ala Gly Thr Ile Ala Gly Leu Asn Val Met Arg
1               5                   10

<210> SEQ ID NO 18
<211> LENGTH: 11
<212> TYPE: PRT
<213> ORGANISM: Artificial sequence
<220> FEATURE:
<223> OTHER INFORMATION: GRP78 peptide identified by mass spectrometry

<400> SEQUENCE: 18

Met Lys Glu Thr Ala Glu Ala Tyr Leu Gly Lys
1               5                   10

<210> SEQ ID NO 19
<211> LENGTH: 17
<212> TYPE: PRT
<213> ORGANISM: Artificial sequence
<220> FEATURE:
<223> OTHER INFORMATION: GRP78 peptide identified by mass spectrometry

<400> SEQUENCE: 19

Val Thr His Ala Val Val Thr Val Pro Ala Tyr Phe Asn Asp Ala Gln
1               5                   10                  15

Arg

<210> SEQ ID NO 20
<211> LENGTH: 18
<212> TYPE: PRT
<213> ORGANISM: Artificial sequence
<220> FEATURE:
<223> OTHER INFORMATION: GRP78 peptide identified by mass spectrometry

<400> SEQUENCE: 20

Asp Asn His Leu Leu Gly Thr Phe Asp Leu Thr Gly Ile Pro Pro Ala
1               5                   10                  15

Pro Arg

<210> SEQ ID NO 21
<211> LENGTH: 10
<212> TYPE: PRT
<213> ORGANISM: Artificial sequence
<220> FEATURE:
<223> OTHER INFORMATION: GRP78 peptide identified by mass spectrometry

<400> SEQUENCE: 21

Phe Glu Glu Leu Asn Met Asp Leu Phe Arg
1               5                   10

<210> SEQ ID NO 22
<211> LENGTH: 11
<212> TYPE: PRT
<213> ORGANISM: Artificial sequence
```

```
<220> FEATURE:
<223> OTHER INFORMATION: GRP78 peptide identified by mass spectrometry

<400> SEQUENCE: 22

Asn Glu Leu Glu Ser Tyr Ala Tyr Ser Leu Lys
1               5                   10

<210> SEQ ID NO 23
<211> LENGTH: 10
<212> TYPE: PRT
<213> ORGANISM: Artificial sequence
<220> FEATURE:
<223> OTHER INFORMATION: GRP78 peptide identified by mass spectrometry

<400> SEQUENCE: 23

Phe Glu Glu Leu Asn Met Asp Leu Phe Arg
1               5                   10

<210> SEQ ID NO 24
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 24

Glu Leu Glu Glu Ile Val Gln Pro Ile Ile Ser Lys
1               5                   10

<210> SEQ ID NO 25
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 25

Thr Trp Asn Asp Pro Ser Val Gln Gln Asp Ile Lys
1               5                   10

<210> SEQ ID NO 26
<211> LENGTH: 14
<212> TYPE: PRT
<213> ORGANISM: Artificial sequence
<220> FEATURE:
<223> OTHER INFORMATION: GRP78 peptide identified by mass spectrometry

<400> SEQUENCE: 26

Ser Asp Ile Asp Glu Ile Val Leu Val Gly Gly Ser Thr Arg
1               5                   10

<210> SEQ ID NO 27
<211> LENGTH: 7
<212> TYPE: PRT
<213> ORGANISM: Artificial sequence
<220> FEATURE:
<223> OTHER INFORMATION: GRP78 peptide identified by mass spectrometry

<400> SEQUENCE: 27

Asn Thr Val Val Pro Thr Lys
1               5

<210> SEQ ID NO 28
<211> LENGTH: 12
<212> TYPE: PRT
<213> ORGANISM: Artificial sequence
<220> FEATURE:
<223> OTHER INFORMATION: GRP78 peptide identified by mass spectrometry
```

```
<400> SEQUENCE: 28

Ala Lys Phe Glu Glu Leu Asn Met Asp Leu Phe Arg
1               5                   10

<210> SEQ ID NO 29
<211> LENGTH: 14
<212> TYPE: PRT
<213> ORGANISM: Artificial sequence
<220> FEATURE:
<223> OTHER INFORMATION: GRP78 peptide identified by mass spectrometry

<400> SEQUENCE: 29

Thr Phe Ala Pro Glu Glu Ile Ser Ala Met Val Leu Thr Lys
1               5                   10

<210> SEQ ID NO 30
<211> LENGTH: 14
<212> TYPE: PRT
<213> ORGANISM: Artificial sequence
<220> FEATURE:
<223> OTHER INFORMATION: GRP78 peptide identified by mass spectrometry

<400> SEQUENCE: 30

Ile Thr Pro Ser Tyr Val Ala Phe Thr Pro Glu Gly Glu Arg
1               5                   10

<210> SEQ ID NO 31
<211> LENGTH: 15
<212> TYPE: PRT
<213> ORGANISM: Artificial sequence
<220> FEATURE:
<223> OTHER INFORMATION: GRP78 peptide identified by mass spectrometry

<400> SEQUENCE: 31

Thr Lys Pro Tyr Ile Gln Val Asp Ile Gly Gly Gly Gln Thr Lys
1               5                   10                  15

<210> SEQ ID NO 32
<211> LENGTH: 16
<212> TYPE: PRT
<213> ORGANISM: Artificial sequence
<220> FEATURE:
<223> OTHER INFORMATION: GRP78 peptide identified by mass spectrometry

<400> SEQUENCE: 32

Ile Ile Asn Glu Pro Thr Ala Ala Ala Ile Ala Tyr Gly Leu Asp Lys
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: GRP78 peptide identified by mass spectrometry

<400> SEQUENCE: 33

Asn Gln Leu Thr Ser Asn Pro Glu Asn Thr Val Phe Asp Ala Lys
1               5                   10                  15

<210> SEQ ID NO 34
<211> LENGTH: 17
<212> TYPE: PRT
<213> ORGANISM: Artificial sequence
<220> FEATURE:
<223> OTHER INFORMATION: GRP78 peptide identified by mass spectrometry
```

```
<400> SEQUENCE: 34

Ser Gln Ile Phe Ser Thr Ala Ser Asp Asn Gln Pro Thr Val Thr Ile
1               5                   10                  15

Lys

<210> SEQ ID NO 35
<211> LENGTH: 17
<212> TYPE: PRT
<213> ORGANISM: Artificial sequence
<220> FEATURE:
<223> OTHER INFORMATION: GRP78 peptide identified by mass spectrometry

<400> SEQUENCE: 35

Val Thr His Ala Val Val Thr Val Pro Ala Tyr Phe Asn Asp Ala Gln
1               5                   10                  15

Arg

<210> SEQ ID NO 36
<211> LENGTH: 18
<212> TYPE: PRT
<213> ORGANISM: Artificial sequence
<220> FEATURE:
<223> OTHER INFORMATION: GRP78 peptide identified by mass spectrometry

<400> SEQUENCE: 36

Asp Asn His Leu Leu Gly Thr Phe Asp Leu Thr Gly Ile Pro Pro Ala
1               5                   10                  15

Pro Arg

<210> SEQ ID NO 37
<211> LENGTH: 18
<212> TYPE: PRT
<213> ORGANISM: Artificial sequence
<220> FEATURE:
<223> OTHER INFORMATION: GRP78 peptide identified by mass spectrometry

<400> SEQUENCE: 37

Ile Glu Ile Glu Ser Phe Tyr Glu Gly Glu Asp Phe Ser Glu Thr Leu
1               5                   10                  15

Thr Arg

<210> SEQ ID NO 38
<211> LENGTH: 21
<212> TYPE: PRT
<213> ORGANISM: Artificial sequence
<220> FEATURE:
<223> OTHER INFORMATION: GRP78 peptide identified by mass spectrometry

<400> SEQUENCE: 38

Leu Tyr Gly Ser Ala Gly Pro Pro Thr Gly Glu Glu Asp Thr Ala
1               5                   10                  15

Glu Lys Asp Glu Leu
                20

<210> SEQ ID NO 39
<211> LENGTH: 15
<212> TYPE: PRT
<213> ORGANISM: Artificial sequence
<220> FEATURE:
<223> OTHER INFORMATION: GRP78 peptide identified by mass spectrometry

<400> SEQUENCE: 39

Lys Ser Asp Ile Asp Glu Ile Val Leu Val Gly Gly Ser Thr Arg
1               5                   10                  15
```

```
<210> SEQ ID NO 40
<211> LENGTH: 10
<212> TYPE: PRT
<213> ORGANISM: Artificial sequence
<220> FEATURE:
<223> OTHER INFORMATION: GRP78 peptide identified by mass spectrometry

<400> SEQUENCE: 40

Val Tyr Glu Gly Glu Arg Pro Leu Thr Lys
1               5                   10

<210> SEQ ID NO 41
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 41

Asp Ala Gly Thr Ile Ala Gly Leu Asn Val Met Arg
1               5                   10

<210> SEQ ID NO 42
<211> LENGTH: 11
<212> TYPE: PRT
<213> ORGANISM: Artificial sequence
<220> FEATURE:
<223> OTHER INFORMATION: GRP78 peptide identified by mass spectrometry

<400> SEQUENCE: 42

Val Glu Ile Ile Ala Asn Asp Gln Gly Asn Arg
1               5                   10

<210> SEQ ID NO 43
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 43

Asp Ala Gly Thr Ile Ala Gly Leu Asn Val Met Arg
1               5                   10

<210> SEQ ID NO 44
<211> LENGTH: 17
<212> TYPE: PRT
<213> ORGANISM: Artificial sequence
<220> FEATURE:
<223> OTHER INFORMATION: GRP78 peptide identified by mass spectrometry

<400> SEQUENCE: 44

Val Thr His Ala Val Val Thr Val Pro Ala Tyr Phe Asn Asp Ala Gln
1               5                   10                  15

Arg

<210> SEQ ID NO 45
<211> LENGTH: 18
<212> TYPE: PRT
<213> ORGANISM: Artificial sequence
<220> FEATURE:
<223> OTHER INFORMATION: GRP78 peptide identified by mass spectrometry

<400> SEQUENCE: 45

Asp Asn His Leu Leu Gly Thr Phe Asp Leu Thr Gly Ile Pro Pro Ala
1               5                   10                  15

Pro Arg
```

```
<210> SEQ ID NO 46
<211> LENGTH: 10
<212> TYPE: PRT
<213> ORGANISM: Artificial sequence
<220> FEATURE:
<223> OTHER INFORMATION: GRP78 peptide identified by mass spectrometry

<400> SEQUENCE: 46

Phe Glu Glu Leu Asn Met Asp Leu Phe Arg
1               5                   10

<210> SEQ ID NO 47
<211> LENGTH: 11
<212> TYPE: PRT
<213> ORGANISM: Artificial sequence
<220> FEATURE:
<223> OTHER INFORMATION: GRP78 peptide identified by mass spectrometry

<400> SEQUENCE: 47

Asn Glu Leu Glu Ser Tyr Ala Tyr Ser Leu Lys
1               5                   10

<210> SEQ ID NO 48
<211> LENGTH: 16
<212> TYPE: PRT
<213> ORGANISM: Artificial sequence
<220> FEATURE:
<223> OTHER INFORMATION: GRP78 peptide identified by mass spectrometry

<400> SEQUENCE: 48

Ile Glu Trp Leu Glu Ser His Gln Asp Ala Asp Ile Glu Asp Phe Lys
1               5                   10                  15

<210> SEQ ID NO 49
<211> LENGTH: 10
<212> TYPE: PRT
<213> ORGANISM: Artificial sequence
<220> FEATURE:
<223> OTHER INFORMATION: GRP78 peptide identified by mass spectrometry

<400> SEQUENCE: 49

Phe Glu Glu Leu Asn Met Asp Leu Phe Arg
1               5                   10

<210> SEQ ID NO 50
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 50

Glu Leu Glu Glu Ile Val Gln Pro Ile Ile Ser Lys
1               5                   10

<210> SEQ ID NO 51
<211> LENGTH: 12
<212> TYPE: PRT
<213> ORGANISM: Artificial sequence
<220> FEATURE:
<223> OTHER INFORMATION: GRP78 peptide identified by mass spectrometry

<400> SEQUENCE: 51

Thr Trp Asn Asp Pro Ser Val Gln Gln Asp Ile Lys
1               5                   10
```

```
<210> SEQ ID NO 52
<211> LENGTH: 14
<212> TYPE: PRT
<213> ORGANISM: Artificial sequence
<220> FEATURE:
<223> OTHER INFORMATION: GRP78 peptide identified by mass spectrometry

<400> SEQUENCE: 52

Ser Asp Ile Asp Glu Ile Val Leu Val Gly Gly Ser Thr Arg
1               5                   10

<210> SEQ ID NO 53
<211> LENGTH: 14
<212> TYPE: PRT
<213> ORGANISM: Artificial sequence
<220> FEATURE:
<223> OTHER INFORMATION: GRP78 peptide identified by mass spectrometry

<400> SEQUENCE: 53

Thr Phe Ala Pro Glu Glu Ile Ser Ala Met Val Leu Thr Lys
1               5                   10

<210> SEQ ID NO 54
<211> LENGTH: 14
<212> TYPE: PRT
<213> ORGANISM: Artificial sequence
<220> FEATURE:
<223> OTHER INFORMATION: GRP78 peptide identified by mass spectrometry

<400> SEQUENCE: 54

Ile Thr Pro Ser Tyr Val Ala Phe Thr Pro Glu Gly Glu Arg
1               5                   10

<210> SEQ ID NO 55
<211> LENGTH: 15
<212> TYPE: PRT
<213> ORGANISM: Artificial sequence
<220> FEATURE:
<223> OTHER INFORMATION: GRP78 peptide identified by mass spectrometry

<400> SEQUENCE: 55

Lys Ser Asp Ile Asp Glu Ile Val Leu Val Gly Gly Ser Thr Arg
1               5                   10                  15

<210> SEQ ID NO 56
<211> LENGTH: 16
<212> TYPE: PRT
<213> ORGANISM: Artificial sequence
<220> FEATURE:
<223> OTHER INFORMATION: GRP78 peptide identified by mass spectrometry

<400> SEQUENCE: 56

Ile Ile Asn Glu Pro Thr Ala Ala Ala Ile Ala Tyr Gly Leu Asp Lys
1               5                   10                  15

<210> SEQ ID NO 57
<211> LENGTH: 15
<212> TYPE: PRT
<213> ORGANISM: Artificial sequence
<220> FEATURE:
<223> OTHER INFORMATION: GRP78 peptide identified by mass spectrometry

<400> SEQUENCE: 57

Asn Gln Leu Thr Ser Asn Pro Glu Asn Thr Val Phe Asp Ala Lys
1               5                   10                  15
```

```
<210> SEQ ID NO 58
<211> LENGTH: 17
<212> TYPE: PRT
<213> ORGANISM: Artificial sequence
<220> FEATURE:
<223> OTHER INFORMATION: GRP78 peptide identified by mass spectrometry

<400> SEQUENCE: 58

Ser Gln Ile Phe Ser Thr Ala Ser Asp Asn Gln Pro Thr Val Thr Ile
1               5                   10                  15

Lys

<210> SEQ ID NO 59
<211> LENGTH: 18
<212> TYPE: PRT
<213> ORGANISM: Artificial sequence
<220> FEATURE:
<223> OTHER INFORMATION: GRP78 peptide identified by mass spectrometry

<400> SEQUENCE: 59

Ile Glu Ile Glu Ser Phe Tyr Glu Gly Glu Asp Phe Ser Glu Thr Leu
1               5                   10                  15

Thr Arg

<210> SEQ ID NO 60
<211> LENGTH: 21
<212> TYPE: PRT
<213> ORGANISM: Artificial sequence
<220> FEATURE:
<223> OTHER INFORMATION: GRP78 peptide identified by mass spectrometry

<400> SEQUENCE: 60

Leu Tyr Gly Ser Ala Gly Pro Pro Pro Thr Gly Glu Glu Asp Thr Ala
1               5                   10                  15

Glu Lys Asp Glu Leu
            20

<210> SEQ ID NO 61
<211> LENGTH: 5
<212> TYPE: PRT
<213> ORGANISM: Artificial sequence
<220> FEATURE:
<223> OTHER INFORMATION: Synthetic peptide

<400> SEQUENCE: 61

His Trp Arg Arg Arg
1               5

<210> SEQ ID NO 62
<211> LENGTH: 5
<212> TYPE: PRT
<213> ORGANISM: Artificial sequence
<220> FEATURE:
<223> OTHER INFORMATION: Synthetic peptide

<400> SEQUENCE: 62

His Trp Arg Arg Asn
1               5

<210> SEQ ID NO 63
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 63

His Trp Arg Arg Asp
1               5

<210> SEQ ID NO 64
<211> LENGTH: 5
<212> TYPE: PRT
<213> ORGANISM: Artificial sequence
<220> FEATURE:
<223> OTHER INFORMATION: Synthetic peptide

<400> SEQUENCE: 64

His Trp Arg Arg Cys
1               5

<210> SEQ ID NO 65
<211> LENGTH: 5
<212> TYPE: PRT
<213> ORGANISM: Artificial sequence
<220> FEATURE:
<223> OTHER INFORMATION: Synthetic peptide

<400> SEQUENCE: 65

His Trp Arg Arg Gln
1               5

<210> SEQ ID NO 66
<211> LENGTH: 5
<212> TYPE: PRT
<213> ORGANISM: Artificial sequence
<220> FEATURE:
<223> OTHER INFORMATION: Synthetic peptide

<400> SEQUENCE: 66

His Trp Arg Arg Glu
1               5

<210> SEQ ID NO 67
<211> LENGTH: 5
<212> TYPE: PRT
<213> ORGANISM: Artificial sequence
<220> FEATURE:
<223> OTHER INFORMATION: Synthetic peptide

<400> SEQUENCE: 67

His Trp Arg Arg Gly
1               5

<210> SEQ ID NO 68
<211> LENGTH: 5
<212> TYPE: PRT
<213> ORGANISM: Artificial sequence
<220> FEATURE:
<223> OTHER INFORMATION: Synthetic peptide

<400> SEQUENCE: 68

His Trp Arg Arg His
1               5

<210> SEQ ID NO 69
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 69

His Trp Arg Arg Ile
1               5

<210> SEQ ID NO 70
<211> LENGTH: 5
<212> TYPE: PRT
<213> ORGANISM: Artificial sequence
<220> FEATURE:
<223> OTHER INFORMATION: Synthetic peptide

<400> SEQUENCE: 70

His Trp Arg Arg Leu
1               5

<210> SEQ ID NO 71
<211> LENGTH: 5
<212> TYPE: PRT
<213> ORGANISM: Artificial sequence
<220> FEATURE:
<223> OTHER INFORMATION: Synthetic peptide

<400> SEQUENCE: 71

His Trp Arg Arg Lys
1               5

<210> SEQ ID NO 72
<211> LENGTH: 5
<212> TYPE: PRT
<213> ORGANISM: Artificial sequence
<220> FEATURE:
<223> OTHER INFORMATION: Synthetic peptide

<400> SEQUENCE: 72

His Trp Arg Arg Met
1               5

<210> SEQ ID NO 73
<211> LENGTH: 5
<212> TYPE: PRT
<213> ORGANISM: Artificial sequence
<220> FEATURE:
<223> OTHER INFORMATION: Synthetic peptide

<400> SEQUENCE: 73

His Trp Arg Arg Phe
1               5

<210> SEQ ID NO 74
<211> LENGTH: 5
<212> TYPE: PRT
<213> ORGANISM: Artificial sequence
<220> FEATURE:
<223> OTHER INFORMATION: Synthetic peptide

<400> SEQUENCE: 74

His Trp Arg Arg Ser
1               5

<210> SEQ ID NO 75
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 75

His Trp Arg Arg Thr
1               5

<210> SEQ ID NO 76
<211> LENGTH: 5
<212> TYPE: PRT
<213> ORGANISM: Artificial sequence
<220> FEATURE:
<223> OTHER INFORMATION: Synthetic peptide

<400> SEQUENCE: 76

His Trp Arg Arg Trp
1               5

<210> SEQ ID NO 77
<211> LENGTH: 5
<212> TYPE: PRT
<213> ORGANISM: Artificial sequence
<220> FEATURE:
<223> OTHER INFORMATION: Synthetic peptide

<400> SEQUENCE: 77

His Trp Arg Arg Tyr
1               5

<210> SEQ ID NO 78
<211> LENGTH: 5
<212> TYPE: PRT
<213> ORGANISM: Artificial sequence
<220> FEATURE:
<223> OTHER INFORMATION: Synthetic peptide

<400> SEQUENCE: 78

His Trp Arg Arg Val
1               5

<210> SEQ ID NO 79
<211> LENGTH: 5
<212> TYPE: PRT
<213> ORGANISM: Artificial sequence
<220> FEATURE:
<223> OTHER INFORMATION: Synthetic peptide

<400> SEQUENCE: 79

Ala His Trp Arg Arg
1               5

<210> SEQ ID NO 80
<211> LENGTH: 5
<212> TYPE: PRT
<213> ORGANISM: Artificial sequence
<220> FEATURE:
<223> OTHER INFORMATION: Synthetic peptide

<400> SEQUENCE: 80

Arg His Trp Arg Arg
1               5

<210> SEQ ID NO 81
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 81

Asn His Trp Arg Arg
1               5

<210> SEQ ID NO 82
<211> LENGTH: 5
<212> TYPE: PRT
<213> ORGANISM: Artificial sequence
<220> FEATURE:
<223> OTHER INFORMATION: Synthetic peptide

<400> SEQUENCE: 82

Asp His Trp Arg Arg
1               5

<210> SEQ ID NO 83
<211> LENGTH: 5
<212> TYPE: PRT
<213> ORGANISM: Artificial sequence
<220> FEATURE:
<223> OTHER INFORMATION: Synthetic peptide

<400> SEQUENCE: 83

Cys His Trp Arg Arg
1               5

<210> SEQ ID NO 84
<211> LENGTH: 5
<212> TYPE: PRT
<213> ORGANISM: Artificial sequence
<220> FEATURE:
<223> OTHER INFORMATION: Synthetic peptide

<400> SEQUENCE: 84

Gln His Trp Arg Arg
1               5

<210> SEQ ID NO 85
<211> LENGTH: 5
<212> TYPE: PRT
<213> ORGANISM: Artificial sequence
<220> FEATURE:
<223> OTHER INFORMATION: Synthetic peptide

<400> SEQUENCE: 85

Glu His Trp Arg Arg
1               5

<210> SEQ ID NO 86
<211> LENGTH: 5
<212> TYPE: PRT
<213> ORGANISM: Artificial sequence
<220> FEATURE:
<223> OTHER INFORMATION: Synthetic peptide

<400> SEQUENCE: 86

Gly His Trp Arg Arg
1               5

<210> SEQ ID NO 87
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 87

His His Trp Arg Arg
1               5

<210> SEQ ID NO 88
<211> LENGTH: 5
<212> TYPE: PRT
<213> ORGANISM: Artificial sequence
<220> FEATURE:
<223> OTHER INFORMATION: Synthetic peptide

<400> SEQUENCE: 88

Ile His Trp Arg Arg
1               5

<210> SEQ ID NO 89
<211> LENGTH: 5
<212> TYPE: PRT
<213> ORGANISM: Artificial sequence
<220> FEATURE:
<223> OTHER INFORMATION: Synthetic peptide

<400> SEQUENCE: 89

Leu His Trp Arg Arg
1               5

<210> SEQ ID NO 90
<211> LENGTH: 5
<212> TYPE: PRT
<213> ORGANISM: Artificial sequence
<220> FEATURE:
<223> OTHER INFORMATION: Synthetic peptide

<400> SEQUENCE: 90

Lys His Trp Arg Arg
1               5

<210> SEQ ID NO 91
<211> LENGTH: 5
<212> TYPE: PRT
<213> ORGANISM: Artificial sequence
<220> FEATURE:
<223> OTHER INFORMATION: Synthetic peptide

<400> SEQUENCE: 91

Met His Trp Arg Arg
1               5

<210> SEQ ID NO 92
<211> LENGTH: 5
<212> TYPE: PRT
<213> ORGANISM: Artificial sequence
<220> FEATURE:
<223> OTHER INFORMATION: Synthetic peptide

<400> SEQUENCE: 92

Phe His Trp Arg Arg
1               5

<210> SEQ ID NO 93
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 93

Pro His Trp Arg Arg
1               5

<210> SEQ ID NO 94
<211> LENGTH: 5
<212> TYPE: PRT
<213> ORGANISM: Artificial sequence
<220> FEATURE:
<223> OTHER INFORMATION: Synthetic peptide

<400> SEQUENCE: 94

Ser His Trp Arg Arg
1               5

<210> SEQ ID NO 95
<211> LENGTH: 5
<212> TYPE: PRT
<213> ORGANISM: Artificial sequence
<220> FEATURE:
<223> OTHER INFORMATION: Synthetic peptide

<400> SEQUENCE: 95

Thr His Trp Arg Arg
1               5

<210> SEQ ID NO 96
<211> LENGTH: 5
<212> TYPE: PRT
<213> ORGANISM: Artificial sequence
<220> FEATURE:
<223> OTHER INFORMATION: Synthetic peptide

<400> SEQUENCE: 96

Trp His Trp Arg Arg
1               5

<210> SEQ ID NO 97
<211> LENGTH: 5
<212> TYPE: PRT
<213> ORGANISM: Artificial sequence
<220> FEATURE:
<223> OTHER INFORMATION: Synthetic peptide

<400> SEQUENCE: 97

Tyr His Trp Arg Arg
1               5

<210> SEQ ID NO 98
<211> LENGTH: 5
<212> TYPE: PRT
<213> ORGANISM: Artificial sequence
<220> FEATURE:
<223> OTHER INFORMATION: Synthetic peptide

<400> SEQUENCE: 98

Val His Trp Arg Arg
1               5
```

COMPOSITIONS AND METHODS FOR INDUCING ANGIOGENESIS

RELATED APPLICATIONS

This application is a National Phase Application of PCT Application No. PCT/IL2007/001256 having International Filing Date of Oct. 18, 2007, which claims benefit of U.S. Provisional Patent Application No. 60/852,645, filed on Oct. 19, 2006 and U.S. Provisional Patent Application No. 60/897,498, filed on Jan. 26, 2007. The contents of the above Applications are all incorporated herein by reference.

FIELD AND BACKGROUND OF THE INVENTION

Angiogenesis is the process of generating new capillary blood vessels and involves an interplay between cells and soluble factors. Thus, activated endothelial cells migrate and proliferate to form new vessels, which are surrounded by layers of periendothelial cells; small blood vessels are surrounded by pericytes and large blood vessels are surrounded by smooth muscle cells.

Numerous factors are known to regulate angiogenesis. These include soluble factors and tissue oxygen. Factors known to positively regulate angiogenesis include Vascular Endothelium Growth Factor (VEGF), basic Fibroblast Growth Factor (bFGF), acidic FGF/FGF-1 and hypoxia-inducible factor-1α (HIF-1α). Hypoxia induces the expression of several gene products such as erytropoietin, VEGF, bFGF and glycolytic enzymes.

Angiogenesis-dependent pathologies result from disregulated angiogenesis, i.e., excessive amounts of new blood vessels or insufficient number of blood vessels. Insufficient angiogenesis is related to a large number of diseases and conditions, such as coronary artery diseases, delayed wound healing, delayed ulcer healing, reproduction associated disorders, arteriosclerosis, myocardial ischemia, peripheral ischemia, cerebral ischemia, retinopathy, remodeling disorder, von Hippel-Lindau syndrome, diabetes and hereditary hemorrhagic telengiectasia. On the other hand, excess of angiogenesis is characteristic to cancerous cells and cancer metastasis.

Common treatment of ischemic diseases (e.g., peripheral artery diseases such as critical limb ischemia, coronary artery disease) involves mechanical revascularization by percutaneous techniques or a bypass surgery using arterial and venous conduits as grafts onto the coronary arterial tree. However, these treatment modalities have significant limitations in individuals with diffuse atherosclerotic disease or severe small vessel coronary artery disease, in diabetic patients, as well as in individuals who have already undergone surgical or percutaneous procedures. For these reasons, therapeutic angiogenesis, aimed at stimulating new blood vessel growth, is highly desirable.

The therapeutic concept of angiogenesis therapy is based on the premise that the existing potential for vascular growth inherent to vascular tissue can be utilized to induce the development of new blood vessels under the influence of the appropriate angiogenic molecules.

Animal studies have proven the feasibility of enhancing collateral perfusion and function in experimental models of acute and chronic ischemia via exogenous angiogenic compounds (Sun Q, Chen R R, Shen Y, Mooney D J, Rajagopalan S, Grossman P M. Sustained vascular endothelial growth factor delivery enhances angiogenesis and perfusion in ischemic hind limb. Pharm. Res. 2005; 22, 1110-6). In addition, synthetic peptides encompassing portions of the human FGF and VEGF proteins were described to efficiently agonize or antagonize the biological functions of the growth factor family members. Furthermore, screening a combinatorial phage display library of random 12-mer peptides resulted in isolation of specific peptides capable of binding the cell-surface of endothelial cells and triggering angiogenic processes which included endothelial cell-proliferation and vascularization (PCT Pub. WO2005/039616 to the present inventors).

Members of the ADAM (A Disintegrin And Metalloproteinase) family of proteolytic enzymes are implicated in the processing of many single transmembrane-bound proteins ranging from cell surface receptors to growth factors and cytokines. The disintegrin domains in the ADAM proteins compete with extracellular proteins (ECM) on integrin binding. As such, the ADAM proteins are thought to be involved in the regulation of cell/ECM- and cell/cell-interactions in many physiological and pathophysiological conditions. In addition, the conserved metalloprotease domain in ADAM proteins is thought to be involved in shedding of biologically important cell surface proteins. Thus, it was suggested that ADAM proteases could facilitate cell migration by shedding ectodomains and by remodeling of the ECM (Trochon V., et al., 1998).

ADAM15 (also known as metargidin) is a membrane-anchored glycoprotein implicated in cell-cell or cell-matrix interactions and in the proteolysis of molecules on the cell surface or extracellular matrix. The expression level of ADAM15 was found to be elevated in numerous tissues and conditions characterized by extensive remodeling such as vascular cells, endocardium, atherosclerotic lesions, rheumatoid tissue, chondrosarcoma and atrial fibrillation and dilatation. In addition, ADAM15 is expressed in human aortic smooth muscle and cultured Umbilical Vein Endothelial Cells (HUVECs) and the ADAM15 gene was localized to human chromosome band 1q21.3 that is amplified in several types of cancers.

The possible role of ADAM15 in neovascularization was studied in mice lacking the ADAM15 gene (i.e., ADAM15 knock out mice). The ADAM15 knock out mice exhibit a major reduction in neovascularization compared to wild-type controls (Bohm B B, Aigner T, Roy B Brodie T A, Blobel C P Burkhardt H; Arthritis Rheum. 2005 52, 4 1100-9); a strongly reduced angiogenic response in a model of hypoxia-induced proliferative retinopathy; and significantly smaller tumors which develop after implantation of melanoma cells. Specific candidate substrates for ADAM15 in the context of neovascularization include Notch1 and -4, PECAM-1, VE-cadherin, TIE-2, membrane type 1 MMP and possibly also Kit-ligand. On the other hand, although ADAM15 demonstrates strong and specific interactions with hematopoietic Src family kinases, which are known to be required for VEGF-mediated angiogenesis, nor VEGF or bFGF induce changes in ADAM15 expression in HUVECs.

Inhibition of ADAM15 by specific antibodies or the metalloprotease inhibitor BB3103 resulted in blockage of human mesangial cell migration and suggested that the metalloprotease activity is essential for this process.

The glucose-regulated protein (GRP78) (also known as HSPA5 or BiP), is a member of the heat-shock protein-70 (HSP70) family, highly conserved molecules that act as molecular chaperones and is involved in the folding and assembly of proteins in the endoplasmic reticulum (ER). GRP78 was found to be upregulated in drug-resistant lung cancer cell lines and its expression level was inversely correlated to the microvessel density (MVD) [Koomaqi R., et al., 1999; Anticancer Res. 19(5B): 4333-6]. In contrast, inhibition of GRP78 using small interfering RNA resulted in sensitization of human breast cancer cells to etoposide-mediated cell death [Dong D., et al., 2005, Cancer Res. 65(13): 5785-91]. On the other hand, no correlation was found between the expression level of ER-stress response protein GRP78 and the resistance to hypoxia or ER stresses [Koshikawa N., et al., 2006, Oncogene 25(6):917-28]. Recently, GRP78 was found to be exposed on the cell surface of proliferating endothelial cells and stressed tumor cells and to play a key role in the anti-angiogenic and antitumor activity of Kringle 5 (K5) [Davidson D J., et al., 2005, Cancer Res. 65(11): 4663-72].

SUMMARY OF THE INVENTION

According to one aspect of the present invention there is provided an isolated peptide comprising an amino acid sequence HWRR as set forth by SEQ ID NO:5, wherein the peptide consists of 4 or 5 amino acids.

According to another aspect of the present invention there is provided an isolated peptide comprising an amino acid sequence HWRR as set forth by SEQ ID NO:5, with the proviso that the peptide is not SEQ ID NO:11 (YPHIDSLGH-WRR).

According to yet another aspect of the present invention there is provided a composition-of-matter comprising at least one peptide of the invention.

According to still another aspect of the present invention there is provided a pharmaceutical composition comprising as an active ingredient at least one peptide of the invention and a pharmaceutically acceptable carrier or diluent.

According to an additional aspect of the present invention there is provided a method of inducing angiogenesis in a subject, the method comprising administering to the subject a therapeutically effective amount of at least one peptide of the invention, to thereby induce angiogenesis in the subject.

According to yet an additional aspect of the present invention there is provided use of at least one peptide of the invention for the manufacturing of a medicament identified for inducing angiogenesis in a tissue of a subject.

According to still an additional aspect of the present invention there is provided use of at least one peptide of the invention for the manufacturing of a medicament identified for treating a pathology selected from the group consisting of delayed wound-healing, delayed ulcer healing, reproduction associated disorder, arteriosclerosis, ischemic vascular disease, ischemic heart disease, myocardial ischemia, myocardial infarction, heart failure, myocardial dysfunction, myocardial remodeling, cardiomyopathies, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, critical leg ischemia, lower extremity ischemia, cerebral ischemia, cerebro vascular disease, retinopathy, retinal repair, remodeling disorder, von Hippel-Lindau syndrome, diabetes, hereditary hemorrhagic telengiectasia, ischemic vascular disease, Buerger's disease and ischemia associated with neurodegenerative disease such as Parkinson's and Alzheimer's disease.

According to a further aspect of the present invention there is provided a method of treating a pathology characterized by insufficient angiogenesis in a tissue of a subject, the method comprising administering to the subject a therapeutically effective amount of at least one peptide of the invention, to thereby treat the pathology characterized by insufficient angiogenesis in the tissue of the subject.

According to yet a further aspect of the present invention there is provided use of at least one peptide of the invention for the manufacturing of a medicament identified for treating a pathology characterized by insufficient angiogenesis in a tissue of a subject.

According to still a further aspect of the present invention there is provided a composition for targeting an agent to endothelial cells, the composition comprising the agent attached to a peptide of the invention.

According to still a further aspect of the present invention there is provided a pharmaceutical composition comprising as an active ingredient the composition of the invention and a pharmaceutically acceptable carrier or diluent.

According to still a further aspect of the present invention there is provided a method of treating a pathology characterized by abnormally increased angiogenesis, comprising administering to a subject in need thereof a therapeutically effective amount of the composition of the invention, thereby treating the pathology characterized by the abnormally increased angiogenesis.

According to still a further aspect of the present invention there is provided use of the composition of the invention for the manufacturing of a medicament identified for the treatment of a pathology characterized by abnormally increased angiogenesis.

According to still a further aspect of the present invention there is provided a method of identifying a putative angiogenic molecule, the method comprising: (a) providing endothelial cells having the peptide of the invention bound thereto, and (b) identifying a molecule capable of displacing the peptide from the endothelial cells, to thereby identify a putative angiogenic molecule.

According to still a further aspect of the present invention there is provided a method of identifying a putative angiogenic molecule, the method comprising: (a) incubating the peptide of the invention with a glucose-regulated protein (GRP78) or cells expressing the GRP78 under conditions suitable for formation of a complex between the peptide and the GRP78 or the cells expressing GRP78, and (b) identifying a molecule capable of displacing the peptide from the complex, to thereby identify a putative angiogenic molecule.

According to further features in the embodiments of the invention described below, the amino acid sequence is HWRRP (SEQ ID NO:7) or HWRRA (SEQ ID NO:8).

According to still further features in the described embodiments the amino acid sequence is set forth by SEQ ID NO:2.

According to still further features in the described embodiments the amino acid sequence is set forth by SEQ ID NO:3.

According to still further features in the described embodiments the amino acid sequence is set forth by SEQ ID NO:4.

According to still further features in the described embodiments the peptide is a linear peptide.

According to still further features in the described embodiments the peptide is a cyclic peptide.

According to still further features in the described embodiments the peptide consists of 12 or less amino acids.

According to still further features in the described embodiments the pathology characterized by insufficient angiogenesis in the tissue of the subject is selected from the group consisting of delayed wound-healing, delayed ulcer healing, reproduction associated disorder, arteriosclerosis, ischemic vascular disease, ischemic heart disease, myocardial ischemia, myocardial infarction, heart failure, myocardial dysfunction, myocardial remodeling, cardiomyopathies, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, critical leg ischemia, lower extremity ischemia, cerebral ischemia, cerebro vascular disease, retinopathy, retinal repair, remodeling disorder, von Hippel-Lindau syndrome, diabetes, hereditary hemorrhagic telengiectasia, ischemic vascular disease, Buerger's disease and ischemia associated with neurodegenerative disease such as Parkinson's and Alzheimer's disease.

According to still further features in the described embodiments the method or the use of the invention is for treating a pathology selected from the group consisting of delayed wound-healing, delayed ulcer healing, reproduction associated disorder, arteriosclerosis, ischemic vascular disease, ischemic heart disease, myocardial ischemia, myocardial infarction, heart failure, myocardial dysfunction, myocardial remodeling, cardiomyopathies, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, critical leg ischemia, lower extremity ischemia, cerebral ischemia, cerebro vascular disease, retinopathy, retinal repair, remodeling disorder, von Hippel-Lindau syndrome, diabetes, hereditary hemorrhagic telengiectasia, ischemic vascular disease, Buerger's disease and ischemia associated with neurodegenerative disease such as Parkinson's and Alzheimer's disease.

According to still further features in the described embodiments the peptide is capable of binding a glucose-regulated protein (GRP78) as set forth by SEQ ID NO:9 on endothelial cells of the tissue.

According to still further features in the described embodiments the binding of the peptide to the glucose-regulated protein (GRP78) as set forth by SEQ ID NO:9 is capable of inducing angiogenesis.

According to still further features in the described embodiments the agent is selected from the group consisting of a toxin, a chemotherapeutic agent and a radioisotope.

According to still further features in the described embodiments the pathology is selected from the group consisting of cancer, metastatic cancer, myelodysplasia, Systemic mastocytosis (SM), retinal neovascularization, neovascularization in atherosclerotic plaques, hemangiomas, arthritis and psoriasis.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the biotechnology art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the embodiments of the invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 1, 2A:
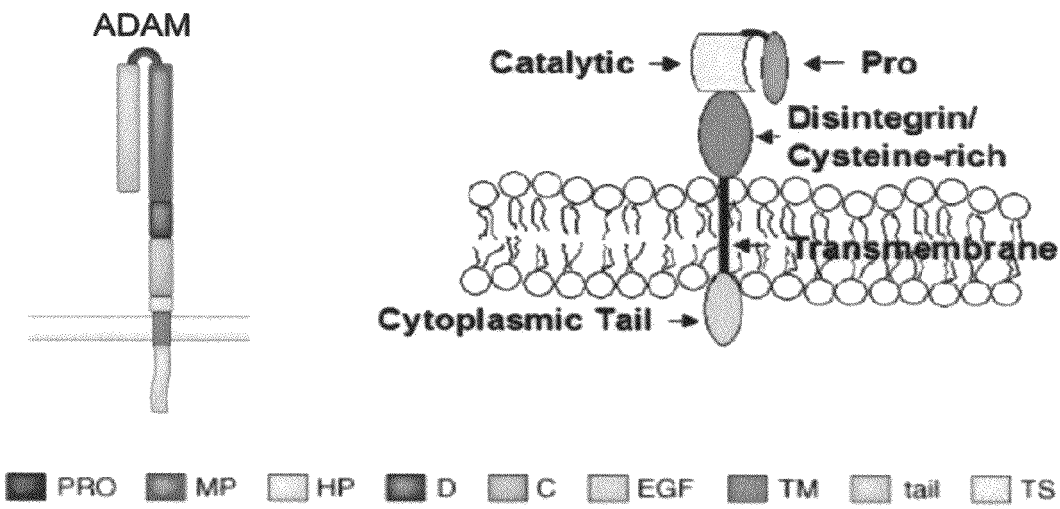

FIG. 1 is a schematic illustration depicting the domain structure of ADAM family members which is represented by the ADAM15 molecule. ADAM proteins typically contain a pro domain (PRO), a metalloprotease domain (MP) and disintegrin domains (D) which include the tripeptide RGD motif that is also found in extracellular matrix (ECM) proteins and which determines specificity and affinity of the ADAMs to distinct integrins. The ADAM proteins also include cysteine rich (C) region, an EGF like domain and a transmembrane segment (TM, in black), along with a cytoplasmic tail (tail). Upon removal of the pro domain, the metalloproteinase domain is activated. The Pro domain keeps the enzyme in an inactive state. Pro domain removal occurs either through the action of pro-hormone convertases or by autocatalysis.

FIGS. 2a-b depict the ADAM15 protein domains (FIG. 2a) and amino acid sequence (FIG. 2b). FIG. 2a—the amino acid positions of the ADAM15 protein domains refer to the polypeptide set forth by SEQ ID NO:1 (GenBank Accession No. Q13444); FIG. 2b—amino acid sequence of the ADAM15 protein. Bolded text refers to the metalloprotease domain, disintegrin like domain and EGF like domain. The underlined text corresponding to amino acids 286-297 refers to the ADOPep1 peptide being only in the metaloprotease domain but not in the disintegrin like domain or the EGF like domain.

Figure 3:
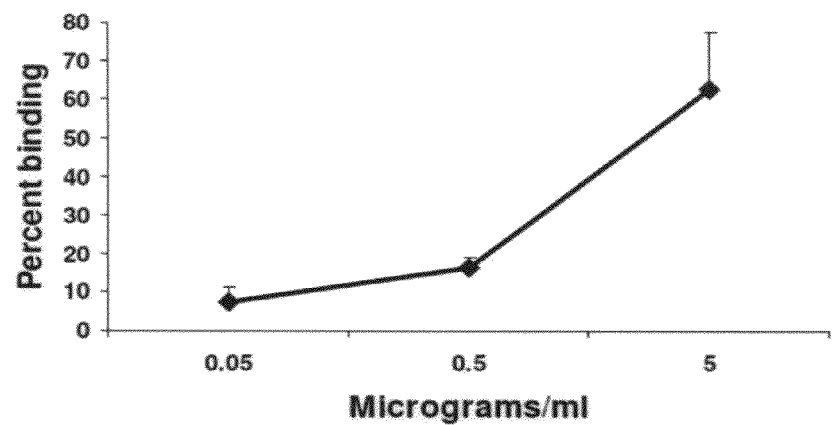

FIG. 3 is a FACS analysis depicting the binding (in percentages) of biotinylated ADOPep1 (ADOPep1$^{Biot}$), an ADAM15 derived peptide (SEQ ID NO:2), to endothelial cells (EC) under normoxia. Biotinylated ADOPep1 at 0.05, 0.5 and 5 microgram/ml (µg/ml) were added to endothelial cells. Note the increase in binding of ADOPep1 to endothelial cells which reached about 62% in a dose dependent manner and was maximal at 5 µg/ml.

Figure 4:
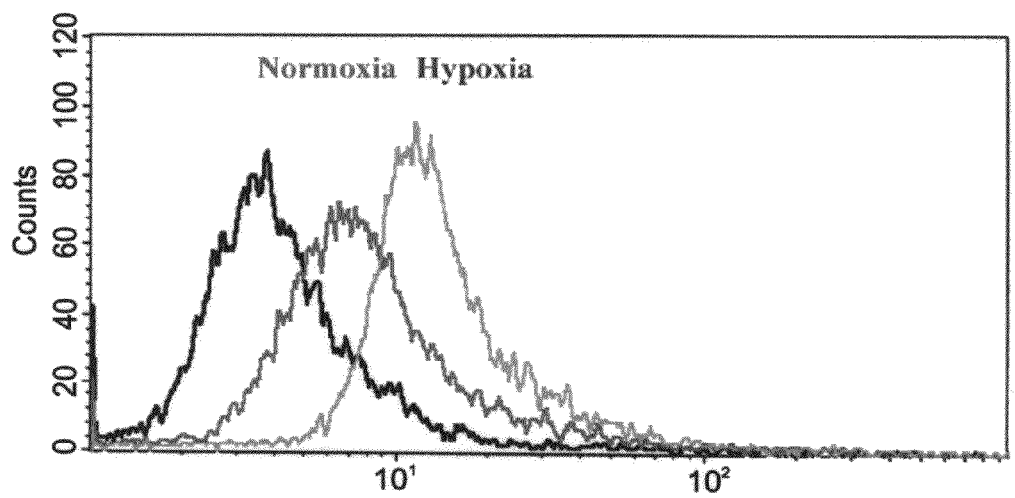

FIG. 4 is a FACS analysis depicting the binding (in total counts) of Biotinylated ADOPep1 to endothelial cells under normoxia and hypoxia conditions. Note that the binding of ADOPep1 added at 5 micrograms per 100,000 cells to endothelial cells increased under hypoxia. X axis—Intensity of binding.

Figure 5:
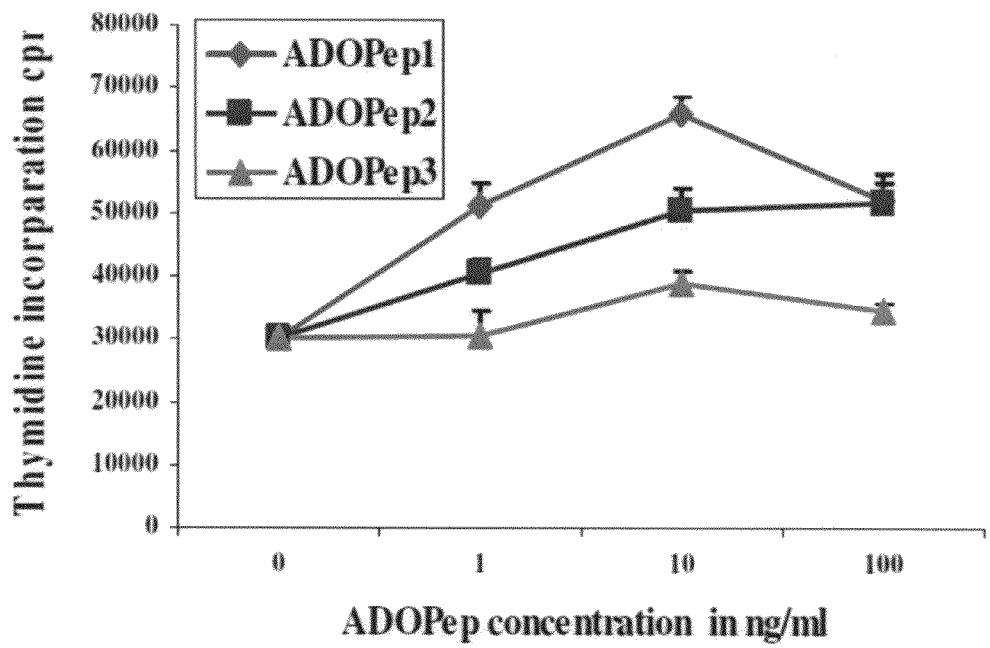

FIG. 5 is a graph depicting cell proliferation as a function of ADOPeps' concentration. Proliferation of endothelial cells (EC) under hypoxia conditions was measured by [$H^3$]Thymidine incorporation. Endothelial cells (12,000/well) in minimal growth medium were incubated for 24 hours in the presence of 1, 10 and 100 ng/ml of ADOPep1 (SEQ ID NO:2; red diamonds), 2 (SEQ ID NO:3; blue squares) and 3 (SEQ ID NO:4; green triangles) peptides. Note that ADOpep1 induced proliferation of endothelial cells under hypoxia conditions at a concentration of 10 ng/ml.

Figure 6:
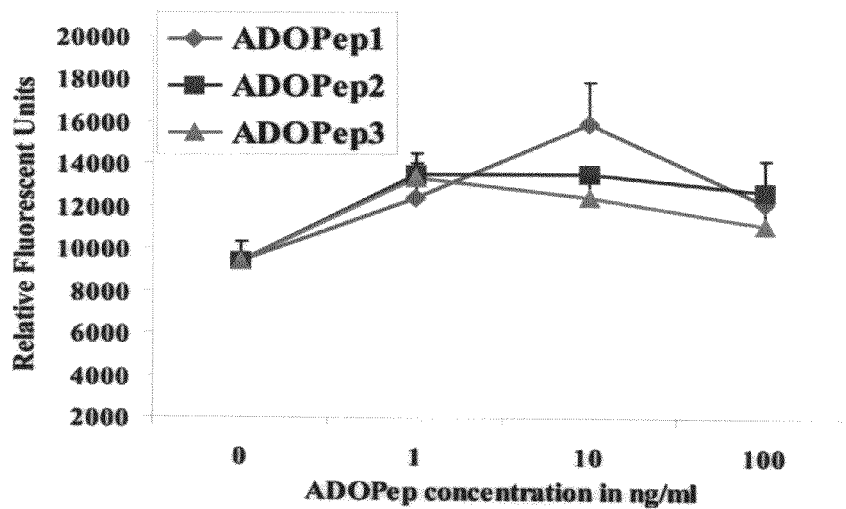

FIG. 6 is a graph depicting migration of endothelial cells under hypoxia conditions. Endothelial cells (25,000) were incubated in endothelial cells growth medium free supplements in the migration chamber. ADOPep1 (SEQ ID NO:2), 2 (SEQ ID NO:3) and 3 (SEQ ID NO:4) were added to the feeder tray of the migratory kit at 1, 10 and 100 ng/ml for 5 hours hypoxia. Results were determined by a fluorescence ELISA reader and expressed as increase in percentage migration in Relative fluorescence Units. Note that ADOPep 1 induced increase in percent of migration at 10 ng/ml.

Figure 7:
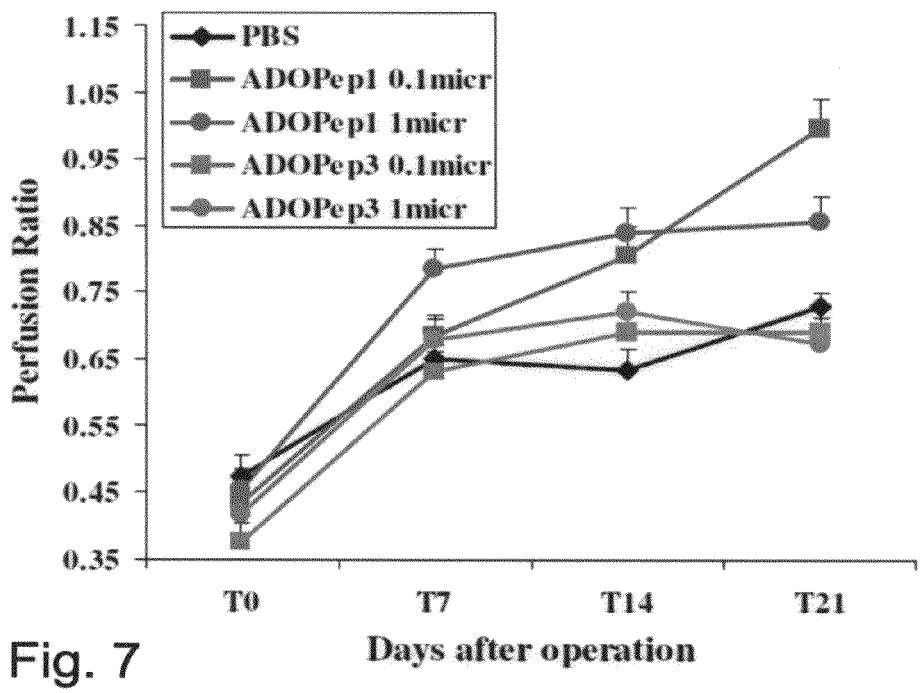

FIG. 7 is a graph depicting blood perfusion determined in a mouse ischemic hind limb model by laser Doppler blood flow analyzer and demonstrating the in vivo activity of ADOPeps on restoration of blood perfusion in ischemic mouse hind limb. A mouse hind limb model was created by excision of femoral artery of C57Bl mouse hind limb, the non-operated limb served as a control. ADOPep1 (SEQ ID NO:2; red symbols) and 3 (SEQ ID NO:4; green symbols) were injected intra-muscularly one day after surgery at 0.1 (squares) and 1 (circles) micrograms/mouse. Injection of PBS (black diamond) was used as a control. Blood flow was measured using a laser Doppler immediately (T0) or at 7 (T7), 14 (T14) and 21 (T21) days after surgery. The average perfusion of each limb was determined and the perfusion ratio [expressed as Relative Perfusion (ischemic left/control right leg)] was plotted against time. Note the significant increase in blood perfusion ($p<0.05$) in limb of mice treated with ADOPep1 at 0.1 microgram on day 21 after surgery.

Figure 8:
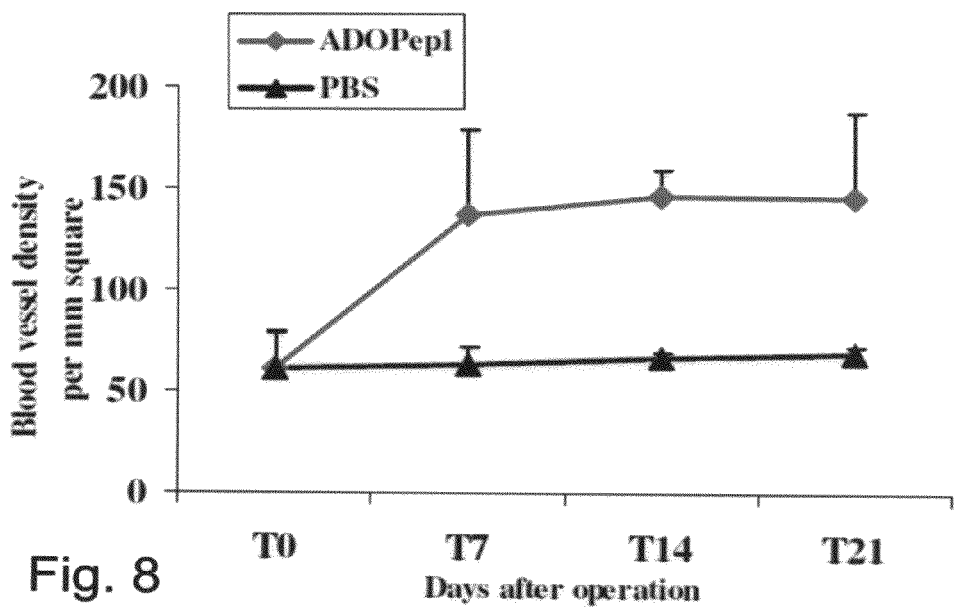

FIG. 8 is a graph depicting histological assessment of angiogenesis in the ischemic hind limb treated with ADOPep1. Mice were subjected to hind limb ligation and ADOPep administration as described in FIG. 7 and at the noted days (0, 7, 14 and 21 days) post hind limb ligation the mice were sacrificed and legs were embedded in paraffin. Sections were stained with anti von Willebrand factor and the number of Factor VIII positive vessels was determined using the Image Pro Plus software. Shown are the average blood vessel densities (of 10 individual microscopical fields per sample) expressed as number of capillaries per millimeter squared in histological sections of mouse hind limb ischemia treated with ADOPep1. Note the significant increase in the blood vessel density of ischemic hind limb following injection of the ADOPep1.

Figures 9A, 9B:
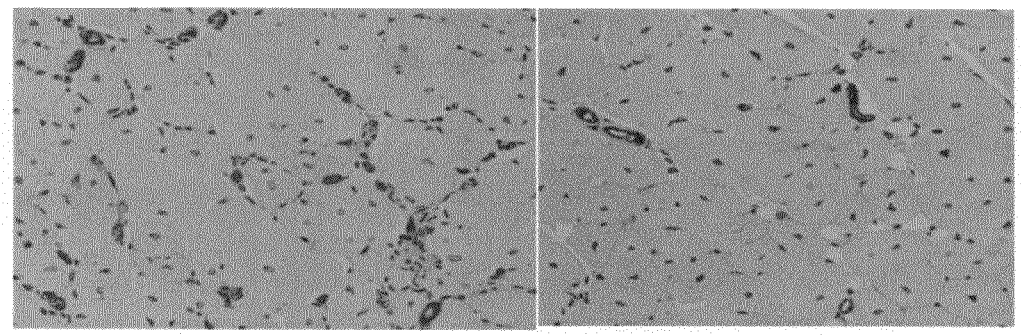

FIGS. 9a-b are microscopical images of histological sections subjected to von Willebrand Factor immuno-staining of mouse hind limb ischemia 21 days following injection of ADOPep1 (FIG. 9a) or PBS (FIG. 9b). Note the significantly higher von Willebrand Factor staining of small vessels in the ADOPep1 treated group (FIG. 9a) as compared to the control (FIG. 9b). Magnification ×200.

Figures 10A, 10B:
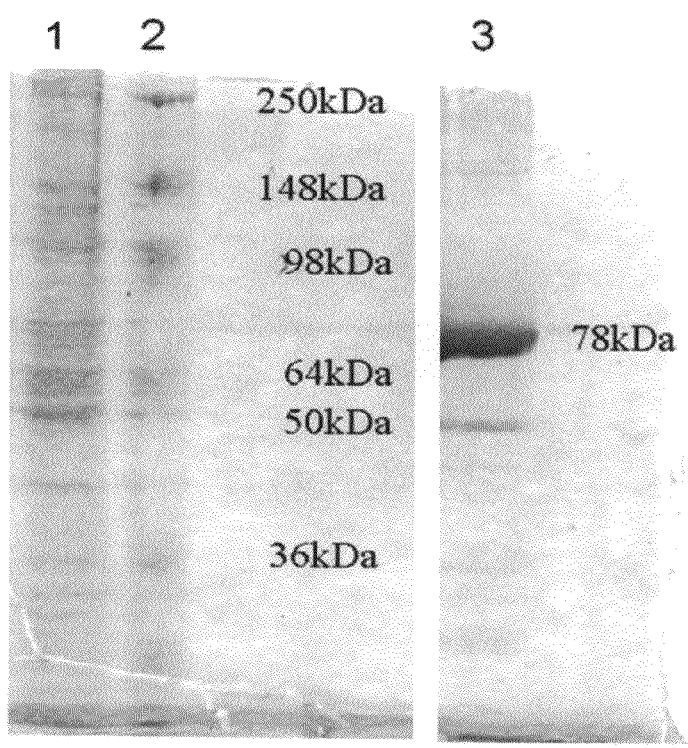

FIGS. 10a-b are images of Coomassie blue staining of polyacrylamide gel electrophoresis (PAGE) of endothelial cell lysates obtained from cells under hypoxia and analyzed before (FIG. 10a) and after (FIG. 10b) immunoprecipitation (IP) of the cells with biotinylated ADOPep1. FIG. 10a—lane 1—endothelial cell lysate before IP; lane 2—molecular weight markers; FIG. 10b—lane 3—IP endothelial cell lysate with ADOPep1. Note the major single protein band of 78 kDa following IP with biotinylated ADOPep1.

FIG. 11 is a Western Blot analysis of immune precipitation of endothelial cells lysate with biotinylated ADOPep1 under normoxia and hypoxia conditions. Staining of the nitrocellulose membrane with biotinylated ADOPep1 followed by Chemiluminescent Substrate revealed a band at 78 kDa which was further identified by Mass spectrometry as GRP78 protein (GenBank Accession No. CAB71335; SEQ ID NO:9). Lane 1—IP of endothelial cells lysate under normoxia with biotinylated ADOPep1; lane 2—IP of endothelial cells lysate under hypoxia with biotinylated ADOPep1.

FIG. 12 is Western Blot analysis of immune precipitation of endothelial cells lysate under hypoxia and normoxia with biotinylated ADOPep1. Staining of the nitrocellulose membrane with anti GRP78 antibody (Santa Cruz Biotechnologies, CA, USA) followed by Chemiluminescent Substrate confirmed the identity of the GRP78 protein in the major 78 kDa protein band. Lane 1—IP of endothelial cells lysate under hypoxia with biotinylated ADOPep1; lane 2—IP of endothelial cells lysate under normoxia with biotinylated ADOPep1.

Figures 13A, 13B:
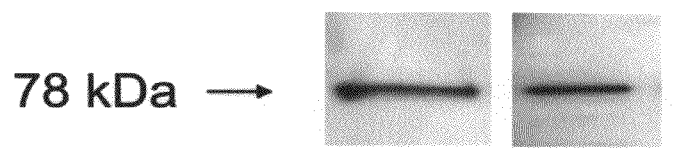

FIGS. 13a-b are Western blot analyses of immune precipitation of endothelial cells lysate under hypoxia with biotinylated ADOPep1. Staining of the nitrocellulose membrane was performed with Biotinylated ADOPep1 (FIG. 13a) or anti GRP78 antibody (FIG. 13b) followed by Chemiluminescent Substrate and confirmed the presence of GRP78 protein.

Figure 14:
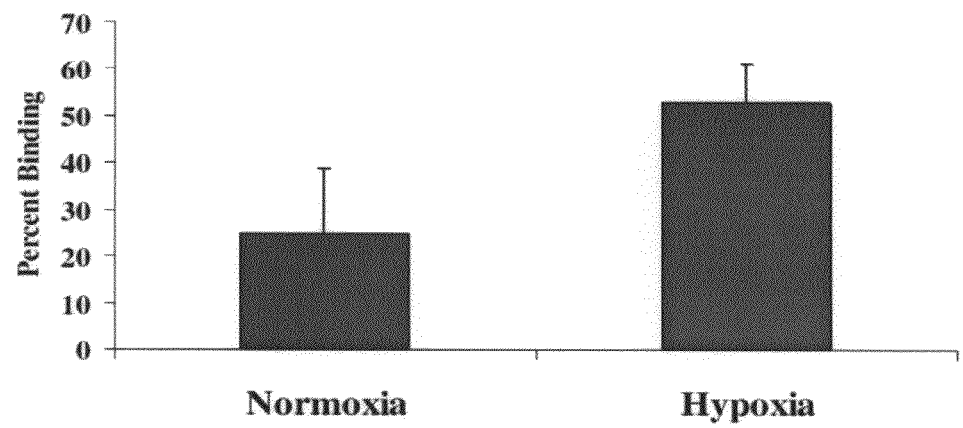

FIG. 14 is a bar graph depicting the results of FACS analysis of endothelial cells under normoxia and hypoxia conditions using anti-GRP78 antibody. The anti-GRP78 antibody was added to endothelial cells originating from 10 different cords and the binding of the antibody to the cells was determined by FACS analysis. Note the increase in percent binding of anti-GRP78 antibody to endothelial cells under hypoxia conditions.

Figure 15:
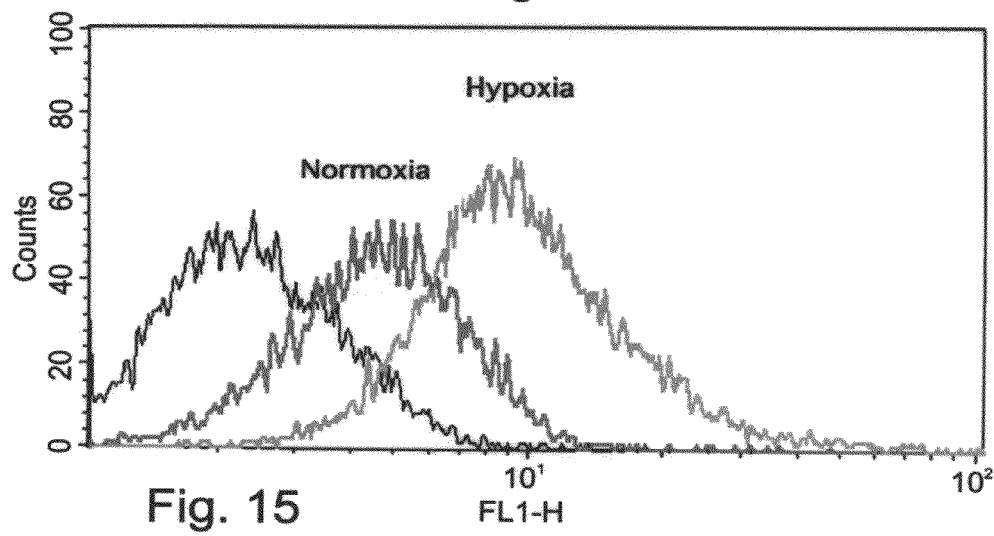
Figure 16B:
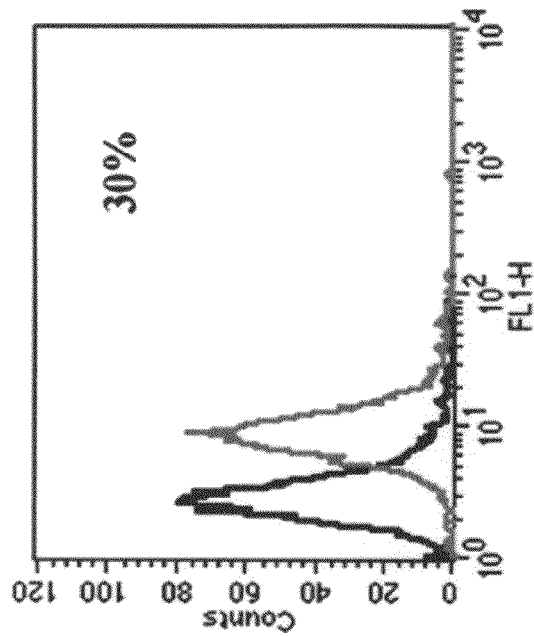
Figure 16A:
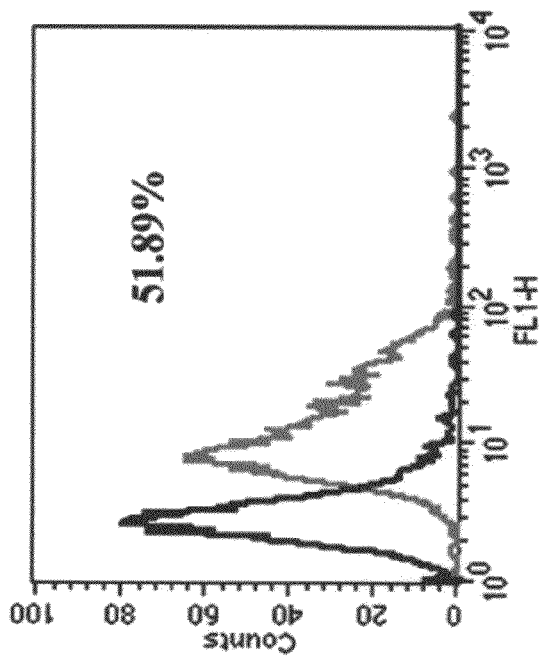
Figure 16D:
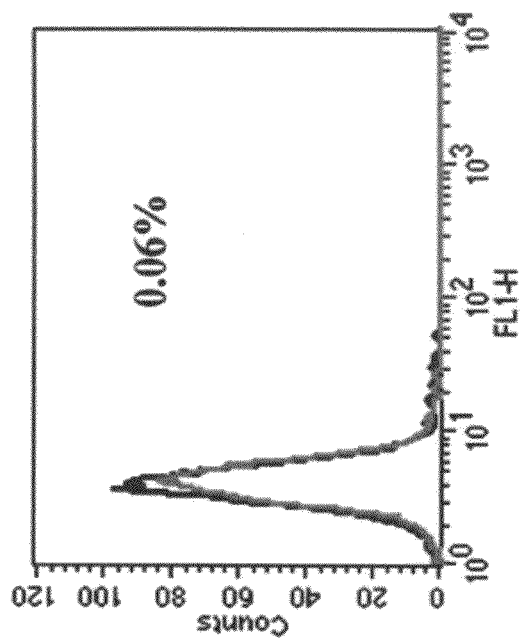
Figure 16C:
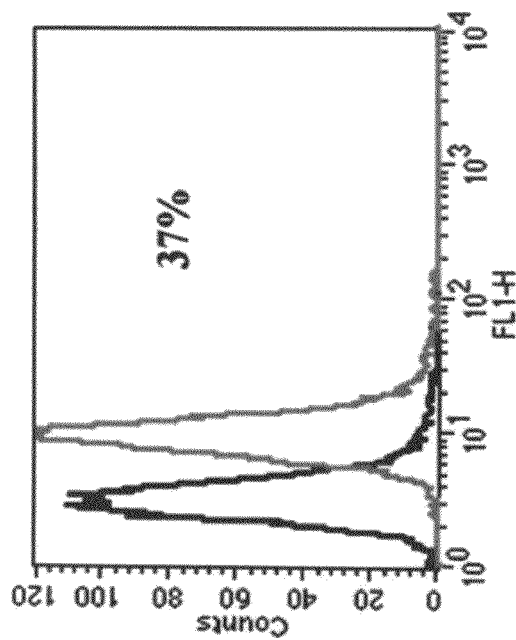

FIG. 15 is a FACS histogram depicting the binding of Biotinylated ADOPep1 to endothelial cells under normoxia and hypoxia conditions. X axis—Intensity of binding. Binding of ADOPep$^{Biot}$ added at 5 micrograms per 100,000 cells to endothelial cells increased under hypoxia.

FIGS. 16a-d are FACS analyses of different tumor cell lines using the anti-GRP78 antibody. Anti-GRP78 antibody was added to MCF7 breast carcinoma (FIG. 16a), HT-29 colon carcinoma (FIG. 16b), SK-28 melanoma (FIG. 16c) and K562 erytroblastoma (FIG. 16d) and the binding to the cells was detected using FACS analysis. Note the increase in percent binding of anti-GRP78 antibody to MCF7, HT29 and SK-28 cell lines. Also note that anti-GRP78 antibody did not bind to the membrane of K562 cells.

Figure 17:
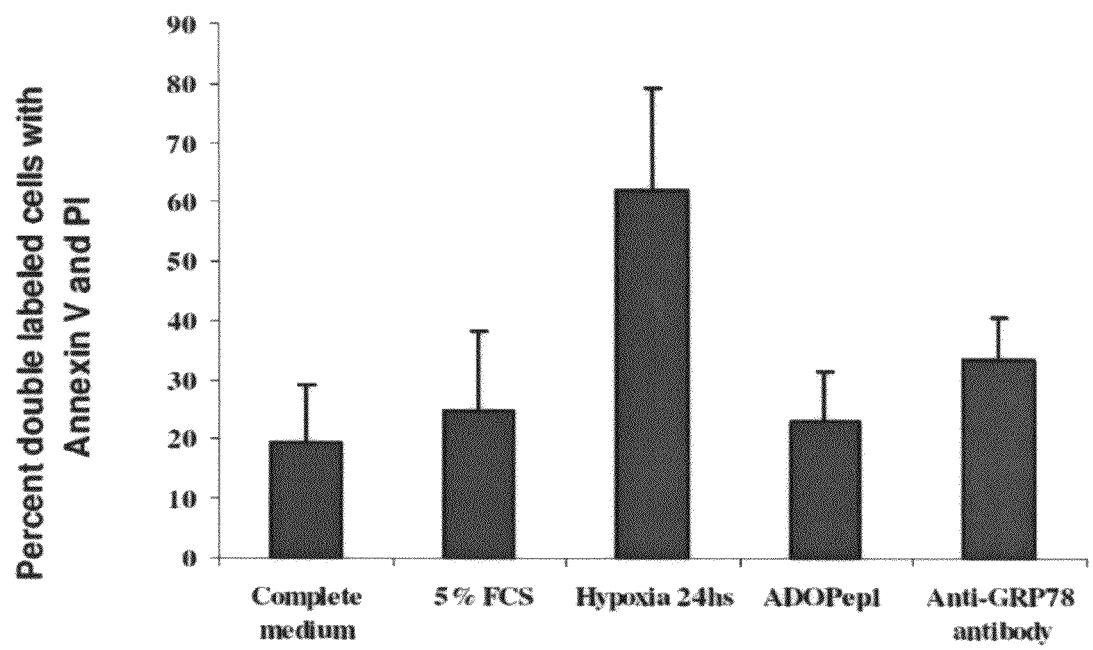

FIG. 17 is a histogram depicting the effect of ADOPep1 on hypoxia-induced apoptosis of endothelial cells. Endothelial cells were exposed for 24 hours hypoxia in the presence of endothelial cell growth medium supplemented with 5% fetal calf serum (FCS), followed by incubation under hypoxia conditions with ADOPep1 (10 ng/ml) or anti-GRP78 antibody (100 ng/ml). Cells (100,000/tube) were incubated with Annexin-V FITC/PI for endothelial cell apoptosis determination. Percent apoptosis of endothelial cells stained with Annexin-V/PI demonstrate that hypoxia conditions induce 60% apoptosis whereas addition of ADOPep1 reduced hypoxia-induced apoptosis to 25%. Similarly, anti-GRP78 antibody induced a reduction in apoptosis up to 32%.

Figures 18A, 18B:
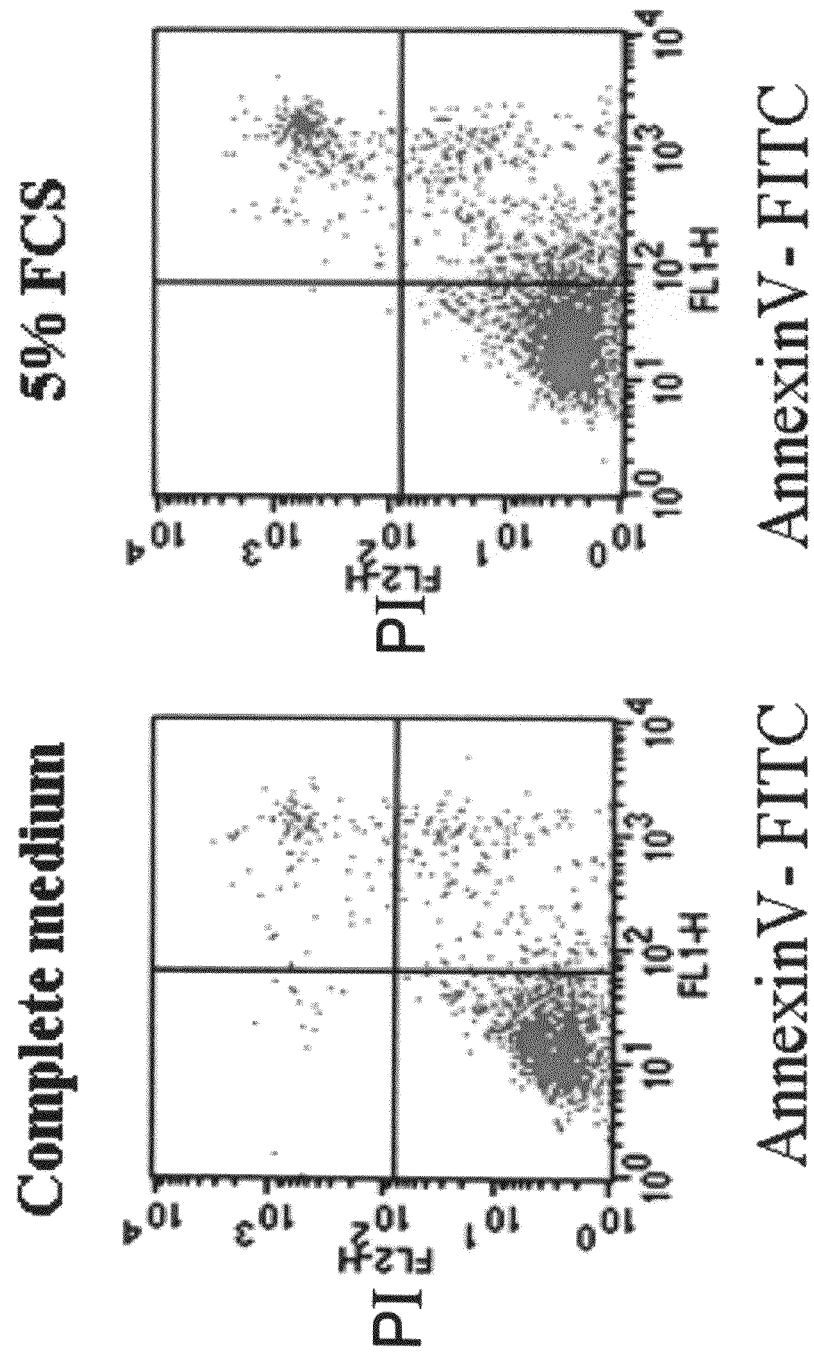
Figure 18C:
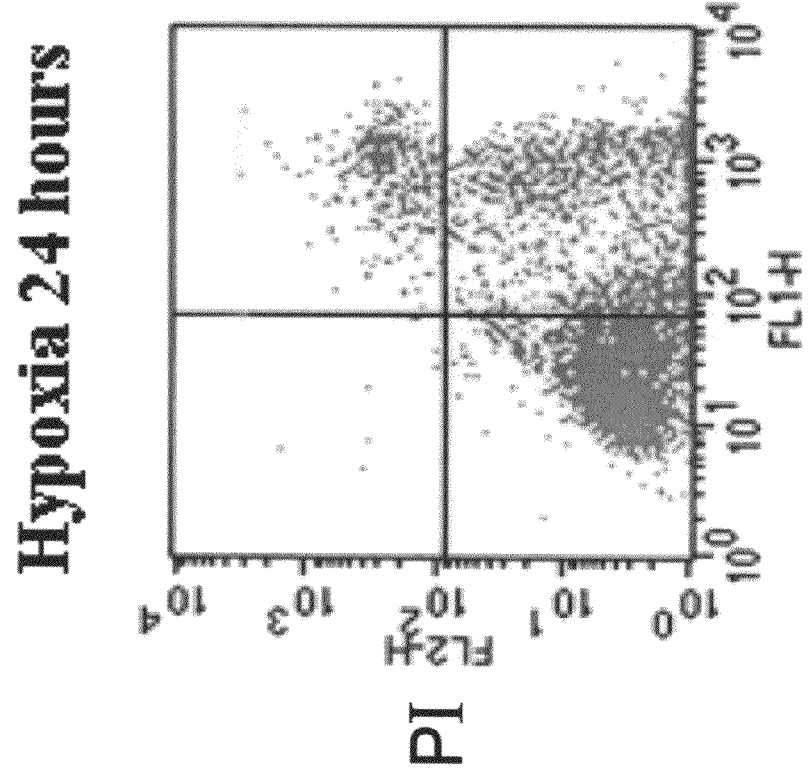
Figures 18D, 18E:
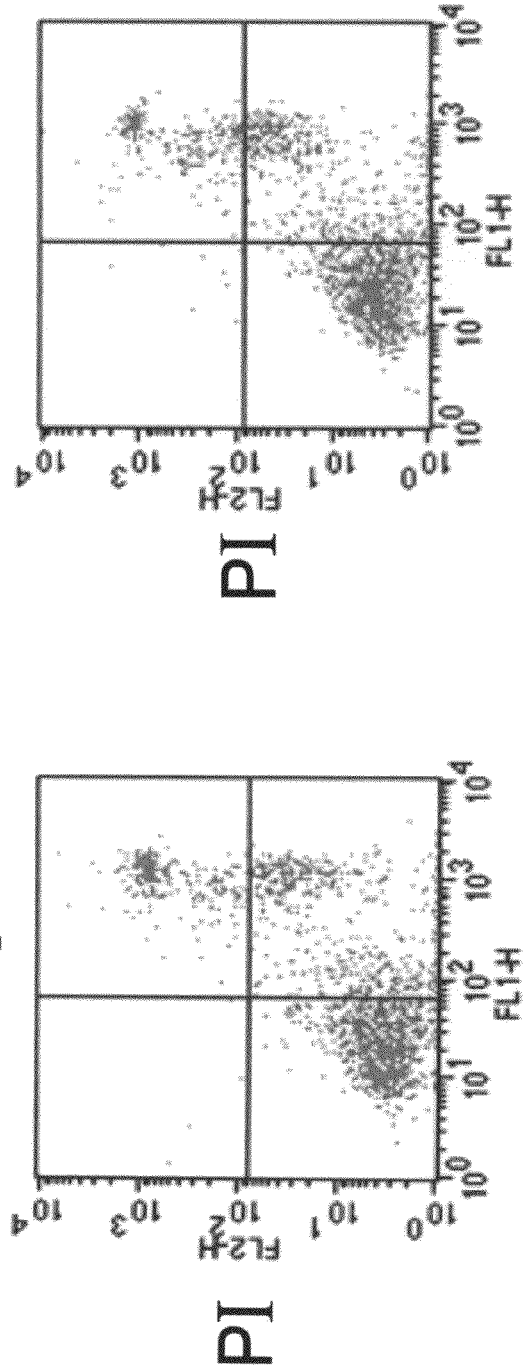

FIGS. 18a-e are dot plot FACS analyses depicting the inhibition of apoptosis by the ADOPep1. Endothelial cells under hypoxia were stained with both Annexin V (shown on the X axis) and Propidium Iodide (shown on the Y axis)

apoptotic markers. Cells were incubated with complete medium under normoxia (FIG. 18a), in the presence of 5% FCS and complete medium under normoxia (FIG. 18b), in starvation medium under hypoxia for 24 hours (FIG. 18c), in starvation medium under hypoxia for 24 hours and in the presence of ADOPep1 (FIG. 18d) or in starvation medium under hypoxia for 24 hours and in the presence of anti-GRP78 antibody (FIG. 18e). Note that incubation with peptide ADOPep1 induced a remarkable decrease in the stained cells (FIG. 18d), demonstrating its feasibility to reduce hypoxia-induced apoptosis.

Figure 19:
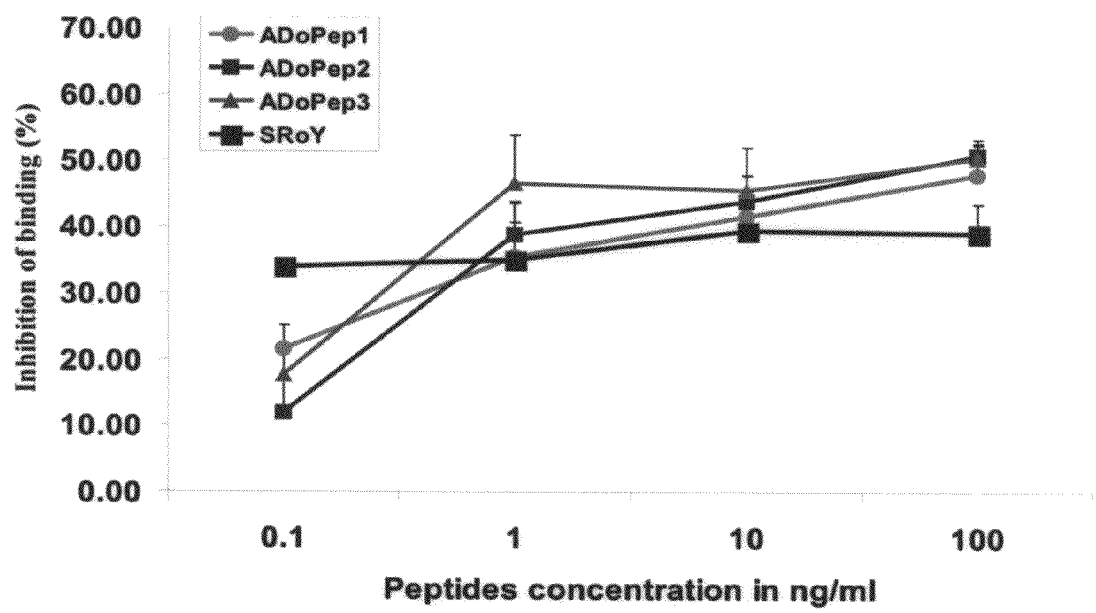

FIG. 19 is a graph depicting inhibition of binding (in percentages) of anti-GRP78 antibody to endothelial cells by increasing concentrations of ADOPep1, 2, and 3 peptides. Endothelial cells were incubated for 2 hours with increasing concentrations of ADOPeps, following which the cells were incubated for another 1 hour with the 2 μg/ml of anti-GRP78 antibody and the amount of bound antibody on EC was detected using an ELISA reader. Note that while increasing concentrations of ADOPep1, 2 or 3 resulted in up to 50% inhibition of binding of the anti-GRP78 antibody to endothelial cells, the sRoY scrambled peptide (SEQ ID NO:10; RYHLIPRGWDHS) exhibited no specific inhibition effect on the binding of anti-GRP78 to endothelial cells.

Figure 20A:
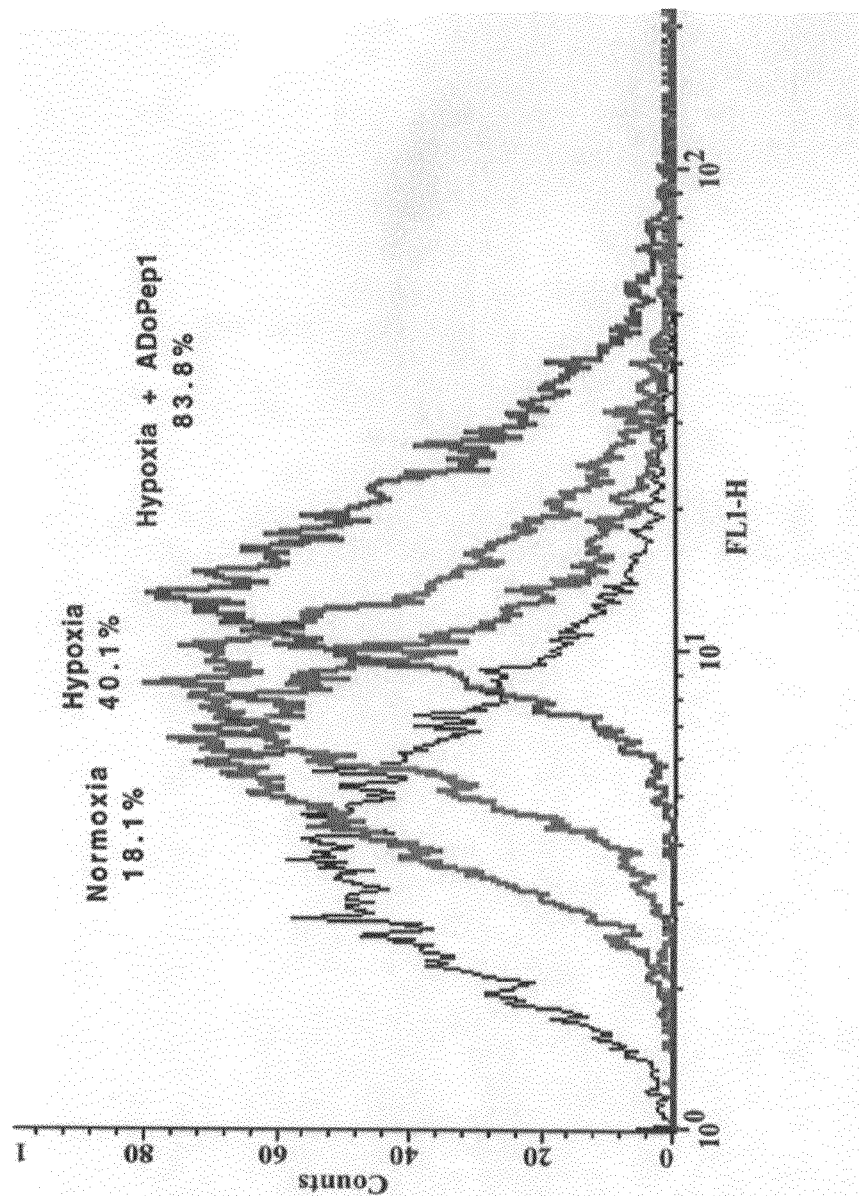

FIGS. 20a-b depict binding of the anti-GRP78 antibody to endothelial cells following incubation of the cells with ADOPep1. Endothelial cells were incubated for 48 hours under either normoxia conditions, or hypoxia for 24 hours followed by normoxia for another 24 hours, in the presence or absence of the ADOPep1 (at a concentration of 10 ng/ml) and the binding to anti-GRP78 antibody was determined using FACS analysis. FIG. 20a—a flow cytometry analysis of endothelial cells under normoxia (green plot), hypoxia (for 24 hours) followed by normoxia (for another 24 hours) in the absence (red plot) or presence (blue plot) of the ADOPep1 peptide. Note that while the binding of anti-GRP78 increased from 18.1% under normoxia to 40.1% under hypoxia, a more significant increase (up to 83.8%) was observed when the cells were incubated in the presence of the ADOPep1 under hypoxia conditions. FIG. 20b—A histogram depicting the percent of anti-GRP78 binding to endothelial cells under normoxia, hypoxia (for 24 hours), normoxia with 10 ng/ml ADOPep1, hypoxia (24 hours) followed by normoxia (24 hours) or hypoxia (24 hours) followed by normoxia (24 hours) in the presence of 10 ng/ml ADOPep1. Results represent average±standard deviations of three independent experiments.

Figure 21:
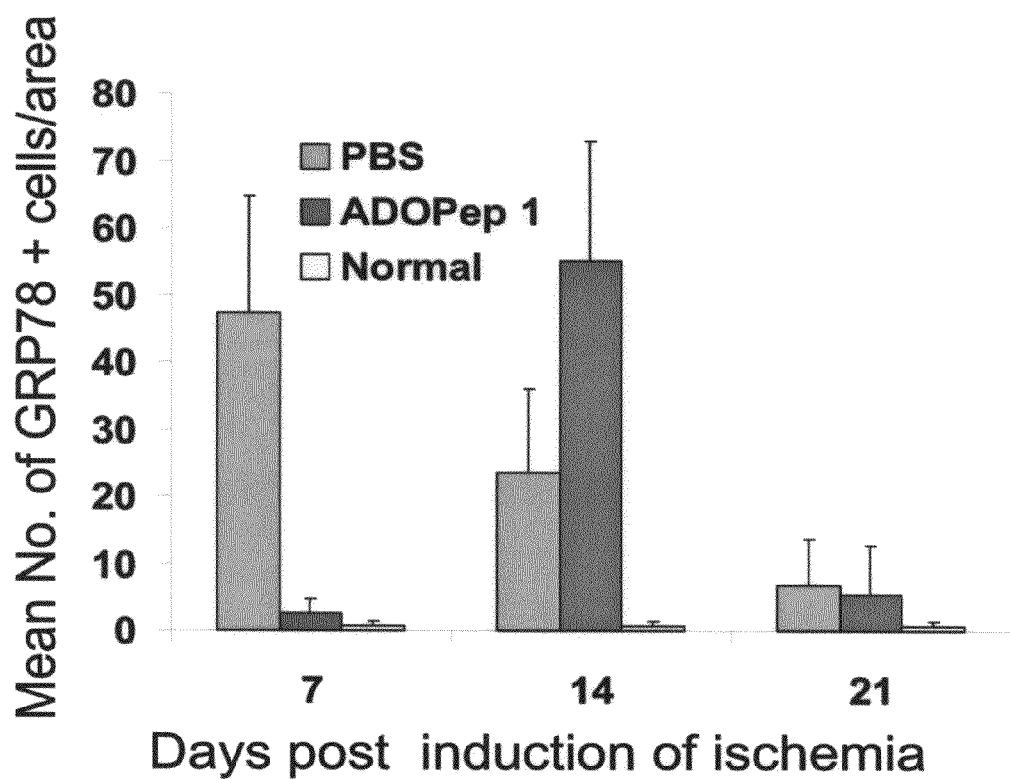

FIG. 21 is a bar graph depicting the mean number of GRP78-positive (GRP78+) cells per area in hind limb ischemia treated with ADOPep1 as a function of the days post induction of ischemia. Mice were subjected to hind limb ligation (the ischemic model) and after one day the mice were injected with either 1 μg/mice of ADOPep1, or 50 μl of PBS as control. The number of GRP78 positive cells was determined in histological sections prepared from ligated hind limbs (injected with ADOPep1 or PBS) of mice sacrificed at 7, 14 or 21 days post ischemia induction or normal untreated (non-ischemic) hind limbs. Note that while the number of GRP78 positive cells decreased in PBS injected hind limbs from day 7 to day 14 and further at day 21 post ligation, the number of GRP78 positive cells significantly increased in hind limbs injected with ADOPep1 from 7 to 14 days post ligation and further decreased at 21 days post ligation.

Figure 22:
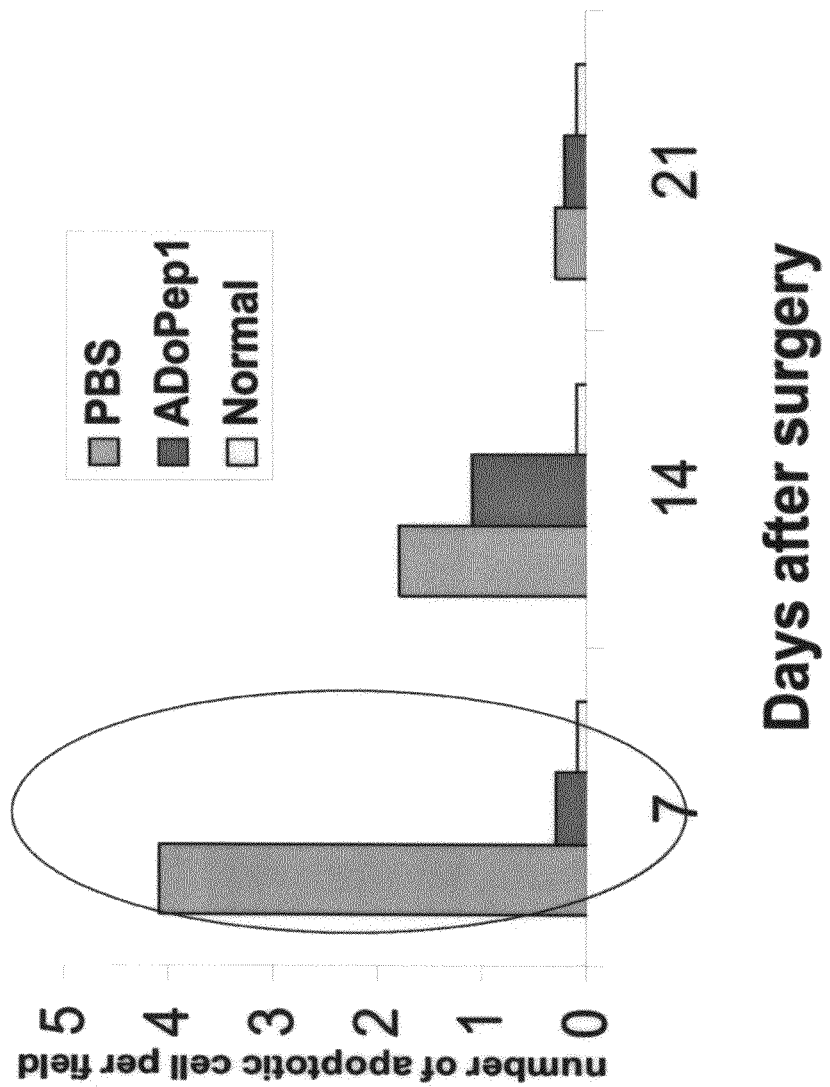

FIG. 22 is a bar graph depicting the number of apoptotic cells per field in ischemic hind limb treated with ADOPep1 as a function of days after ischemia induction. Mice were subjected to hind limb ligation and PBS or ADOpep1 injection as described in the description of FIG. 21, hereinabove, and the number of apoptotic cells per microscopical filed was determined in histological sections prepared from either ligated and ADopep or PBS treated hind limbs of mice sacrificed at 7, 14 or 21 days post ischemia induction or from normal non-ischemic hind limbs. Note the significant decrease (7 days post ligation) in the number of ischemia induced apoptotic cells in ligated hind limbs injected with ADOPep1 as compared to PBS-injected ischemic hind limbs.

Figure 23:
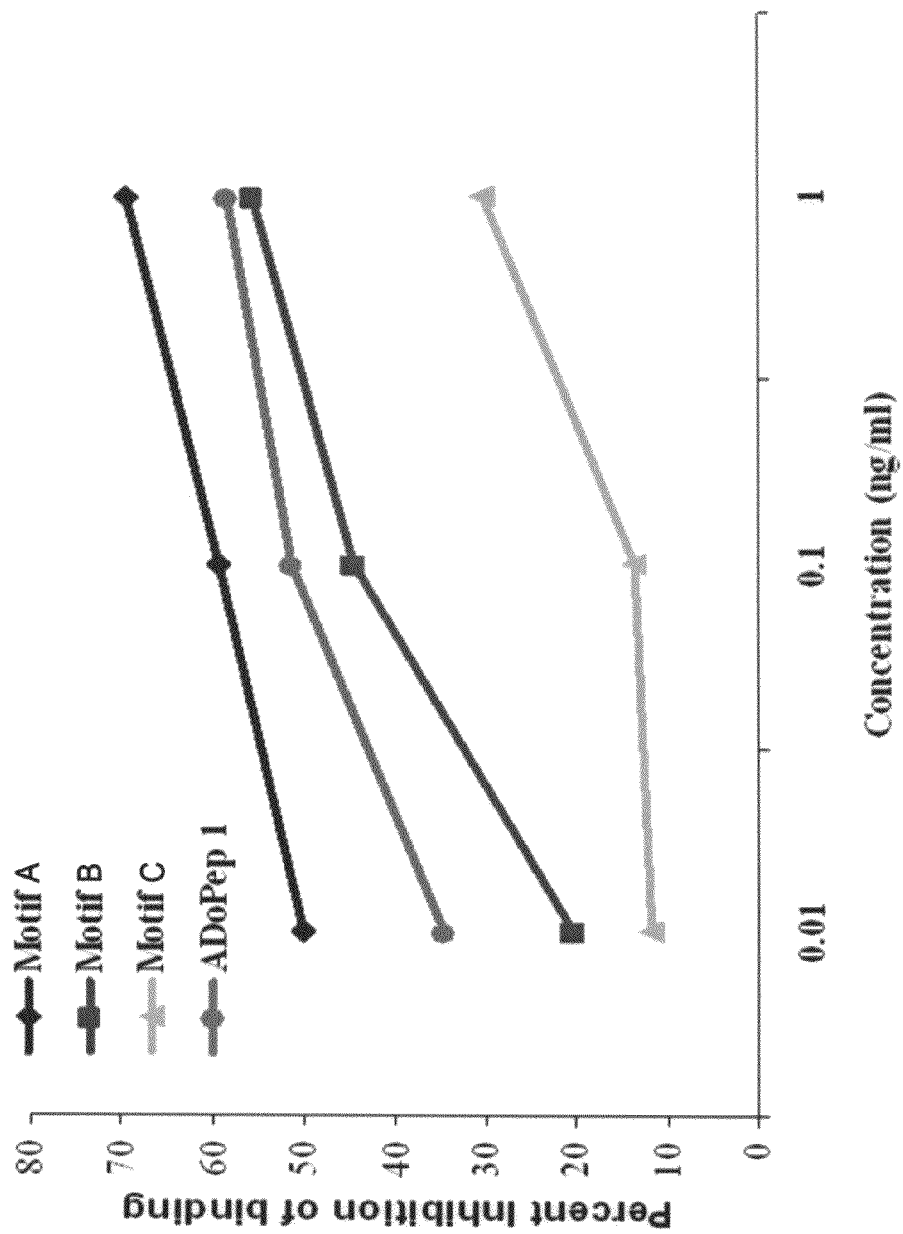
Figures 24A, 24B:
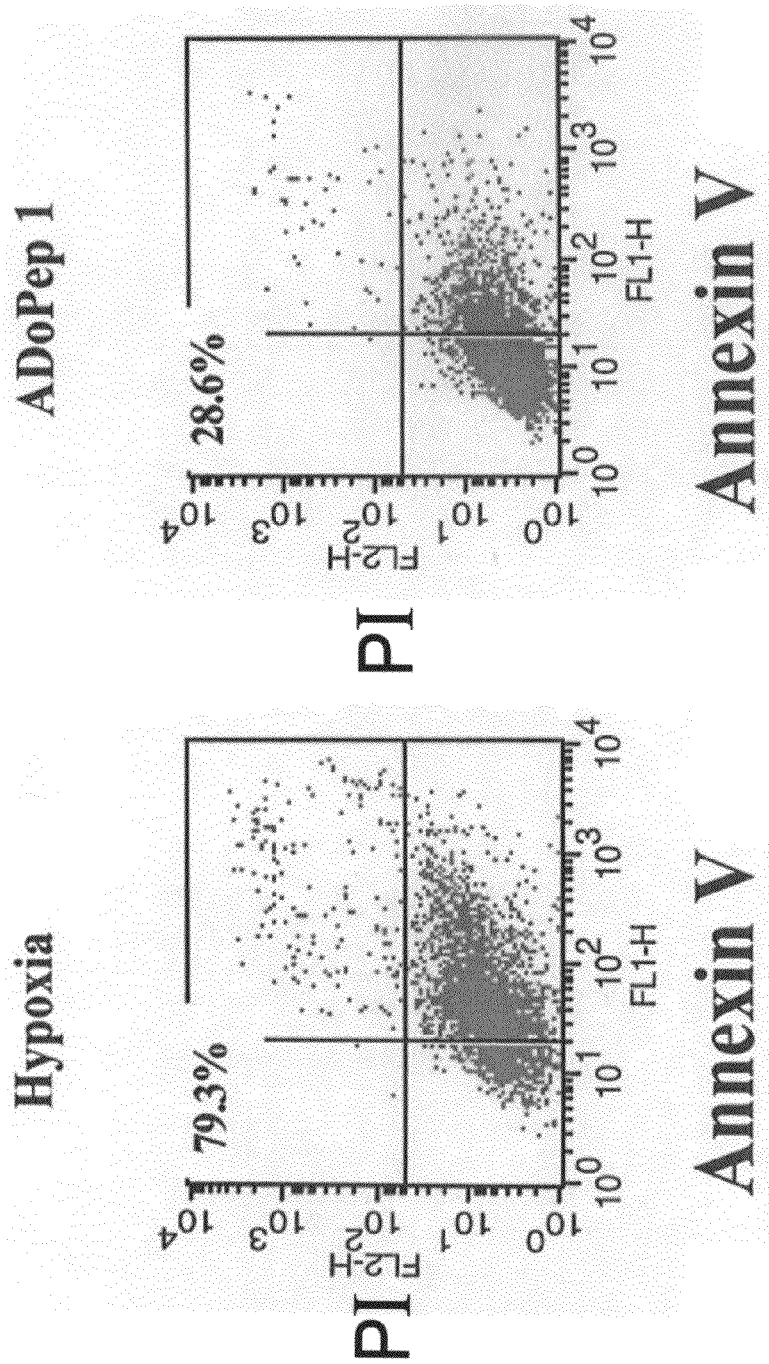
Figures 24C, 24D:
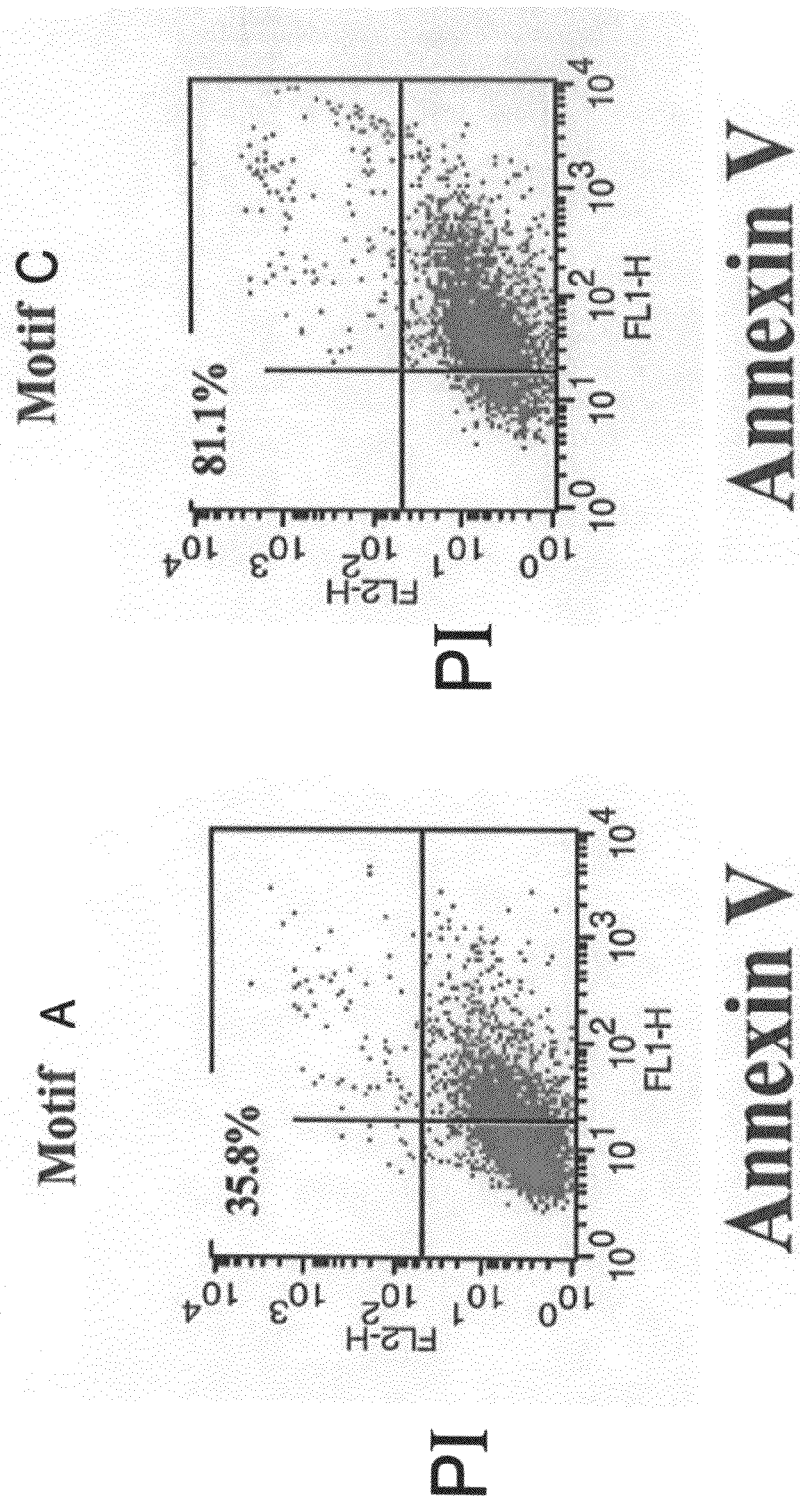

FIG. 23 is a graph depicting the inhibition of binding of ADOPep1$^{Biot}$ (2 μg/ml) to endothelial cells by specific peptides corresponding to conserved motifs from the ADOPeps. Endothelial cells were incubated for 2 hours under normoxia conditions in the presence of increasing concentrations (0.01, 0.1 or 1 ng/ml) of peptides having the amino acid sequences corresponding to Motif A (HWRRP; SEQ ID NO:7), Motif B (HWRRA; SEQ ID NO:8), Motif C (AHLLP; SEQ ID NO:6) or non-biotinylated ADOPep1 (SEQ ID NO:2) and then were incubated for 1 hour with biotinylated ADOPep1 (2 μg/ml) and the binding of biotinylated ADOPep1 to endothelial cells was determined using HRP-streptavidin. Note that the peptides having amino acid sequence corresponding to Motif A and B exhibited a significant inhibition of the binding of ADOPep1$^{Biot}$ to endothelial cells.

FIGS. 24a-d are FACS analyses depicting hypoxia induced apoptosis. Endothelial cells were incubated for 24 hours under hypoxia conditions in the absence (FIG. 24a) or presence of 10 ng/ml of ADOPepe1 (FIG. 24b), peptide of Motif A (FIG. 24c) or peptide of motif C (FIG. 24d) and the level of apoptosis was determined using FACS analysis and the PI (shown on the Y axis)/Annexin V (shown on the X axis) markers. Note that while ADOPep1 and Motif A peptides were capable of inhibiting the hypoxia induced apoptosis from 79.3% under hypoxia to 28.6% (ADOPep1) or 35.8% (Motif A), the motif C peptide exhibited no effect of hypoxia induced apoptosis (81.1%).

Figure 25:
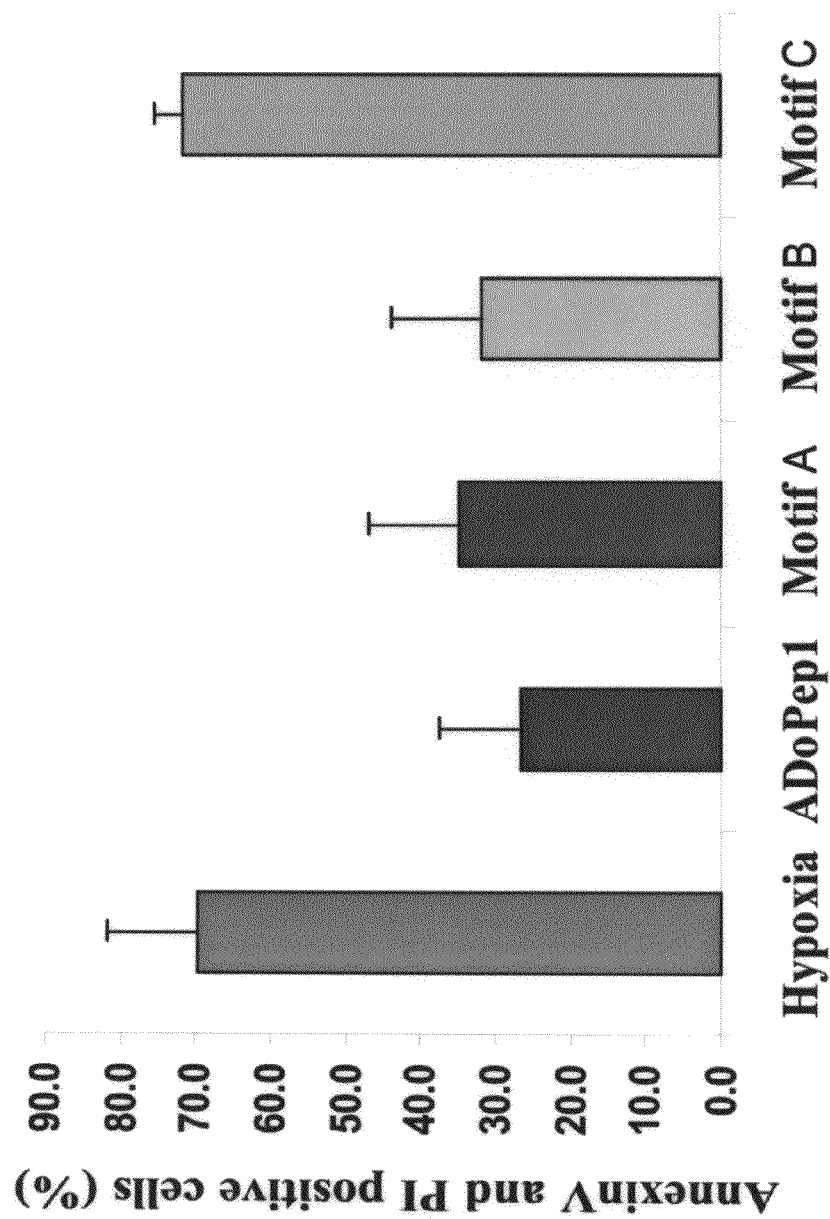

FIG. 25 is a bar graph depicting the inhibition of hypoxia induced apoptosis by ADOPep1, Motif A and Motif B. Endothelial cells were incubated for 24 hours under hypoxia conditions in the absence or presence of 10 ng/ml of ADOPepe1, Motif A, Motif B or motif C and the level of apoptosis was determined using FACS analysis and quantified as the percent of Annexin V and PI positive cells. The results represent average±standard deviation of 4 independent experiments. Note that while ADOPep1 and Motif A and B peptides exhibited a significant inhibition of hypoxia induced apoptosis, the Motif C peptide exhibited no effect on apoptosis.

Figure 26A:
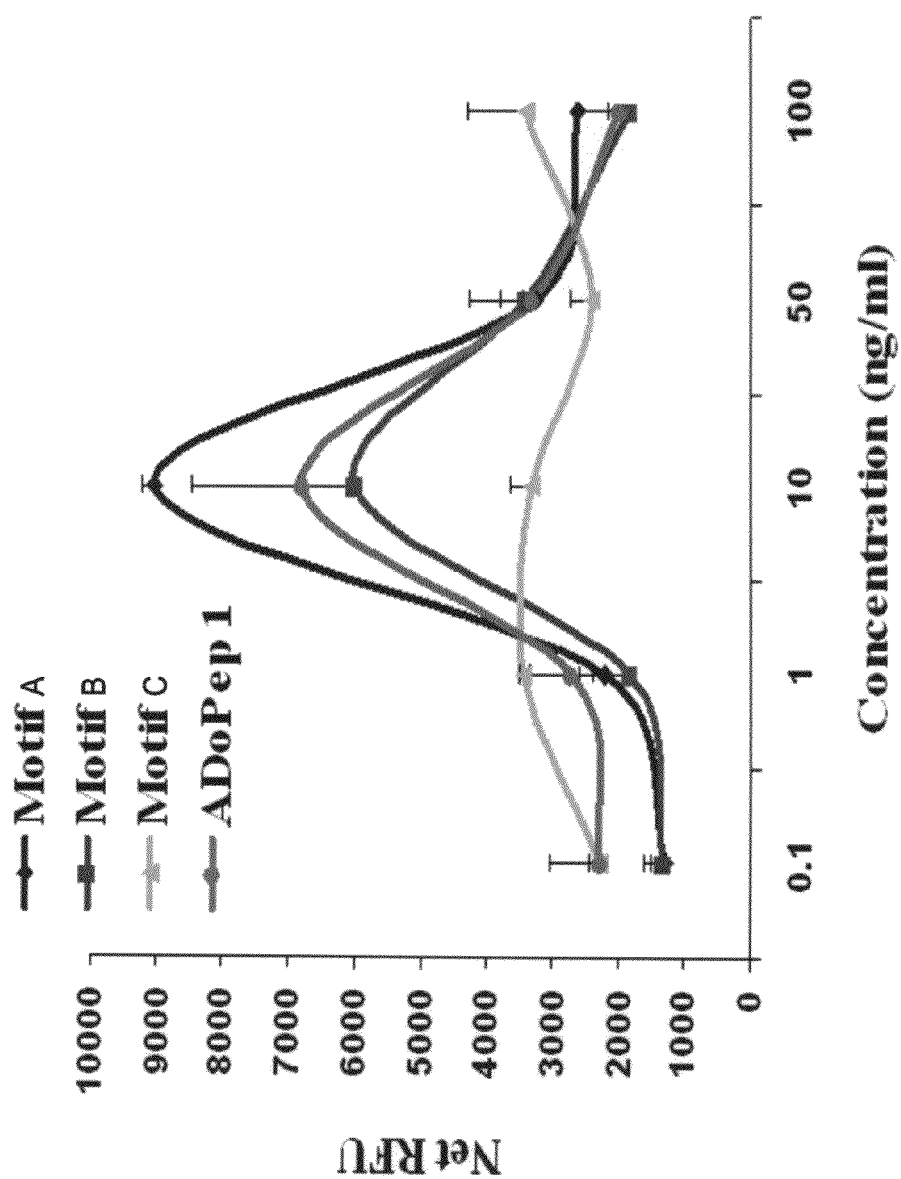
Figure 26B:
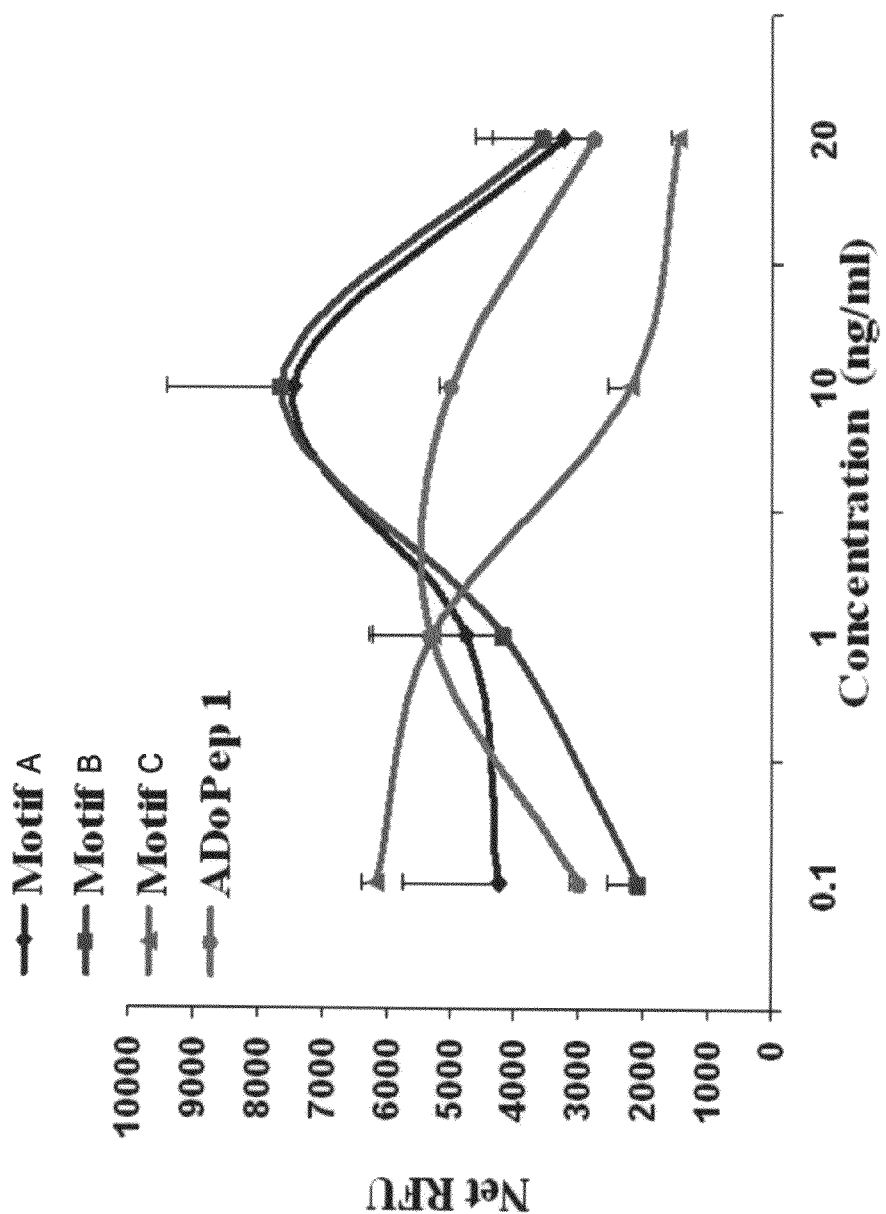

FIGS. 26a-b are graphs depicting induction of endothelial cell migration under hypoxia by the ADOPEP motifs. Endothelial cells were incubated for 5 hours under hypoxia conditions in the presence of increasing concentrations of ADOPep1 (red line), peptide motif A (dark blue line), peptide motif B (green line) or peptide motif C (light blue line) and the migration of endothelial cells was detected. FIG. 26a—experiment 1; FIG. 26b—experiment 2. Note that while the ADOPep1, Motif A and B peptides induced endothelial cell migration at a concentration of about 10 ng/ml, motif C peptide exhibited no significant effect on endothelial cell migration.

Figure 27:
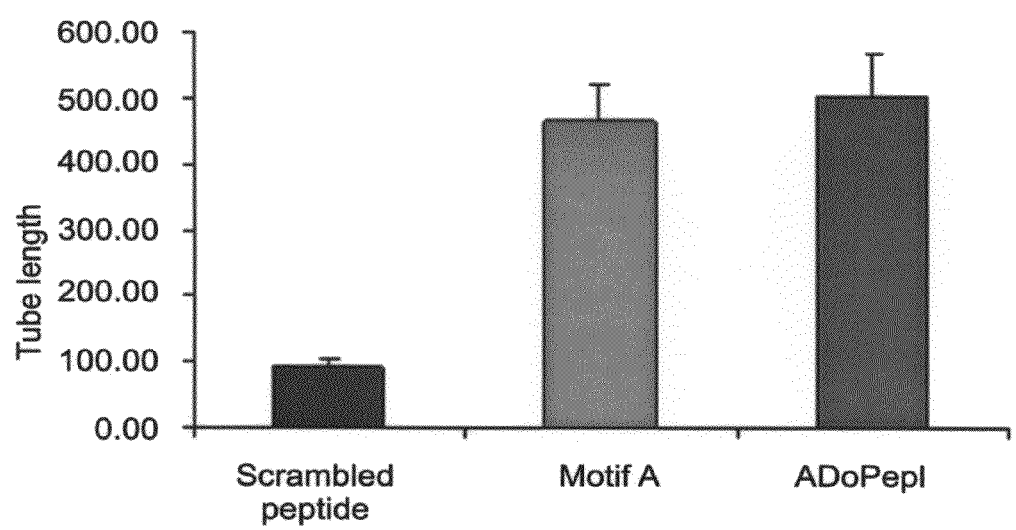

FIG. 27 is a graph depicting induction of tube formation using AdoPep1 and Motif A (SEQ ID NO:7) but not the scrambled sROY peptide. Endothelial cells were incubated in media without supplements for 24 hours, and 50,000 cells were then transferred in 500 μl medium to 24-well plates precoated with 250 μl Cultrex Basement Membrane Extract (with reduced growth factors) (R&D Systems, Minneapolis, Minn., USA). AdoPep1, Motif A and scrambled sROY peptides were added at an optimal concentration of 10 ng/ml (based on preliminary findings), and the slides were examined by light microscopy after 18 hours incubation. The results represent average±SD of three experiments using 3 different cords. The length of the network of connected cells (tube formation) was measured in micrometers in 5 different areas of each well using Image-Pro Plus Image software (Media Cybernetics, Silver Spring, Md., USA). Note that ADOPep1 and Motif A significantly increased the length of the network of connected cells in endothelial cells under starvation and normoxic conditions while scrambled sROY (as a control peptide), did not induced tube formation.

Figure 28A:
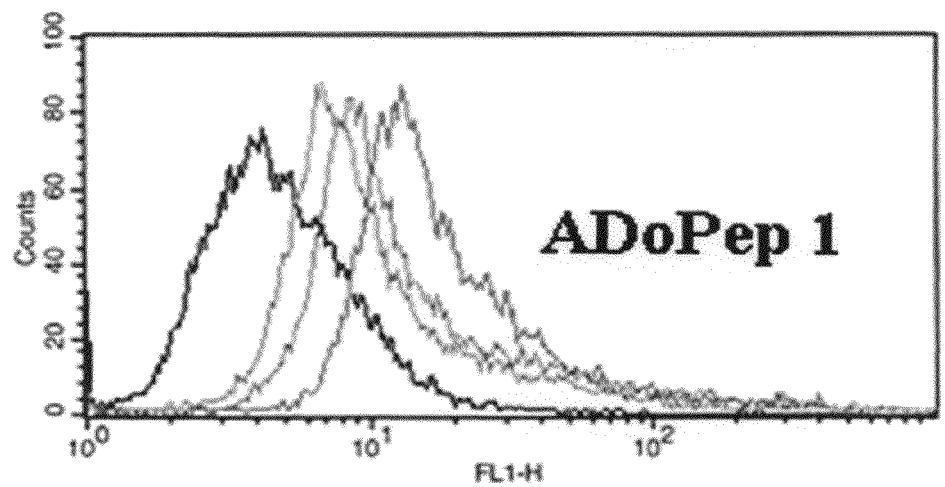
Figure 28B:
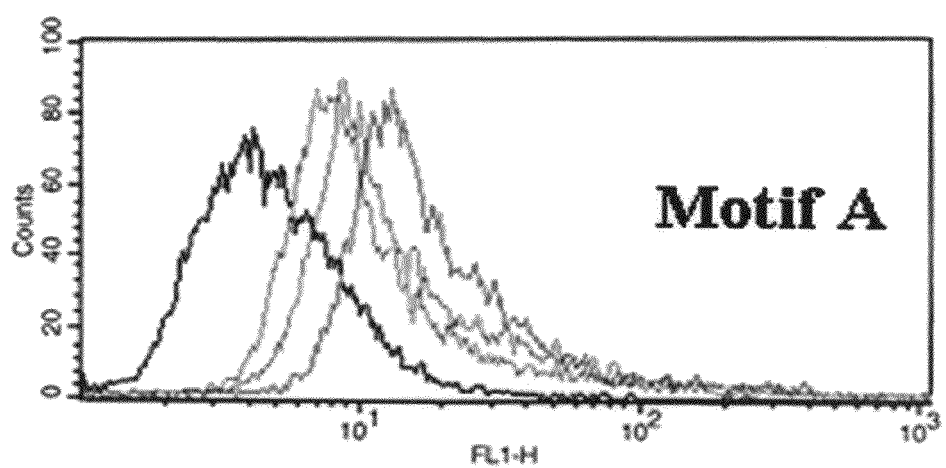
Figure 28C:
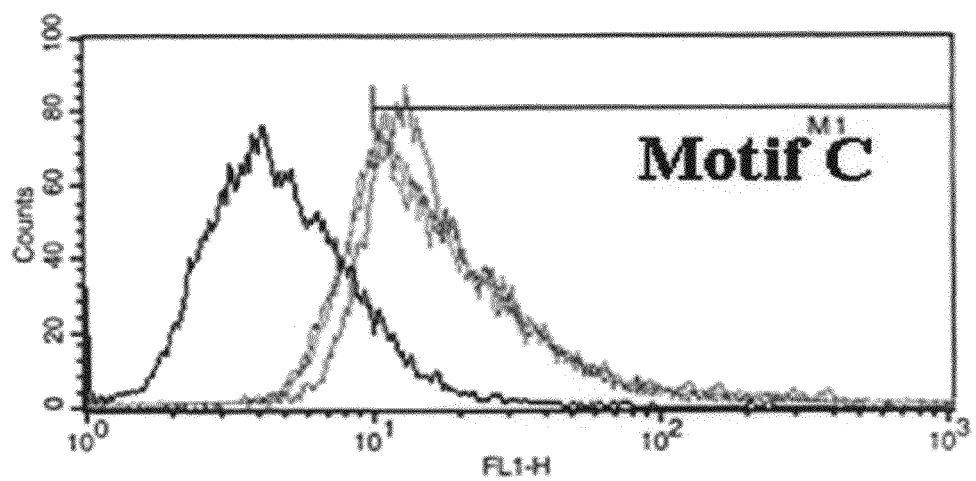
Figure 28D:
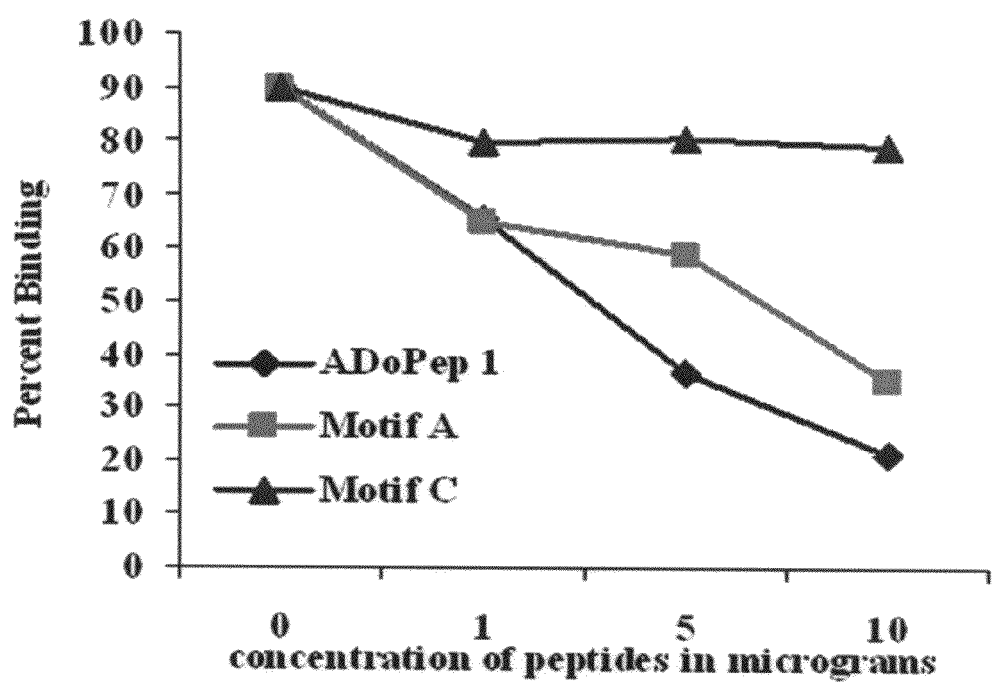

FIGS. 28a-d are FACS histograms (FIGS. 28a-c) and a graph (FIG. 28d) demonstrating that AdoPep1 and Motif A peptides compete on the binding to the same receptor on endothelial cells. Endothelial cells were cultured for 24 hours under hypoxic conditions in endothelial cell growth medium. Cells were removed by trypsin and incubated for 1 hour on ice with increasing concentrations of AdoPep1, Motif A and Motif C peptides. GRP78 polyclonal antibody (2 µg/100,000) was added to the cells for 2 hours on ice. Anti-goat FITC (Jackson ImmunoResearch) was added for 30 minutes on ice. IgG1-FITC was used as the isotype control. The samples were analyzed with a FACScan (Beckton Dickinson). Note that AdoPep1 peptide (FIG. 28a) and Motif A peptide (FIG. 28b) but not Motif C peptide (FIG. 28c) inhibit the binding of GRP78 to endothelial cells. FIG. 28d depicts the average percent binding of GRP78 to endothelial cells as a function of peptide amount as determined by 2 independent experiments.

Figure 29:
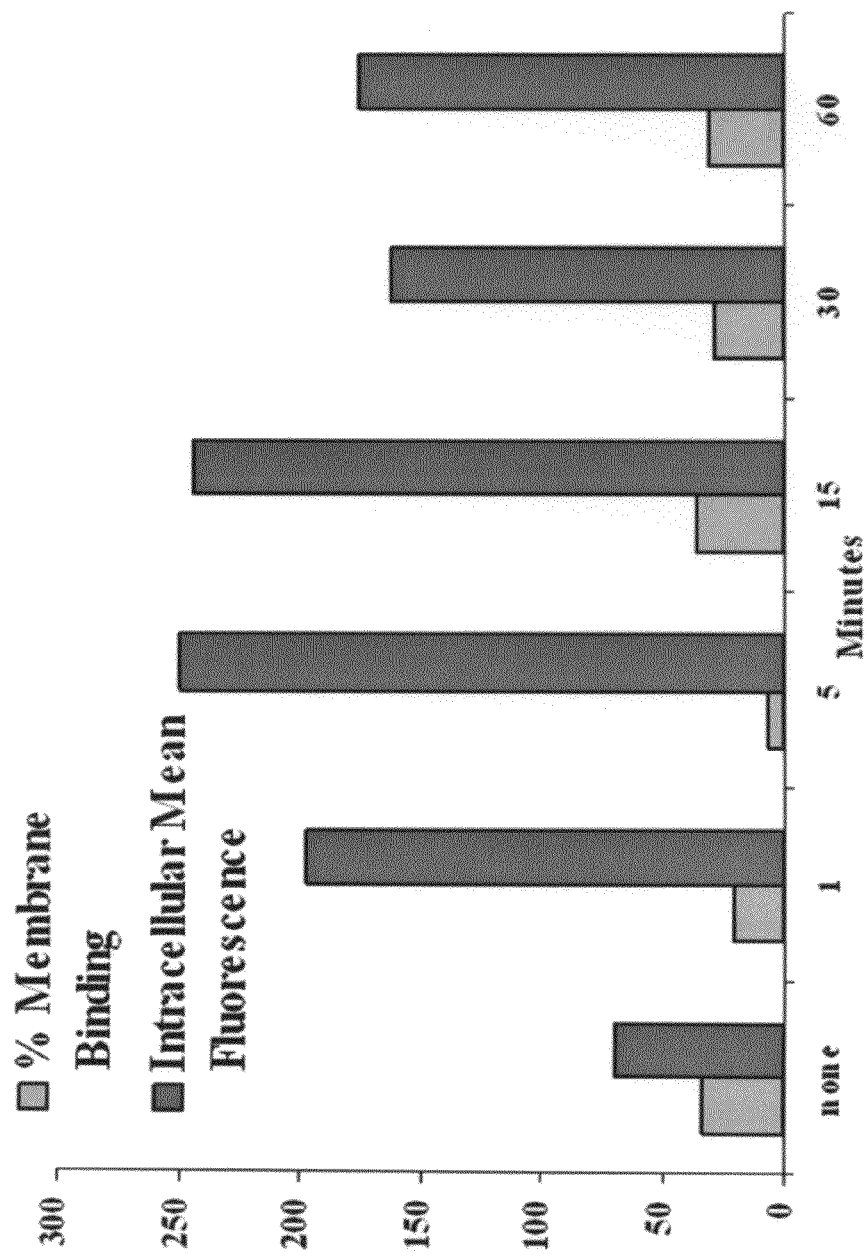
Figure 30A:
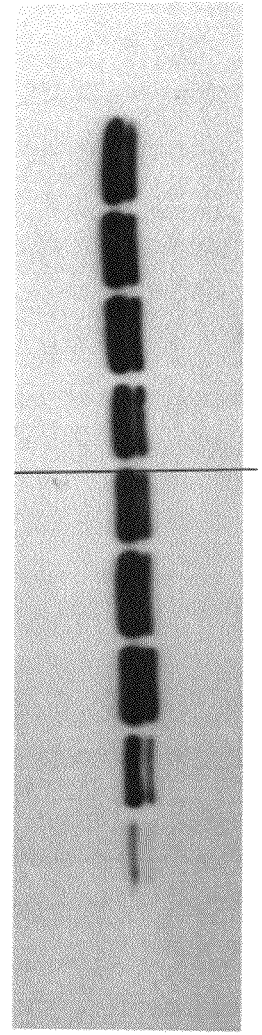
Figure 30B:
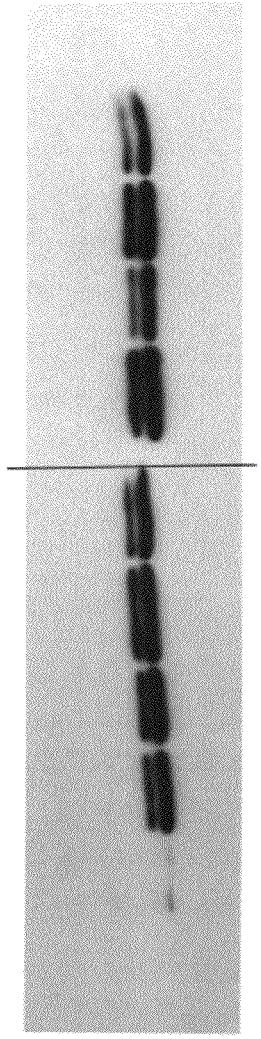

FIG. 29 is a graph depicting GRP78 receptor internalization response to ADOPep1 binding under hypoxic conditions. Endothelial cells were incubated under starvation conditions and hypoxia over night. Cells were incubated with 10 ng/ml ADoPep1 for 5, 15, 30 and 60 minutes. For membrane staining biotinylated AdoePep1 at 5 micrograms was added to intact cells for 1 hour and replaced by streptavidin FITC. For intracellular staining, cells were fixed with 1% paraformaldehyde followed by 15 minutes incubation with 0.1% saponin. After washing of cells, biotinylated AdoPep was added to the cells. The samples were analyzed with a FACScan (Beckton Dickinson). Membrane staining is shown by the blue bars (results are expressed in percentages, as normalized to untreated cells); Mean intracellular staining is shown by the purple bars (results are expressed in mean fluorescence);

FIGS. 30a-b are Western blot analyses depicting induction of phosphorylation of ERK by ADoPep1 and Motif A. Endothelial cells under starvation conditions and 5 hours hypoxia were incubated for 5 (lanes 2 and 6), 20 (lanes 3 and 7), 30 (lanes 4 and 8) and 60 (lanes 5 and 9) minutes with 10 ng/ml ADoPep1 (Lanes 2-5) or Motif A (lanes 6-9) peptides or remained under hypoxia without a further incubation with a peptide (lane 1). After incubation, lysates were prepared, subject to SDS-PAGE and blotting on a nitrocellulose membrane. Western Blot analysis was performed using anti-Phospho ERK1/2 antibody. Note the induction of ERK1/2 phosphorylation after 20 minutes incubation with ADoPep1 and Motif A under hypoxia conditions. Densitometry measurements showed a maximal ERK phosphorylation after 20 minutes incubation with ADOPep1 and from 20 to 60 minutes with Motif A (data not shown). FIG. 30a—Experiment 1; FIG. 30b—Experiment 2. The percent adjusted volume as determined by a densitometric analysis software to compare net band densities was as follows: FIG. 30a, lane 1—4.5, lane 2—9.3, lane 3—13.7, lane 4—13.3, lane 5—11.2, lane 6—10.7, lane 7—12.4, lane 8—12.3 and lane 9—12.4; FIG. 30b, lane 1—4.21, lane 2—12.4, lane 3—12.5, lane 4—14.8, lane 5—10.9, lane 6—14.9, lane 7—9.8, lane 8—12.7 and lane 9—7.8.

Figure 31:
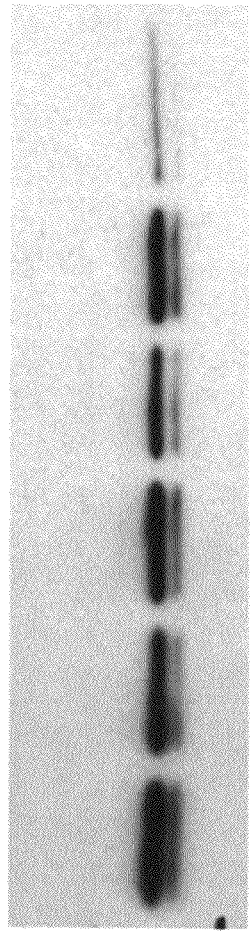
Figure 33B:
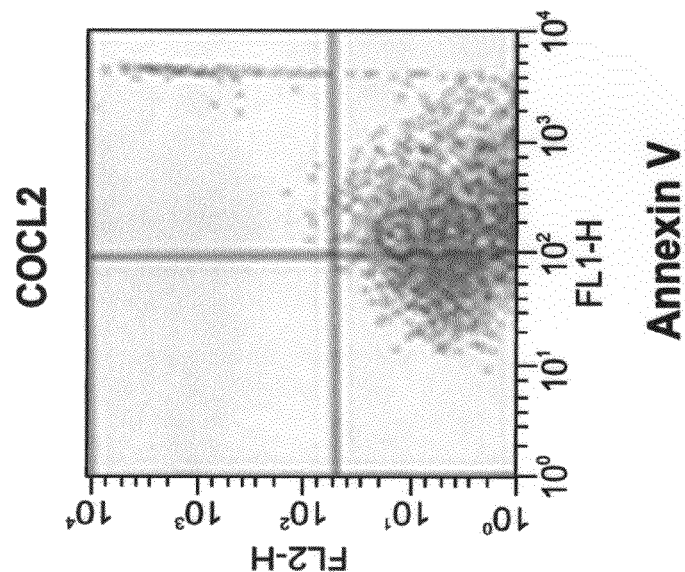
Figure 33A:
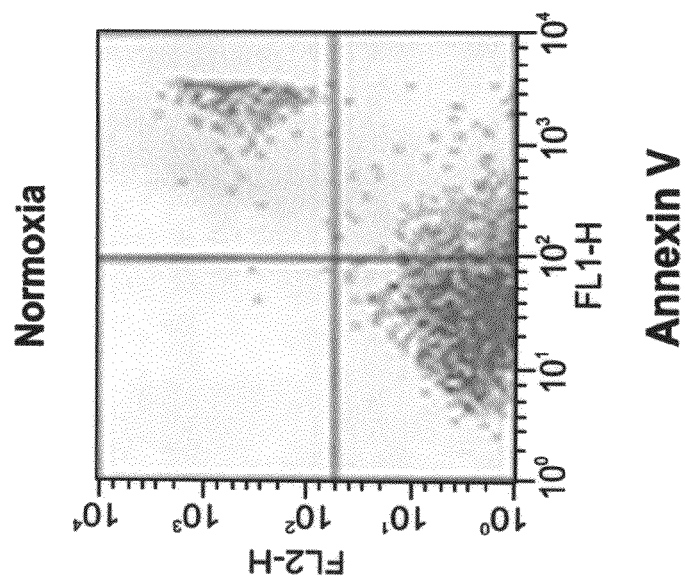
Figure 33C:
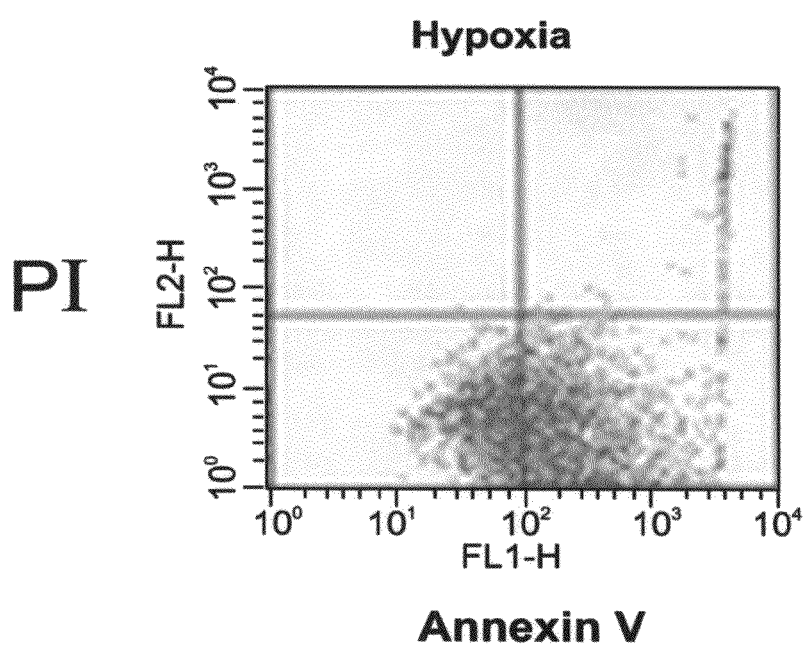
Figure 33E:
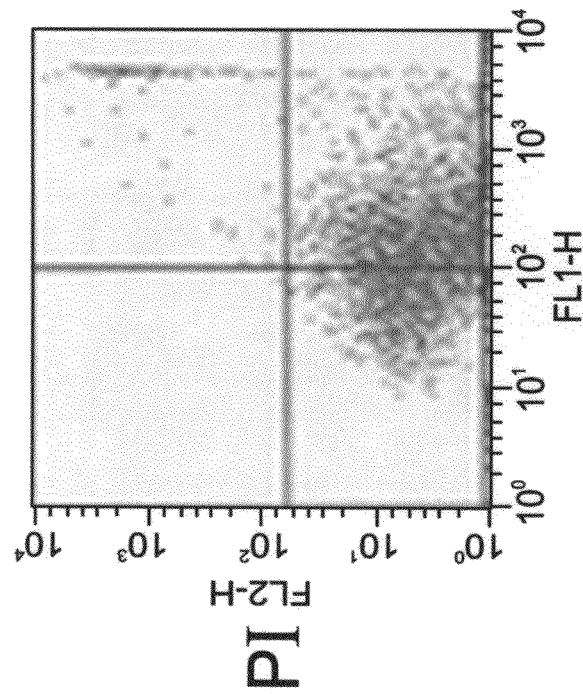
Figure 33D:
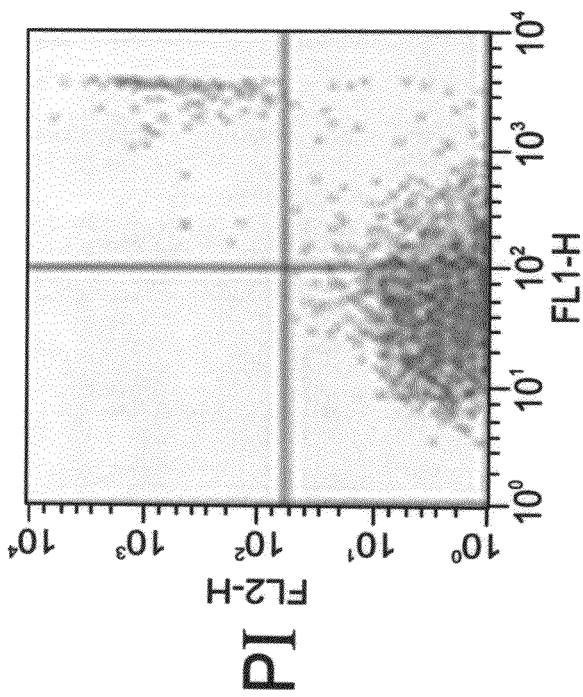
Figure 33F:
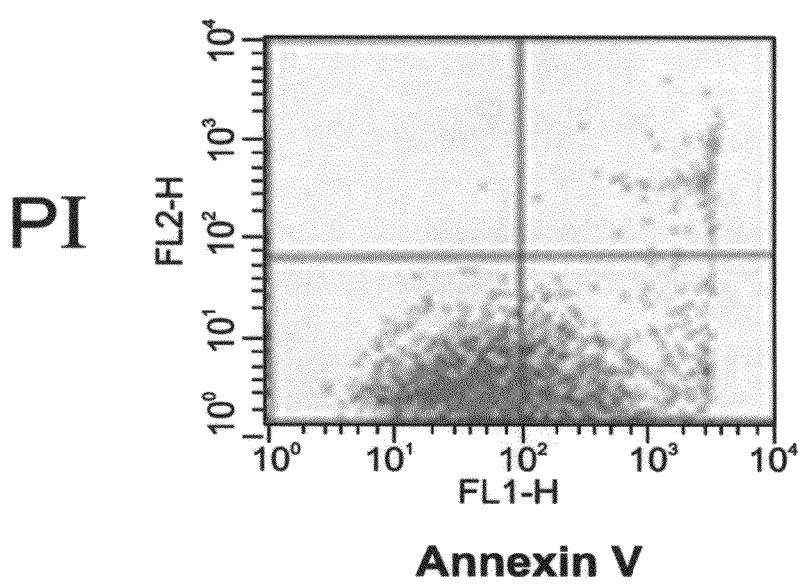

FIG. 31 is a Western blot analysis depicting the level of phosphorylated ERK (pERK) in endothelial cells activated for 20 minutes with ADOPep1 and motif A and inhibited by pERK-inhibitor peptide. Endothelial cells (from cord 1) under starvation conditions and 5 hours hypoxia were incubated with 10 ng/ml ADOPep1 (lanes 3 and 4) or motif A (lanes 1 and 2) peptides in the presence (lanes 2 and 4) or absence (lanes 1 and 3) of p-ERK-inhibitor peptide (Santa Cruz). For control, the endothelial cells under starvation conditions and 5 hours hypoxia (lane 5) were also incubated with the p-ERK-inhibitor peptide (lane 6). Note the inhibition of ERK phosphorylation in the presence of the p-ERK-inhibitor peptide. The percent adjusted volume as determined by a densitometric analysis software to compare net band densities was as follows: lane 1—19, lane 2—14, lane 3-14, lane 4—8.8, lane 5—11, lane 6—2.1.

FIGS. 32a-b are Western blot analyses depicting the effect of ADOPeps on the level of phosphorylated ERK. Endothelial cells (EC) from cord 1 (FIG. 32a) or cord 2 (FIG. 32b) under hypoxia (5 hours) were incubated for 20 or 30 minutes with 10 ng/ml of AdoPep1, AdoPep2 and AdoPep3 or remained untreated (i.e., under hypoxia without any peptide). Western Blot analyses of samples cell lysates were performed with anti Phospho ERK antibody on nitrocellulose membranes. FIG. 32a: Lanes 1 and 2—EC under hypoxia (untreated); lanes 3 and 4—EC under hypoxia incubated with ADOPep3 for 20 (lane 3) or 30 (lane 4) minutes; lanes 5 and 6—EC under hypoxia incubated with ADOPep2 for 20 (lane 5) or 30 (lane 6) minutes; lanes 7 and 8—EC under hypoxia incubated with ADOPep1 for 20 (lane 7) or 30 (lane 8) minutes; FIG. 32b: Lanes 1-4—EC under hypoxia incubated for 20 minutes with ADOPep1 (lane 2), ADOPep2 (lane 3), ADOPep3 (lane 4) or remained untreated (lane 1); lanes 5-8—EC under hypoxia incubated for 30 minutes with ADOPep1 (lane 6), ADOPep2 (lane 7), ADOPep3 (lane 8) or remained untreated (lane 5); Densitometry measurements showed an increase in ERK1/2 phosphorylation after incubation of endothelial cells with ADOPep1 and 2 but not with AdoPep3. The percent adjusted volume as determined by a densitometric analysis software to compare net band densities was as follows: FIG. 32a, lane 1—11, lane 2—13, lane 3—11, lane 4—5, lane 5—11, lane 6—13, lane 7—17, lane 8—16.7; FIG. 32b, lane 1—17, lane 2—22, lane 3—19, lane 4—7, lane 5—8, lane 6—13, lane 7—14, lane 8—1.

FIGS. 33a-f are representative FACS analyses depicting a specific inhibition of hypoxia-induced apoptosis of endothelial cells by ADOPep1. Endothelial cells in Petri dishes were incubated for 24 hours with 5% FCS in supplement-free endothelial cell growth medium under normoxia (FIGS. 33a and d), exposed to 24 hours hypoxia (Figures c and f) or incubated under normoxia with 100 micromolar per 100,000 cells CoCl$_2$ (FIGS. 33b and e), in the absence (FIGS. 33a-c) or presence (FIGS. 33d-f) of 10 ng/ml Adopep1 peptide (for 24 hours). Cells were trypsinized and immediately re-suspended in PBS with 5% FCS and 0.1% Na-azide. Samples containing 100,000 cells were tested for apoptosis using the Annexin-FITC (X axis) and propidium iodide (Y axis) kit (Bender Medsystems, Vienna, Austria), according to manufacturer's instructions. Results were analyzed by FACScan (Beckton Dickinson). Note that while CoCl$_2$ and hypoxia conditions increased the fraction of apoptotic cells (indicated by the increase of PI and Annexin-FITC positive cells in FIGS. 33b and c as compared to FIG. 33a), when the cells were incubated with ADOPep1 peptide, a significant fraction of hypoxia-induced apoptosis was inhibited (compare PI and Annexin-FITC positive cells in FIG. 33f to those in FIG. 33c), however, no effect on apoptosis induced by CoCl₂ was observed (compare PI and Annexin-FITC positive cells in FIG. 33e to those in FIG. 33b).

Figure 34:
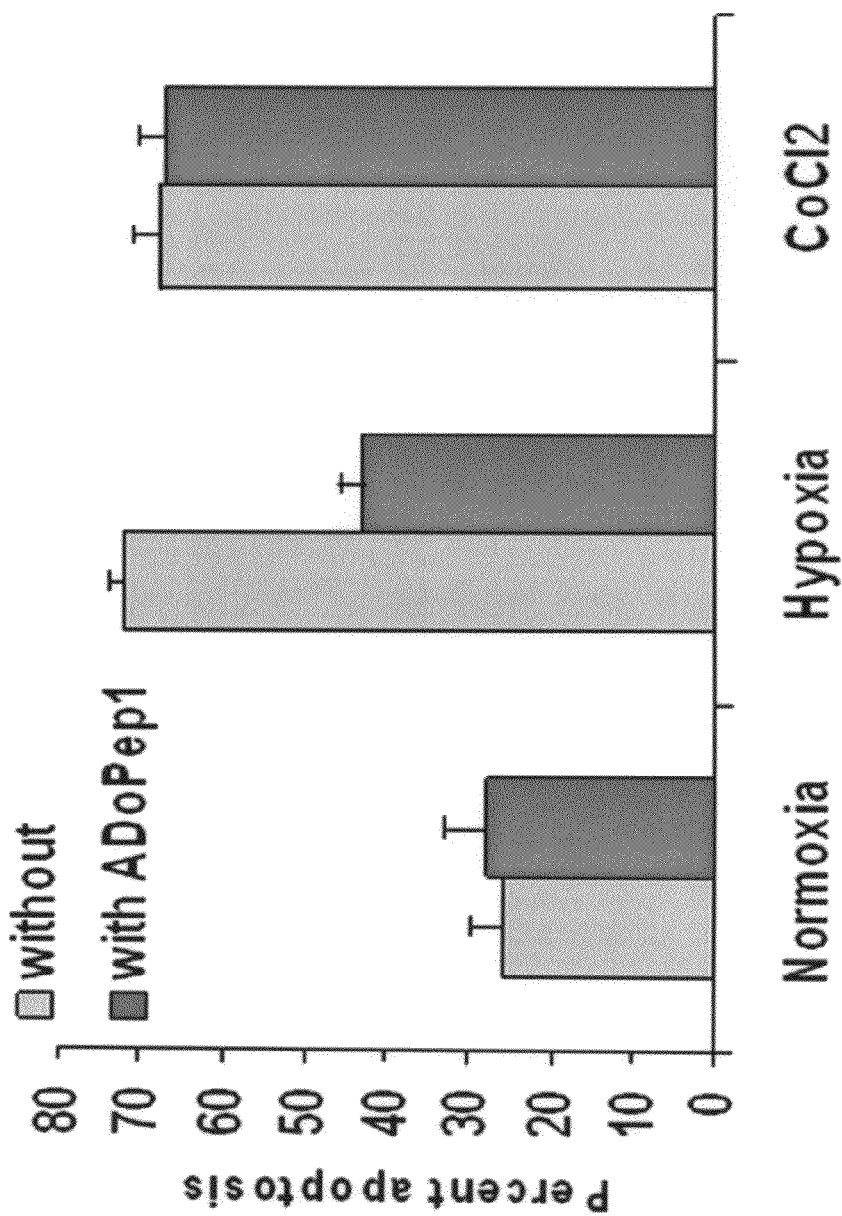

FIG. 34 is a histogram depicting the FACS results of the experiments described in FIGS. 33a-f. Data represents average±SD of 2 experiments. Note that 24 hours of hypoxia or CoCl₂ treatment increased the level of apoptosis from about 27% (under normoxia) to about 70% or 67%, respectively. Also note that ADOPep1 treatment significantly inhibited the hypoxia induced apoptosis by approximately 40 percent but not the CoCl₂ induced apoptosis.

DESCRIPTION OF EMBODIMENTS OF THE INVENTION

Some embodiments of the invention relate to peptides which can bind to endothelial cells via the GRP78 receptor and induce angiogenesis and to uses thereof for treating pathologies characterized by insufficient angiogenesis such as ischemic diseases.

The principles and operation of the peptides, compositions and methods according to the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the invention to practice, the present inventors have uncovered that short amino acid sequences comprising the Histidine-Tryptophan-Arginine-Arginine (HWRR) amino acid motif (derived from the ADAM15 protein) are capable of binding to the GRP78 receptor on endothelial cell, induce endothelial cells proliferation and migration and inhibit hypoxia-induced apoptosis and thus can be used to induce angiogenesis and treat ischemic diseases.

As described in the Examples section which follows, the peptides of the invention (e.g., ADOPeps-1, 2 and 3 as set forth by SEQ ID NOs: 2, 3 and 4, respectively, or the peptides set forth by SEQ ID NOs:7 and 8) bind to endothelial cells in vitro (FIGS. 3 and 4) and induce endothelial cell proliferation (FIG. 5) and migration (FIGS. 6 and 26a-b) under hypoxia. In addition, in vivo experiments utilizing the mouse hind limb ischemia model have shown that treatment of the ischemic mice with the peptides of the invention (e.g., ADOPep1) significantly increases blood perfusion (FIG. 7) and blood vessel density (FIGS. 8, 9a-b). Moreover, immuno precipitation (IP) and Western blot analyses revealed that the receptor of ADOPeps on endothelial cells is the glucose-regulated protein (GRP78; SEQ ID NO:9) (FIGS. 10a-b, 11, 12) which is expressed on various tumor cells (FIGS. 16a-d) and that the peptides of the invention (e.g., ADOPep1) bind to GRP78 on endothelial cells under hypoxia (FIGS. 13a-b and 19). In addition, while hypoxia conditions increase the presentation of the GRP78 receptor on endothelial cells to about 40% (FIG. 15), pre-incubation of endothelial cells with the ADOPep1 further increases GRP78 presentation on endothelial cells to about 84% (FIGS. 20a-b, 21). Furthermore, the peptides of the invention (e.g., ADOPep1, or shorter peptides such as SEQ ID NOs: 7 and 8) prevented hypoxia-induced apoptosis of endothelial cells both in vitro (FIGS. 17, 18, 24a-d and 25) and in vivo (FIG. 22) but not Cobalt Chloride-induced apoptosis (FIGS. 33a-f and 34). In addition, incubation of endothelial cells with the peptides of the invention (e.g., SEQ ID NO:2 or 7) result in tube formation (FIG. 27) and a significant increase in ERK1/2 phosphorylation (FIGS. 30a-b, 31). Altogether, these results demonstrate the ability of the peptides of the invention to induce angiogenesis in a tissue under hypoxia, and suggest their use for treating ischemic diseases.

Thus, according to one aspect of the invention, there is provided an isolated peptide comprising the amino acid sequence HWRR (SEQ ID NO:5), the peptide consists of 4 or 5 amino acids.

For example, the peptide according to this aspect of the invention can be any of the peptides listed in Table 1, hereinbelow:

TABLE 1

Exemplary isolated peptides of the invention

| Amino Acid Sequence | SEQ ID NO: |
|---|---|
| HWRRP | 7 |
| HWRRA | 8 |
| HWRRR | 61 |
| HWRRN | 62 |
| HWRRD | 63 |
| HWRRC | 64 |
| HWRRQ | 65 |
| HWRRE | 66 |
| HWRRG | 67 |
| HWRRH | 68 |
| HWRRI | 69 |
| HWRRL | 70 |
| HWRRK | 71 |
| HWRRM | 72 |
| HWRRF | 73 |
| HWRRS | 74 |
| HWRRT | 75 |
| HWRRW | 76 |
| HWRRY | 77 |
| HWRRV | 78 |
| AHWRR | 79 |
| RHWRR | 80 |
| NHWRR | 81 |
| DHWRR | 82 |
| CHWRR | 83 |
| QHWRR | 84 |
| EHWRR | 85 |

TABLE 1-continued

Exemplary isolated peptides of the invention

| Amino Acid Sequence | SEQ ID NO: |
|---|---|
| GHWRR | 86 |
| HHWRR | 87 |
| IHWRR | 88 |
| LHWRR | 89 |
| KHWRR | 90 |
| MHWRR | 91 |
| FHWRR | 92 |
| PHWRR | 93 |
| SHWRR | 94 |
| THWRR | 95 |
| WHWRR | 96 |
| YHWRR | 97 |
| VHWRR | 98 |

According to an embodiment of the invention, the peptide of the invention can be HWRRP (SEQ ID NO:7) or HWRRA (SEQ ID NO:8).

It will be appreciated that the invention also contemplates longer peptides which comprise the HWRR amino acid sequence.

Thus, according to another aspect of the invention, there is provided an isolated peptide comprising an amino acid sequence HWRR as set forth by SEQ ID NO:5, with the proviso that the peptide is not SEQ ID NO:11 (YPHIDSLGH-WRR).

According to an embodiment of the invention, the peptide of this aspect of the invention comprises at least 4 amino acids (e.g., 4), at least 5 amino acids (e.g., 5), at least 6 (e.g., 6) amino acids, at least 7 (e.g., 7) amino acids, at least 8 (e.g., 8) amino acids, at least 9 (e.g., 9) amino acids, at least 10 (e.g., 10) amino acids, at least 11 (e.g., 11) amino acids, at least 12 (e.g., 12) amino acids, at least 13 (e.g., 13) amino acids, at least 14 (e.g., 14) amino acids, at least 15 (e.g., 15) amino acids, at least 16 (e.g., 16) amino acids, at least 17 (e.g., 17) amino acids, at least 18 (e.g., 18) amino acids, at least 19 (e.g., 19) amino acids, at least 20 (e.g., 20) amino acids, at least 21 (e.g., 21) amino acids, at least 22 (e.g., 22) amino acids, at least 23 (e.g., 23) amino acids, at least 24 (e.g., 24) amino acids, at least 25 (e.g., 25) amino acids, at least 26 (e.g., 26) amino acids, at least 27 (e.g., 27) amino acids, at least 28 (e.g., 28) amino acids, at least 29 (e.g., 29) amino acids, at least 30 (e.g., 30) amino acids, at least 31 (e.g., 31) amino acids, at least 32 (e.g., 32) amino acids, at least 33 (e.g., 33) amino acids, at least 34 (e.g., 34) amino acids, at least 35 (e.g., 35) amino acids, at least 36 (e.g., 36) amino acids, at least 37 (e.g., 37) amino acids, at least 38 (e.g., 38) amino acids, at least 39 (e.g., 39) amino acids, at least 40 (e.g., 40) amino acids, at least 41 (e.g., 41) amino acids, at least 42 (e.g., 42) amino acids, at least 43 (e.g., 43) amino acids, at least 44 (e.g., 44) amino acids, at least 45 (e.g., 45) amino acids, at least 46 (e.g., 46) amino acids, at least 47 (e.g., 47) amino acids, at least 48 (e.g., 48) amino acids, at least 49 (e.g., 49) amino acids and no more than 50 (e.g., 50).

According to an embodiment of the invention, the peptide of this aspect of the invention comprises 50 or less amino acids, 49 or less amino acids, 48 or less amino acids, 47 or less amino acids, 46 or less amino acids, 45 or less amino acids, 44 or less amino acids, 43 or less amino acids, 42 or less amino acids, 41 or less amino acids, 40 or less amino acids, 39 or less amino acids, 38 or less amino acids, 37 or less amino acids, 36 or less amino acids, 35 or less amino acids, 34 or less amino acids, 33 or less amino acids, 32 or less amino acids, 31 or less amino acids, 30 or less amino acids, 29 or less amino acids, 28 or less amino acids, 27 or less amino acids, 26 or less amino acids, 25 or less amino acids, 24 or less amino acids, 23 or less amino acids, 22 or less amino acids, 21 or less amino acids, 20 or less amino acids, 19 or less amino acids, 18 or less amino acids, 17 or less amino acids, 16 or less amino acids, 15 or less amino acids, 14 or less amino acids, 13 or less amino acids, 12 or less amino acids, 11 or less amino acids, 10 or less amino acids, 9 or less amino acids, 8 or less amino acids, 7 or less amino acids, 6 or less amino acids, 5 amino acids or 4 amino acids.

It will be appreciated that the length ("x") of the peptide of the invention can be any integer with a value which is at least "n" and no more than "y". Thus, $n \leq x \leq y$, wherein $n < y$ and whereas "n" is an integer having a value between 4 to 49 and "y" is an integer having a value between 5 and 50.

According to an embodiment of the invention, the peptide of this aspect of the invention comprises at least 4 and no more than 50 amino acids, at least 4 and no more than 7 amino acids, at least 5 and no more than 8 amino acids, at least 6 and no more than 9 amino acids, at least 7 and no more than 10 amino acids, at least 8 and no more than 11 amino acids, at least 9 and no more than 12 amino acids, at least 7 and no more than 13 amino acids, at least 12 and no more than 17 amino acids, at least 12 and no more than 20 amino acids, at least 12 and no more than 30 amino acids, at least 10 and no more than 20 amino acids, at least 8 and no more than 30 amino acids, at least 12 and no more than 40 amino acids.

According to an embodiment of the invention, the peptide of this aspect of the invention comprises the amino acid sequence as set forth in SEQ ID NO:2.

According to an embodiment of the invention, the peptide of this aspect of the invention comprises the amino acid sequence as set forth in SEQ ID NO:3.

According to an embodiment of the invention, the peptide of this aspect of the invention comprises the amino acid sequence as set forth in SEQ ID NO:4.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

Further details in this respect are provided hereinunder. Peptide bonds (—CO—NH—) within the peptide may be substituted, for example, by N-methylated bonds (—N(CH$_3$)—CO—), ester bonds (—C(R)H—C—O—O—C (R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr and Phe, may be substituted for synthetic non-natural acid, such as Phenylglycine, TIC, naphthylelanine (Nol), ring-methylated derivatives of Phe, halogenated derivatives of Phe or o-methyl-Tyr.

In addition to the above, the peptides of the invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other less common amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids (e.g., synthetic, Table 3) which can be used with the invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |

TABLE 3-continued

| Non-conventional amino acid | Code | Non-conventional amino acid | Code |
|---|---|---|---|
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | Penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The peptides of the invention can be utilized in a linear form, although it will be appreciated that in cases where cyclization does not severely interfere with peptide characteristics, cyclic forms of the peptide can also be utilized. Cyclic peptides can either be synthesized in a cyclic form or configured so as to assume a cyclic form under desired conditions (e.g., physiological conditions).

It will be appreciated that since one of the main obstacles in using short peptide fragments in therapy is their proteolytic degradation by stereospecific cellular proteases, the peptides of the invention can be synthesized from D-isomers of natural amino acids [i.e., inverso peptide analogues, Tjernberg (1997) J. Biol. Chem. 272:12601-5, Gazit (2002) Curr. Med. Chem. 9:1667-1675].

Additionally, the peptides of the invention include retro, inverso, and retro-inverso analogues thereof. It will be appreciated that complete or extended partial retro-inverso analogues of hormones have generally been found to retain or enhance biological activity. Retro-inversion has also found application in the area of rational design of enzyme inhibitors (see U.S. Pat. No. 6,261,569).

As used herein a "retro peptide" refers to peptides that are made up of L-amino acid residues which are assembled in opposite direction to the native peptide sequence.

Retro-inverso modification of naturally occurring polypeptides involves the synthetic assembly of amino acids with α-carbon stereochemistry opposite to that of the corresponding L-amino acids, i.e., D- or D-allo-amino acids in inverse order to the native peptide sequence. A retro inverso analogue, thus, has reversed termini and reversed direction of peptide bonds, while essentially maintaining the topology of the side chains as in the native peptide sequence.

It will be appreciated that incorporation of any of the above-mentioned amino acid modifications including conserved changes in amino acid residues of the peptides of the invention can be effected, as long as the angiogenic function (e.g., endothelial cell proliferation, migration, vascular sprouting, vascularization) of the peptides of the invention is retained. To test this, any of the angiogenesis assays described hereinbelow and in the Examples section which follows can be effected.

The peptides of the invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Further description of peptide synthesis is disclosed in U.S. Pat. No. 6,472,505. One method of preparing the peptide compounds of the invention involves solid-phase peptide synthesis, utilizing a solid support. Large-scale peptide synthesis is described by Andersson Biopolymers 2000, 55(3), 227-50.

Recombinant techniques can be used when large amounts of the peptides are required (can be used when long peptides are required). Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Briefly, a nucleic acid construct comprising a polynucleotide sequence encoding the peptide of the invention and a promoter for directing the expression of the polynucleotide in a host cell (e.g., a prokaryotic host cell such as E. Coli, or a eukaryotic host cell such as plant, yeast or mammalian cells) can be used along with the suitable host cells under conditions suitable for production of the recombinant peptide.

The peptides of the invention can be retrieved in "substantially pure" form. As used herein, "substantially pure" refers to a purity that allows for the effective use of the peptide in the diverse applications, described herein (e.g., for therapeutic or diagnostic purposes).

Thus, the invention provides a composition-of-matter which comprises at least one of the peptides of the invention. For example, the composition-of-matter of the invention may comprises one, two, three or more of the peptides of the invention.

According to an embodiment of the invention, the peptide of the invention is capable of binding the glucose-regulated protein (GRP78) as set forth by SEQ ID NO:9 on endothelial cells of the tissue.

According to an embodiment of the invention, the binding of peptide of the invention to GRP78 results in induction of angiogenesis (i.e., inducing vascularization) in a tissue of a subject even under hypoxic conditions.

It will be appreciated that the pro-angiogenic peptides of the invention can be used to induce angiogenesis in a subject.

Thus, according to an additional aspect of the invention there is provided a method of inducing angiogenesis in a subject in need thereof. The method is effected by administering to the subject a therapeutically effective amount of at least one peptide of the peptides of the invention, to thereby induce angiogenesis in the subject in need thereof.

As used herein the term "subject" refers to a mammal, such as a canine, a feline, a bovine, a porcine, an equine or a human subject.

According to an embodiment of the invention, the subject is human.

As used herein the phrase "a subject in need thereof" refers to a subject who is diagnosed with, predisposed to or suffers from an angiogenesis-dependent pathology.

As used herein the phrase "angiogenesis-dependent pathology" refers to any pathology (i.e., a condition, disease or disorder) which is characterized by and/or results from disregulated angiogenesis, i.e., insufficient angiogenesis or excess of angiogenesis.

According to an embodiment of the invention, the angiogenesis-dependent pathology according to this aspect of the invention refers to a pathology which is characterized by and/or results from insufficient angiogenesis. Examples include but are not limited to delayed wound-healing, delayed ulcer healing, reproduction associated disorders, arteriosclerosis, ischemic vascular disease, ischemic heart disease, myocardial ischemia, myocardial infarction, heart failure, myocardial dysfunction, myocardial remodeling, cardiomyopathies, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, critical leg ischemia, lower extremity ischemia, cerebral ischemia [e.g., such as cerebral ischemia in childhood moyamoya disease (Touho H. 2007, Surg Neurol. June 20; Epub ahead of print)], cerebro vascular disease, retinopathy, retinal repair, remodeling disorder, von Hippel-Lindau syndrome, diabetes, hereditary hemorrhagic telengiectasia, ischemic vascular disease, Buerger's disease, and ischemia associated with neurodegenerative disease such as Parkinson's and Alzheimer's disease.

It will be appreciated that inducing angiogenesis in a tissue of a subject in need thereof can be used to treat a pathology (e.g., disease) characterized by insufficient angiogenesis (as described hereinabove) in a tissue of a subject.

Induction of angiogenesis and/or treating a pathology characterized by insufficient angiogenesis in a subject is achieved according to this aspect of the invention by administering at least one of the peptides of the invention to the subject.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

It will be appreciated that the peptide of the invention can be administered to the subject per se or in a pharmaceutical composition where it is mixed with suitable carriers or excipients.

As used herein a "pharmaceutical composition" refers to a preparation of one or more of the active ingredients described herein (i.e., at least one peptide of the peptides of the invention) with other chemical components such as physiologically suitable carriers and excipients. The purpose of a pharmaceutical composition is to facilitate administration of a compound to an organism.

Herein the term "active ingredient" refers to the peptide of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the CNS include: neurosurgical strategies (e.g., intracerebral injection or intracerebroventricular infusion); molecular manipulation of the peptide [e.g., production of a chimeric fusion peptide that comprises the peptide of the invention which can bind the surface of endothelial cells in combination with an agent that is itself incapable of crossing the blood brain barrier (BBB)] in an attempt to exploit one of the endogenous transport pathways of the BBB; pharmacological strategies designed to increase the lipid solubility of the peptide (e.g., conjugation of a water-soluble peptide to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Alternately, one may administer the pharmaceutical composition in a local rather than a systemic manner, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, such as in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the invention may also be formulated in rectal compositions such as suppositories or retention enemas, using, e.g., conventional suppository bases such as cocoa butter or other glycerides.

Pharmaceutical compositions suitable for use in context of the invention include compositions wherein the active ingredients are contained in an amount effective to achieve the intended purpose. More specifically, a therapeutically effective amount means an amount of active ingredients (the peptide of the invention) effective to prevent, alleviate or ameliorate symptoms of a disorder (e.g., a pathology associated with insufficient angiogenesis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue (e.g., cardiac tissue, brain tissue, limb tissue, renal tissue) levels of the active ingredient are sufficient to induce the biological effect (angiogenesis) (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Due to their selective binding to endothelial cells, the peptides of the invention can be used to target agents fused thereto to endothelial cells (ECs) in vitro, ex vivo (i.e., in cells which were removed from a subject) and/or in vivo (i.e., within a living organism, subject). Such an agent can be any molecule that targeting thereof to endothelial cells is desirable and/or beneficial (e.g., beneficial to the subject when in vivo administration is effected).

For example, such an agent can be a drug, a toxic moiety (e.g., which is designed to kill endothelial cells), a chemotherapeutic agent (which is designed to kill cancerous cells within or in the vicinity of the endothelial cells), an identifiable agent (e.g., biotin, digoxeginin, enzymatic moiety which can be used to detect endothelial cells), and a radio-isotope (which is capable of labeling and/or killing endothelial cells).

Examples of toxins which can be fused to the peptide of the invention include, but are not limited to, enzymatically active toxins of bacterial, fungal, plant, or animal origin, or fragments thereof [e.g., diphteria toxin, exotoxin A chain of *Pseudomonas aeruginosa*, ricin A chain, abrin A chain, modeccin A chain, α-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes].

Examples of radioisotopes which can be fused to the peptide of the invention include, but are not limited to, $^{125}$I, $^{131}$I, $^{90}$Y, $^{212}$Bi, $^{198}$Re, $^{188}$Re, $^{186}$Re, $^{211}$At, $^{67}$Cu, and $^{212}$Pb.

Examples of chemotherapeutic agents which can be fused to the peptide of the invention include, but are not limited to, Nitrogen Mustards [e.g., Mechlorethamine ($HN_2$), Cyclophosphamide, Ifosfamide, Melphalan, Chlorambucil and Estramustine], alkylating agents, folic acid antagonists or analogs (e.g., Methotrexate, Trimetrexate), anti-metabolites of nucleic acid metabolism, antibiotics (e.g., Dactinomycin, Daunorubicin, Doxorubicin, 4'-Deoxydoxorubicin, Bleomycin, Plicamycin, Mitomycin), pyrimidine analogs (e.g., Fluorouracil, Floxuridine, Cytarabine), 5-fluorouracil, cisplatin, purine nucleosides, analogs and related inhibitors (e.g., Azacitidine, Mercaptopurine, Thioguanine, Pentostatin, Fludarabine), amines, amino acids, triazol nucleosides, corticosteroids, Ethylenimines and Methylmelamines (e.g., Hexamethyl-melamine, Thiotepa), Alkyl Sulfonates (e.g., Busulfan), Nitrosoureas (e.g., Carmustine, Lomustine, Semustine, Streptozocin), Triazenes (e.g., Dacarbazine, Procarbazine, Aziridine) Vinca Alkaloids [e.g., Vinblastine (VLB), Vincristine, Vindesine], Epipodophyl-Lotoxins (e.g., Etoposide, Teniposide), enzymes (e.g., L-Asparaginase), Taxanes (e.g., Docetaxel, Paclitaxel), biological response modifiers (e.g., interferon alfa, tumor necrosis factor, tumor infiltrating lymphocytes), Platinum coordination complexes (e.g., Cisplatin, carboplatin), Anthracenedione (e.g., mitoxantrone), substituted urea (hydroxyurea), methyl hydrazine derivative (procarbazine), adrenocortical suppressant (mitotane, aminoglutethimide), costeroids, progestins (e.g., hydroxy-progesterone caproate, medroxy progesterone). Specific examples include, Adriamycin, Doxorubicin, 5-Fluorouracil, Cytosine arabinoside (i.e., Ara-C), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as estrogens (e.g., diethylstilbestrol, ethinyl estradiol), antiestrogen (tamoxifen), androgens (testosterone propionate, fluoxymesterone), anti-androgen (flutamide), Gonadotropin-Releasing hormone analog (Leuprolide, Goserelin), and onapristone.

Fusions between the peptides of the invention and the abovedescribed agent can be generated using a variety of bifunctional protein-coupling agents, such as N-succinimidyl-3-(2-pyridyldithiol) propionate (SPDP) (e.g., essentially as described in Cumber et al. 1985, Methods of Enzymology 112: 207-224), iminothiolane (IT), bifunctional derivatives of imidoesters (such as dimethyl adipimidate HCL), active esters (such as disuccinimidyl suberate), aldehydes (such as glutareldehyde; essentially as described in G. T. Hermanson, 1996, "Antibody Modification and Conjugation, in Bioconjugate Techniques, Academic Press, San Diego), bisazido compounds (such as bis-(p-azidobenzoyl) hexanediamine), bis-diazonium derivatives (such as bis-(p-diazoniumbenzoyl)-ethylenediamine), diisocyanates (such as tolyene 2,6-diisocyanate), bis-active fluorine compounds (such as 1,5-difluoro-2,4-dinitrobenzene) or carbodiimide conjugation procedure (as described in J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. Tetrahedron Lett. 4475; E. P. Boden et al. 1986, J. Org. Chem. 50:2394 or and L. J. Mathias 1979, Synthesis 561). For example, a ricin fusion can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the peptide. See WO94/11026; U.S. Pat. No. 6,426,400; Laske, D. W., Youle, R. J., and Oldfield, E. H. (1997) Tumor regression with regional distribution of the targeted toxin TF-CRM107 in patients with malignant brain tumors. Nature Medicine 3:1362-1368.

Additionally or alternatively, the agent of the invention can be attached to the peptide of the invention via recombinant DNA technology by constructing an expression vector which comprises the coding sequence of the agent of the invention (e.g., the PE38KDEL truncated form of pseudomonas exotoxin A) translationally fused to the coding sequence of the peptide of the invention (e.g., SEQ ID NO:2) and expressing the construct in a host cell (e.g., a prokaryotic or eukaryotic cell) for the production of a recombinant fusion peptide comprising the amino acids of the agent and the peptide of the invention. Alternatively, the expression vector can be administered to the subject in need of therapy via known gene therapy techniques (e.g., using vial vehicles).

According to an embodiment of the invention, the composition of the invention which comprises the peptide of the invention and the agent (e.g., the toxin, chemotherapeutic, identifiable moiety or radio-isotope) fused (or attached) thereto can form part of a pharmaceutical composition with a pharmaceutically acceptable carrier.

Accordingly, such a composition (which comprises the therapeutic agent attached or fused to the peptide of the invention) can be used for treating a pathology characterized by abnormally increased angiogenesis (hyper-vascularization). For example, such compositions can be used to inhibit tumor growth by destruction of the tumor vasculature.

Non-limiting examples of pathologies characterized by abnormally increased angiogenesis which can be treated by the composition of the invention include cancer, metastatic cancer, myelodysplastic features (MDF) in bone marrow of HIV patients, primary myelodysplastic syndromes (MDS), Systemic mastocytosis (SM), retinal neovascularization, neovascularization in atherosclerotic plaques, hemangiomas, arthritis, psoriasis, arthritis and other autoimmune diseases.

The cancer or cancer metastases which can be treated by the composition of the invention include, but is not limited to, tumors of the gastrointestinal tract (colon carcinoma, rectal carcinoma, colorectal carcinoma, small and/or large bowel carcinoma, esophageal carcinoma, stomach carcinoma, pancreatic carcinoma), gallbladder carcinoma, Biliary tract tumors, prostate cancer, renal cancer (e.g., Wilms' tumor), liver cancer (e.g., hepatoblastoma, hepatocellular carcinoma), bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian carcinoma, cervical carcinoma, small-cell and non-small cell lung carcinoma, nasopharyngeal, breast carcinoma, squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic), gliomas, adenocarcinoma, adrenal tumor, brain malignancy (tumor), various other carcinomas (e.g., bronchogenic large cell, ductal, Ehrlich-Lettre ascites, epidermoid, large cell, Lewis lung, medullary, mucoepidermoid, oat cell, small cell, spindle cell, spinocellular, transitional cell, undifferentiated, carcinosarcoma, choriocarcinoma, cystadenocarcinoma), ependimoblastoma, epithelioma, erythroleukemia (e.g., Friend, lymphoblast), fibrosarcoma, giant cell tumor, glial tumor, glioblastoma (e.g., multiforme, astrocytoma), glioma hepatoma, heterohybridoma, heteromyeloma, histiocytoma, hybridoma (e.g., B cell), hypernephroma, insulinoma, islet tumor, keratoma, leiomyoblastoma, leiomyosarcoma, leukemia (e.g., acute lymphatic, acute lymphoblastic, acute lymphoblastic pre-B cell, acute lymphoblastic T cell leukemia, acute—megakaryoblastic, monocytic, acute myelogenous, acute myeloid, B cell, basophilic, chronic myeloid, chronic, B cell, eosinophilic, Friend, granulocytic or myelocytic, hairy cell, lymphocytic, megakaryoblastic, monocytic, monocytic-macrophage, myeloblastic, myeloid, myelomonocytic, plasma cell, pre-B cell, promyelocytic, subacute, T cell, lymphoid neoplasm), lymphosarcoma, melanoma, mammary tumor, mastocytoma, medulloblastoma, mesothelioma, metastatic tumor, monocyte tumor, multiple myeloma, myelodysplastic syndrome, myeloma, nephroblastoma, nervous tissue glial tumor, nervous tissue neuronal tumor, neurinoma, neuroblastoma, oligodendroglioma, osteochondroma, osteomyeloma, osteosarcoma (e.g., Ewing's), papilloma, transitional cell, pheochromocytoma, pituitary tumor, plasmacytoma, retinoblastoma, rhabdomyosarcoma, sarcoma (e.g., Ewing's, histiocytic cell, Jensen, osteogenic, reticulum cell), schwannoma, subcutaneous tumor, teratocarcinoma (e.g., pluripotent), teratoma, testicular tumor, thymoma and trichoepithelioma.

A growing body of evidence indicates that angiogenesis is essential to the progression of cancer. In fact, the extent of neovascularity is strongly correlated with metastases in primary breast carcinoma, bladder cancer, prostrate cancer, non-small cell lung cancer, cutaneous melanomas, and uterine cervix carcinoma [Ferrara, N., Breast Cancer Research and Treatment 36: 127-137 (1995)]. Thus, assessing the angiogenic phenotype of tumors will provide a strong indication to disease outcome. Other diseases or conditions which are characterized by hypervascularization or hypovascularization include, but are not limited to, retinal neovascularization, neovascularization in atherosclerotic plaques, hemangiomas, arthritis, and psoriasis, as well as the diseases described hereinabove. See Folkman, J. New England J. of Med. 333:1757-63 (1995).

Thus, the ability of the peptides of the invention to bind specifically to the cell-surface of endothelial cells, suggests the use thereof as potent detectors of vascularization. This may be important for detecting the presence of, assessing predisposition to, or monitoring progression of angiogenesis-dependent diseases.

Thus, the invention also envisages a method of detecting a presence or an absence of endothelial cells in a biological sample.

The method is effected by incubating the biological sample with the peptide of the invention (which is capable of binding to the cell-surface of endothelial cells, e.g., via the GRP78 receptor) and detecting the peptide, to thereby detect the presence or an absence of endothelial cells in the biological sample.

The biological sample utilized for detection can be a tissue sample such as a biopsy specimen. Methods of obtaining tissue biopsies from mammals are well known in the art (see Hypertext Transfer Protocol://World Wide Web dot healthatoz dot com/healthatoz/Atoz/default dot html).

At least one peptide of the invention is contacted with the biological sample under conditions suitable for complex formation (i.e., buffer, temperature, incubation time etc.) as described in the Examples section which follows.

Peptide-cell complexes within a biological sample can be detected via any one of several methods known in the art, which methods can employ biochemical and/or optical detection schemes.

To facilitate complex detection, the peptides of the invention are highlighted by a tag or an antibody. It will be appreciated that highlighting can be effected prior to, concomitant with or following complex formation, depending on the highlighting method. As used herein the term "tag" refers to a molecule, which exhibits a quantifiable activity or characteristic. A tag can be a fluorescent molecule including chemical fluorescers, such as fluorescein or polypeptide fluorescers, such as the green fluorescent protein (GFP) or related proteins (www dot clontech dot corn). In such case, the tag can be quantified via its fluorescence, which is generated upon the application of a suitable excitatory light. Alternatively, a tag can be an epitope tag, a fairly unique polypeptide sequence to which a specific antibody can bind without substantially cross reacting with other cellular epitopes. Such epitope tags include a Myc tag, a Flag tag, a His tag, a leucine tag, an IgG tag, a streptavidin tag and the like.

It will be appreciated that the peptides of the invention may also be used as potent detectors of endothelial cells in vivo. A designed peptide capable of binding endothelial cells, labeled non-radioactively or with a radio-isotope, as is well known in the art can be administered to an individual to diagnose the onset or presence of angiogenesis-dependent disease, discussed hereinabove. The binding of such a labeled peptide after administration to endothelial cells can be detected by in vivo imaging techniques known in the art.

It will be appreciated that the peptide of the invention can be further used to identify a putative angiogenic molecule (i.e., a molecule capable of inducing angiogenesis) or anti-angiogenic (i.e., a molecule capable of inhibiting angiogenesis). Thus, according to another aspect of the invention there is provided a method of identifying a putative angiogenic molecule. The method is effected by: (a) providing endothelial cells having the peptide of the invention bound thereto, and (b) identifying a molecule capable of displacing the peptide from the endothelial cells, to thereby identify a putative angiogenic or anti-angiogenic molecule.

Alternatively, the method of identifying the putative angiogenic or anti-angiogenic molecule can be effected by: (a) incubating the peptide of the invention with a glucose-regulated protein (GRP78) or cells expressing the GRP78 under conditions suitable for formation of a complex between the peptide and the GRP78 or the cells expressing GRP78, and (b) identifying a molecule capable of displacing the peptide from the complex, to thereby identify a putative angiogenic or anti-angiogenic molecule.

It will be appreciated that such a detection method can also be utilized in an assay for uncovering potential drugs useful in inhibition or promotion (induction) of angiogenesis. For example, the invention may be used for high throughput screening of test compounds (i.e., putative angiogenic or anti-angiogenic molecules). Typically, the peptides of the invention are radiolabeled, to reduce assay volume. The peptides are allowed to bind endothelial cells prior to, concomitant with or following binding of the test compound. A competition assay is then effected by monitoring displacement of the label by a test compound [Han (1996) J. Am. Chem. Soc. 118:4506-7 and Esler (1996) Chem. 271:8545-8].

Once a putative angiogenic or anti-angiogenic molecule is identified it is further evaluated using angiogenesis assays which are well known in the art. Examples include, but are not limited to, the chick chorioallantoic membrane, rabbit cornea assay, sponge implant models, matrigel and tumor models (see also the assays described in the Examples section which follows).

The peptides of the invention can be included in a diagnostic or therapeutic kit. For example, the peptides can be packaged in one or more containers with appropriate buffers and preservatives and used for diagnosis or for directing therapeutic treatment. Thus, the peptides, for example, can be each mixed in a single container or placed in individual containers. According to an embodiment of the invention, the containers include a label. Suitable containers include, for example, bottles, vials, syringes, and test tubes. The containers may be formed from a variety of materials, such as glass or plastic.

In addition, other additives, such as stabilizers, buffers, blockers and the like may also be added.

The peptides of such kits can also be attached to a solid support, such as beads, array substrate (e.g., chips) and the like and used for diagnostic purposes.

Peptides included in kits or immobilized to substrates may be conjugated to a detectable label, such as described hereinabove.

The kit can also include instructions for determining if the tested subject is suffering from, or is at risk of developing, a condition, disorder, or disease associated with disregulated angiogenesis.

As used herein the term "about" refers to ±10%.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Peptide synthesis—ADOPep1 (SEQ ID NO:2), ADOPep2 (SEQ ID NO:3) and ADOPep3 (SEQ ID NO:4) were synthesized by SynPep (Dublin, Calif., USA) according to the ADAM15 amino acid sequence (GenBank Accession No. Q13444). HPLC purity was greater than 97%. The peptides were dissolved in water in a concentration of 1 mg/ml.

Binding of ADOPep to endothelial cells—Human umbilical endothelial cells (HUVEC) were harvested by trypsin and 100,000 cells per sample were suspended in PBS+5% FCS+ 0.1% Na azide. Endothelial cells were either exposed for 5 hours to hypoxia or remained under normoxia conditions. Cells were stained for 2 hours on ice in dark with 0.05, 0.5, 5 µg/100,000 cells biotinylated ADOPeps. The cells were then washed twice with PBS, following which the cells were stained for 30 minutes with FITC-labeled Streptavidin (Jackson ImmunoResearch Laboratories, PA, USA). After washing, samples were analyzed using a fluorescence activated cell sorter (FACScan Beckton Dickinson, CA, USA).

Proliferation of endothelial cells incubated with ADOPeps—HUVEC from passage 3 were used for proliferation experiments. Endothelial cells (15,000 cells/well) were seeded on 24-wells in the presence of endothelial cell growth medium (Promocell, Heidelberg, Germany) with supplements and incubated for 24 hours. After then, cells were exposed to 24 hours starvation in a medium free of supplements. ADOPeps were added at concentrations of 1, 10 and 100 ng/ml for 24 hours under hypoxic conditions. 2 µCi/well of Thymidine (SIGMA, Rehovot Israel) were added or over night incubation followed by 3 washes with PBS before harvesting at 37° C. with 300 µl/well of 0.5 M NaOH. Cell lysates were transferred to scintillation vials with 2 ml scintillation liquid Ultima Gold (Packard Bioscience, Meriden, USA) and counted in a β counter. Results were obtained as counts per minute (cpm).

Migration of endothelial cells induced by ADOPeps—Endothelial cell migration was evaluated by the Chemicon QCM 96-well Migration Assay (Chemicon International, CA, USA) according to manufacturer's instructions. This kit utilizes a membrane with an 8 µm pore size. Migratory cells on the bottom of the insert membrane are dissociated from the membrane when incubated with cell detachment buffer provided by the kit. These cells are subsequently lysed and detected by a molecular probe CyQuant GR dye, a green fluorescent dye which exhibits fluorescent enhancement when bound to cellular nucleic acid. For the migration assay, HUVEC from passage 3 were incubated in endothelial cell (EC) growth medium free of supplements. After trypsinization, 25,000 EC were incubated in the migration chamber. ADOPeps were added at concentrations of 1, 10 and 100 ng/ml in the feeder tray for chemoattractant migration assay. Time of incubation was 5 hours for endothelial cells under hypoxic conditions. Results were determined in a Fluorescent ELISA reader at 480/520 nm.

Mouse hind-limb ischemia model for evaluation of the in vivo angiogenic activity of the ADOPeps—A mouse hind limb ischemia model was used. Ischemia was created in the C57Bl strain mouse by ligation and excision of the femoral artery on the left hind limb. The right hind limb served as a control. A day after the operation ADOPep1 and 3 were injected intramuscular at a site close to the operation. Each mouse was treated one day after operation, with either peptide in a total amount of 0.1 or 1 µg per mouse or PBS (50 µl) which was injected as a control. The blood perfusion was measured using a Laser Doppler Blood perfusion analyzer (Perimed, Sweden) one day post operation and 7, 14, 21 days post operation. The average perfusion of each limb was computed and percent perfusion ratio was expressed as the ischemic (left)/control (right) percent perfusion ratio.

Histological examination—Limbs from mice treated with ADOPep1, 3 or control mice injected with PBS were sacrificed at 7, 14 and 21 days post operation. Whole ischemic and non-ischemic legs were immediately fixed for 48 hours in 4% paraformaldehyde and then embedded in paraffin. Three-micrometer thick sections were prepared and cut with the muscle fibers oriented transversely. Identification of endothelial cells was performed by immunostaining for von Willebrand Factor VIII related antigen using a primary antibody of polyclonal anti-factor VIII at a 1/200 dilution (DakoCytomation, Denmark) and secondary antibody the Envision+ System-HRP (DakoCytomation, Denmark). Vessel densities were expressed as capillaries per millimeter squared. To obtain the average vessel number per cross-section area, a minimum of ten individual fields were sampled, and Image Pro-Plus (MediaCybernetics, Silver spring, MD, USA) was used to measure the counted area. The number of Factor VIII positive vessels was counted.

Immune Precipitation (IP) Experiments of Endothelial Cells with Biotinylated ADOPep Preparation of HUVEC lysates—HUVEC were seeded in 90 mm Petri dishes plates for 24 hours with complete Endothelial Cell Growth Medium (PromoCell. Heildelberg, Germany). Cells were washed twice with PBS and buffer lysate (50 mM Tris Cl (pH 8, 150 mM Na Cl, 0.02% Na azide, 0.1% SDS, 100 µg/ml PMSF, 1 µg/ml protease inhibitors, 1% NP-40) was added for 20 minutes on ice. After incubation, cells were scraped with a rubber policeman and transferred to a chilled microfuge tube. After centrifugation of lysate at 12,000 g for 2 minutes at 4° C., supernatant was transferred to a fresh microfuge tube and stored at −70° C.

Immunoprecipitation (IP)—Aliquots samples of lysates (500 µl) were incubated with 10 µg of biotinylated ADOPep1 for one hour at 4° C. by gently mixing. Streptavidin Sepharose beads (Amersham Biosciences, Uppsla, Sweden) (50 µl) were added to the sample for a second incubation one hour at 4° C. by gently mixing. After then, sample was centrifuge for 20 seconds at 12,000 g and the pellet was saved and further washed 3 times. Finally the pellet was suspended in 100 µl of sample buffer for Western blot analysis. For ELISA, protein was eluted by 5 minutes incubation of the sample at room temperature in 1 ml of Tris-Glycin 0.2 M (pH 2.2), followed by titration with 1 M Tris (pH 9.1).

Polyacrylamide Gel Electrophoresis (PAGE) analysis—The protein band containing GRP78 which was immunoprecipitated with the biotinylated ADOPep1 (GRP78 immune-precipitated protein) (30 µl) was applied to minigel lane and run at standard conditions (60 mA for 2 minigels, 1.4 hours) in a 10% Tris Acrylamide gel. Gel was stained with Coomassie blue. Band was cut and sent to mass-spectroscopy for protein identification.

Western Blot analysis—Following PAGE analysis, proteins transfer was performed for 2 hours in wet conditions at 40 V in a nitrocellulose membrane, following which the gel was stained with Coomassie blue. The nitrocellulose membrane was blocked for 2 hours at room temperature by incubation with PBS containing 0.5% Tween-20 and 5% non-fat milk. Incubation of the membrane with biotinylated ADOPep1 (5 µg/ml in PBS-Tween) was performed over night at 4° C. by gently shaking. After then, membrane was washed 3 times (15 minutes each) in PBS-Tween. Incubation with the secondary antibody Peroxidase-conjugated Streptavidin (1 µg/ml) (JacksonImmunoResearch, PA, CA USA) was performed for 45 minutes at room temperature followed by 3 washes (15 minutes each) in PBS-Tween. For GRP78 immunostaining, the membrane was blocked as described hereinabove and further incubated for 24 hours at 4° C. with anti-GRP78 antibody (Santa Cruz Biotechnologies, CA, USA) at a concentration of 2 micrograms per ml, followed by 3 washes with PBS-Tween. Incubation with a secondary anti-goat FITC (Jackson ImmunoResearch Laboratories, PA, USA) at a dilution of 1:5000 was performed for 45 minutes at room temperature, followed by 3 washes in PBS-Tween. ECL was performed using SuperSignal West Pico Chemiluminescent Substrate (Pierce, Ill., USA).

FACS analysis of anti GRP78 binding to Endothelial Cells—HUVEC were harvested by trypsin and 100,000 cells per sample were suspended in PBS+5% FCS+0.1% Na azide. Goat polyclonal anti GRP78 (Santa Cruz Biotechnologies, CA, USA) at a concentration of 1 µg/100,000 cells was added for 40 minutes on ice. Cells were washed and stained with anti-goat FITC (Jackson ImmunoResearch Laboratories, PA, USA). Samples were analyzed using a fluorescence activated cell sorter (FACScan Beckton Dickinson, CA, USA).

FACS analysis of anti GRP78 binding to different tumor cells—MCF7 breast carcinoma, SK28 Melanoma, HT 29 colon carcinoma and K562 erythroleukemia were harvested by trypsin and 300,000 cells per sample were suspended in PBS+5% FCS+0.1% Na azide. Goat polyclonal anti GRP-78 (Santa Cruz Biotechnologies, CA, USA) at a concentration of 1 µg/100,000 cells was added for 40 minutes on ice. Cells were washed and stained with anti-goat FITC (Jackson ImmunoResearch Laboratories, PA, USA). Samples were analyzed using a fluorescence activated cell sorter (FACScan Beckton Dickinson, CA, USA).

Apoptosis—EC were incubated for 24 hours with 5% FCS in EC growth media in Petri dishes plates followed by 24 hours incubation under hypoxia conditions with ADOPep1 (10 ng/ml), anti GRP78 antibody (Santa Cruz Biotechnology, CA, USA) (1 microgram/ml) or recombinant VEGF (10 ng/ml). The Annexin V FITC/PI detects the phosphatidylserin on the apoptotic cells using flow cytometry. Human Annexin V-FITC kit (Bender Medsystems, Vienna, Austria) was used for the measurement of EC apoptosis percentage following manufacturer's instructions. Samples were analyzed using a fluorescence activated cell sorter (FACScan Beckton Dickinson, CA, USA).

Competitive binding of ADOPep1, ADOPep2 and ADOPep3 peptides to GRP78—Endothelial cells (20,000 per well) were seeded in 96 well plates for 24 hours in the presence of the complete medium. Plates were washed with PBS over night and rehydrated with PBS, 0.1% Na Azide and 5% FCS. ADOPep1, ADOPep2 and ADOPep3 were added to washed plates for 2 hours at room temperature at concentrations of 0.01, 0.1 and 1 microgram per ml. Anti-GRP78 antibody (goat polyclona IgG, Santa Cruz Biotechnology, CA, USA) was added to the plates for 1 hour at room temperature at a concentration of 2 micrograms/ml per well. After washing, bound anti-GRP78 antibody was detected by incubation with anti-goat IgG Peroxidase conjugated (Jackson Immuneresearch Laboratories, PA, USA). After 5 washes with PBS-0.1% Tween 20, 100 µl/well of TMB+ Substrate-Chromogen (DAKOCytomation, CA, USA) was added for a maximum of 30 minutes. Reaction was stopped with 1 N HCl. Color developed was determined by an ELISA reader at 450 nm.

Example 1

Specific Peptides Derived from the Metalloprotease Domain of ADAM15 Bind to Endothelial Cell and Induce Proliferation and Migration Thereof Experimental Results ADOPep1 Sequence—Several peptides were synthesized from the metalloprotease domain and preliminary experiments were conducted in order to select a peptide with the best binding ability to endothelial cells. One of these, a peptide termed ADOPep1, has the amino acid sequence set forth by SEQ ID NO:2, HWRRAHLLPRLP. Its location in the metalloprotease domain of ADAM15 molecule (SEQ ID NO:1) is presented in FIG. 2b (underlined text corresponding to amino acids 286-297 of SEQ ID NO:1).

Binding of ADOPep1 to endothelial cells (EC) by FACS analysis—Increasing concentrations of biotinylated ADOPep1 were added to EC under normoxia conditions and the binding of ADOPep1 to EC was detected using FITC-labeled Streptavidin and FACS analysis. As can be seen in FIG. 3 an increase in percent binding of ADOPep1 to EC reached about 62% in a dose dependent manner and was maximal at 5 micrograms per ml. When EC under hypoxia conditions (for 5 hours) were incubated with biotinylated ADOPep1, the binding of the ADOPep1 at 5 µg/ml reached about 85% (FIG. 4). These results demonstrate an increase in binding of ADOPep1 to endothelial cells under hypoxia.

ADOPeps induce proliferation of EC under hypoxia—To further test the ability of ADOPeps to induce EC proliferation, increasing concentrations of ADOPeps 1, 2 and 3 were incubated with EC and the proliferation of cells under hypoxia and 24 hours starvation was determined. As shown in FIG. 5, ADOPep1 and ADOPep2 were capable of inducing proliferation of EC at a concentration of 10 ng/ml.

Novel peptide ADOPep1 induces migration of EC under hypoxia—The ability of ADOPeps to induce migration of endothelial cells under hypoxia was tested. EC were incubated in the migration chamber and ADOPeps were added at 1, 10 and 100 ng/ml in the feeder tray for 5 hours under hypoxia conditions. The migration of EC was determined in a Fluorescent ELISA reader and is expressed as Relative Fluorescent Units (RFU). As shown in FIG. 6, the most significant increase in EC migration was observed in the presence of ADOPep1 at a concentration of 10 ng/ml.

Altogether, these findings demonstrate that the ADOPeps of the invention are capable of binding to endothelial cell, mainly under hypoxia and inducing proliferation and migration of endothelial cells under hypoxia.

Example 2

ADOPep1 Induces Angiogenesis and Increased Perfusion of Ischemic Tissues In Vivo Experimental Results ADOPep1 induces a significant increase in perfusion in mice with hind limb ischemia—A mouse ischemic hind limb model was used for evaluation of the in vivo potential of angiogenesis induced by ADOPeps. Ischemia was created in the mouse left hind limb by ligation and excision of the femoral artery. The right hind limb served as control. A day after the operation each of the peptides was injected into one site close to the ligation. Each mouse was treated with each of the peptides in a total amount of 0.1 or 1 µg per mouse. The blood perfusion was measured using a Laser Doppler Imager (PeriMed, Sweden) at days 7, 14 and 21 after operation. As can be seen in FIG. 7 the average perfusion of each limb was computed and expressed as the ischemic (left)/control (right) blood perfusion ratio. A statistical analysis demonstrates a significant increase in the blood perfusion ratio in mice injected with 0.1 microgram ADOPep1 at day 21 after operation in comparison to mice injected with PBS demonstrating complete recovery of the blood perfusion in the hind limb.

Histological assessment of angiogenesis in the ischemic hind limb treated with ADOPep1—After hind limb ligation and administration of 0.1 µg/per mouse of ADOPep1, the mice were sacrificed at days 7, 14 and 21 and the whole legs were embedded in paraffin. FIG. 8 shows the average of vessel number per cross section area of ten individual fields per sample expressed as mean±SE in legs of mice treated with ADOPep1 in comparison to PBS injected mice. ADOPep1 treatment resulted in a significant increase (p<0.05) in the number of blood vessels in comparison to PBS treated mice. Representative illustrations (FIGS. 9a-b) show higher von Willebrand Factor Positive stained small vessels in the ADOPep1 treated group than in the control.

Altogether, these findings demonstrate that the ADOPeps of the invention are capable of inducing angiogenesis following ischemia and thus can be used to treat ischemic diseases.

Example 3

Identification of the ADOPeps Receptor on Endothelial Cells

Experimental Results

Identification of the ADOPep receptor on endothelial cells—Immune precipitation (IP) of endothelial cells lysate with biotinylated ADOPep1 was analyzed by PAGE. As can be seen in FIGS. 10a-b, following immunoprecipitation with ADOPep1 a major single protein band is present at 78 kDa. In order to confirm that this band is the ADOPep1 peptide binding receptor, the separated proteins were transferred to a nitrocellulose membrane which was further stained with biotinylated ADOPep1 followed by Chemiluminescent Substrate. As can be seen in FIG. 11, indeed the same band was stained by the labeled peptide in two different experiments (both lanes in the PAGE shown in FIG. 11). The protein receptor band was cut from the gel and analyzed by mass-spectrometry.

The results of mass-spectrometry are presented in Table 4, hereinbelow. The receptor was identified as the glucose-regulated protein [*Homo sapiens*] GRP78 protein (GenBank Accession No. CAB71335; Gi: 6900104) with 22 peptides digested from the isolated band.

TABLE 4

IP with ADOPep1 in Normoxia

|    | Score | Mass | IP with ADOPep 1 in Normoxia Sequence | SEQ ID NO: |
|----|-------|------|---------------------------------------|------------|
| 1  | 88    | 1528.7 | AKFEELNM(+16)DLFR | 12 |
| 2  | 96    | 1588.8 | KSDIDEIVLVGGSTR | 13 |
| 3  | 96    | 1191.6 | VYEGERPLTK | 14 |
| 4  | 96 88 | 1217.6 | DAGTIAGLNVMR | 15 |
| 5  | 92 92 | 1228.6 | VEIIANDQGNR | 16 |
| 6  | 95 86 | 1233.6 | DAGTIAGLNVM(+16)R | 17 |
| 7  | 87    | 1256.6 | M(+16)KETAEAYLGK | 18 |
| 8  | 95    | 1888 | VTHAVVTVPAYFNDAQR | 19 |
| 9  | 79    | 1934 | DNHLLGTFDLTGIPPAPR | 20 |
| 10 | 97    | 1313.6 | FEELNMDLFR | 21 |
| 11 | 99    | 1316.6 | NELESYAYSLK | 22 |
| 12 | 92 83 | 1329.6 | FEELNM(+16)DLFR | 23 |
| 13 | 95    | 1397.8 | ELEEIVQPIISK | 24 |
| 14 | 99    | 1430.7 | TWNDPSVQQDIK | 25 |
| 15 | 96 86 | 1460.7 | SDIDEIVLVGGSTR | 26 |
| 16 | 86 84 | 758.4 | NTVVPTK | 27 |
| 17 | 81    | 1528.7 | AKFEELNM(+16)DLFR | 28 |
| 18 | 95    | 1552.8 | TFAPEEISAM(+16)VLTK | 29 |
| 19 | 96    | 1566.8 | ITPSYVAFTPEGER | 30 |
| 20 | 96    | 1604.8 | TKPYIQVDIGGGQTK | 31 |
| 21 | 93    | 1659.9 | IINEPTAAAIAYGLDK | 32 |
| 22 | 97    | 1677.8 | NQLTSNPENTVFDAK | 33 |
| 23 | 99    | 1836.9 | SQIFSTASDNQPTVTIK | 34 |
| 24 | 89    | 1888 | VTHAVVTVPAYFNDAQR | 35 |
| 25 | 91    | 1934 | DNHLLGTFDLTGIPPAPR | 36 |
| 26 | 97    | 2165 | IEIESFYEGEDFSETLTR | 37 |
| 27 | 99    | 2176 | LYGSAGPPPTGEEDTAEKDEL | 38 |

To further confirm that indeed the ADOPep1 receptor on endothelial cells is the GRP78 protein, the IP experiment was repeated and Western blot analysis was performed using an anti GRP78 antibody. Results presented in FIG. 12 demonstrate the positive staining with anti-GRP78.

Identification of GRP78 Receptor protein on EC under hypoxia—In order to analyze the receptor on EC that binds the ADOPep peptides under hypoxia conditions, EC were pre incubated for 5 hours under hypoxia conditions and immune precipitation was performed with Biotinylated ADOPep1, followed by Western blot analyses using biotinylated ADOPep1 (FIG. 13a) or anti-GRP78 antibody (FIG. 13b). Confirmation of an identical receptor on EC (glucose-regulated protein, *homo sapiens*, Gi 6900104) under hypoxia was done by mass spectroscopy (19 identities) as presented in Table 5, hereinbelow.

TABLE 5

IP with ADOPep1 at Hypoxia

|    | > Score > | Mass | IP with ADOPep1 at Hypoxia Sequence | SEQ ID NO: |
|----|-----------|------|-------------------------------------|------------|
| 1  | 96        | 1588.8 | KSDIDEIVLVGGSTR | 39 |
| 2  | 96        | 1191.6 | VYEGERPLTK | 40 |
| 3  | 96 88     | 1217.6 | DAGTIAGLNVMR | 41 |
| 4  | 92 92     | 1228.6 | VEIIANDQGNR | 42 |
| 5  | 95 86     | 1233.6 | DAGTIAGLNVM(+16)R | 43 |
| 6  | 95        | 1888 | VTHAVVTVPAYFNDAQR | 44 |
| 7  | 79        | 1934 | DNHLLGTFDLTGIPPAPR | 45 |
| 8  | 97        | 1313.6 | FEELNMDLFR | 46 |
| 9  | 99        | 1316.6 | NELESYAYSLK | 47 |
| 10 | 94        | 1974.9 | IEWLESHQDADIEDFK | 48 |
| 11 | 92 83     | 1329.6 | FEELNM(+16)DLFR | 49 |
| 12 | 95        | 1397.8 | ELEEIVQPIISK | 50 |
| 13 | 99        | 1430.7 | TWNDPSVQQDIK | 51 |
| 14 | 96 86     | 1460.7 | SDIDEIVLVGGSTR | 52 |
| 15 | 95        | 1552.8 | TFAPEEISAM(+16)VLTK | 53 |
| 16 | 96        | 1566.8 | ITPSYVAFTPEGER | 54 |
| 17 | 90        | 1588.8 | KSDIDEIVLVGGSTR | 55 |
| 18 | 93        | 1659.9 | IINEPTAAAIAYGLDK | 56 |
| 19 | 97        | 1677.8 | NQLTSNPENTVFDAK | 57 |
| 20 | 99        | 1836.9 | SQIFSTASDNQPTVTIK | 58 |
| 21 | 97        | 2165 | IEIESFYEGEDFSETLTR | 59 |
| 22 | 99        | 2176 | LYGSAGPPPTGEEDTAEKDEL | 60 |

Increased presentation of GRP78 protein on EC under hypoxia—FIGS. 14 and 15 demonstrate by FACS analysis the percentage of EC expressing GRP78 on their membrane under normoxia and hypoxia conditions. As can be seen in FIG. 14, the binding of anti-GRP78 to EC, originating from 10 different umbilical cords, was 30±13% under normoxia conditions and 52.8±8.4% after 5 hours of hypoxia. FACS histogram (FIG. 15) demonstrated presence of GRP78 receptor on ECs under normoxia or hypoxia conditions, with increased binding of anti-GRP78 antibody under hypoxia.

Receptor presence on tumor cells—To further confirm the presence of GRP78 on EC and its relationship to hypoxia, FACS analyses using the anti-GRP78 antibody performed on different lines of tumor cells including the MCF7 breast carcinoma, SK melanoma, HT colon carcinoma and K562 erythroleukemia tumor cells revealed that GRP78 is expressed on MCF7 breast carcinoma, HT-29 colon carcinoma and SK-28 melanoma cell lines but not on K562 erythroleukemia cells (FIGS. 16a-d).

These results demonstrate that the ADOPeps receptor on EC is GRP78 and that its presentation on EC membrane is increased under hypoxia and in various tumor cells.

Example 4

ADOPeps Inhibit Hypoxia-Induced Apoptosis

Experimental Results

Inhibition of the GRP78 receptor with an anti-GRP78 antibody or the addition of ADOPep1 result in inhibition of hypoxia-induced apoptosis of EC—The role of GRP78 in apoptosis was studied using EC under hypoxia. As shown in FIG. 17, the percentage of apoptosis of EC that were exposed for 24 hours to hypoxia was increased from 25% to 62%. Incubation of EC with ADOPep1 prevented apoptosis to levels which are similar to those seen under normoxic conditions. Incubation of EC with anti-GRP78 antibody also decreased the levels of apoptosis, however, the ADOPep was more efficient (in 29%) in decreasing apoptosis as compared to the anti-GRP78 antibody (FIG. 17). FIGS. 18a-e depict illustration by dot plot FACS analysis of the inhibition of apoptosis by the ADOPep1 peptide. As can be seen, EC under hypoxia were stained with both Annexin V and Propidium Iodide (PI) apoptotic markers. In contrast, incubation of EC with the ADOPep1 peptide induced a remarkable decrease in the percentage of stained cells.

ADOPep1 inhibited hypoxia-induced, but not $CoCl_2$-induced apoptosis—To further substantiate the effect of ADOPep1 on apoptosis, apoptosis was induced by hypoxia or $CoCl_2$ (Cobalt-Chloride) treatment. As is shown in FIGS. 33a-f and 34, 24 hours of hypoxia resulted in an increase of apoptosis to about 70%. In addition, while AdoPep1 inhibited hypoxia-induced apoptosis of endothelial cells in approximately 40 percent, AdoPep1 did not inhibit apoptosis of endothelial cells exposed to the apoptotic inducer Cobalt-Chloride. Thus, the inhibition of apoptosis by ADOPep1 is specific to the hypoxia stress conditions.

ADOPep1 induces inhibition of hypoxia-induced apoptosis in vivo—As can be seen in FIG. 22, the mean number of apoptotic cells is dramatically decreased in 7-day ischemic hind limb that was injected with ADoPep1. Thus, using the ischemic hind limb mouse model the present inventors were able to show, for the first time, that administration of ADOPep1 to ischemic hind limb results in a significant reduction of ischemia-induced apoptosis.

Altogether, these results demonstrate that similarly to GRP78, a stress-responsive protein, the ADOPeps of the invention are capable of decreasing the number of hypoxia-induced apoptotic endothelial cells, and therefore can be used to inhibit apoptosis in cells.

Example 5

ADOPeps Bind to the GRP78 Receptor on Endothelial Cells

Experimental Results

Competitive binding of ADAM15 derived peptides ADOPep1, ADOPep2 and ADOPep3 to GRP78 receptor—To further test if the ADOPeps bind to the GRP78 receptor on EC, a competitive binding assay was performed on EC which were incubated with the ADOPeps prior to binding with the anti-GRP78 antibody. As demonstrated in FIG. 19 (which represents a summary of 4 experiments), all 3 ADOPeps (i.e., ADOPep1, ADOPep2 and ADOPep3) show some degree of inhibition of binding of anti-GRP78 antibody to EC while scrambled peptide (sRoY) was not effective in the competitive binding to the receptor on EC.

ADOPep1 induces upregulation of GRP78 receptor expression in vitro (under hypoxia)—FIGS. 20a-b further depict the binding of the anti-GRP78 antibody to endothelial cells following incubation of the cells with ADOPep1 under normoxia or hypoxia conditions and demonstrate that while the presence of the GRP78 receptor on endothelial cell (as evidenced by the binding of anti-GRP78 to EC) increases under hypoxia from about 18.1% to about 40.1% (as was previously reported by others Li J, Lee A S. Stress induction of GRP/BIP and its role in cancer. Curr. Mol. Med. 2006; 6:45-54; Arap M A, Landenranta J, Mintz P J, Hajitou A, Sarkis A S, Arap W, Pasqualini R. Cell surface expression of the stress response chaperone GRP78 enables tumor targeting by circulating ligands. Cancer Cell. 2004; 6:275-84), a more significant increase in GRP78 presentation on the EC (of up to about 83.8%) is observed when the cells are incubated with the ADOPep1 under hypoxia conditions. These results demonstrate the involvement of ADOPep1 in the upregulation of GRP78 under hypoxia.

ADOPep1 induces upregulation of GRP78 receptor expression in vivo (under ischemia)—To further confirm the ADOPeps involvement in GRP78 presentation on endothelial cells, the mean number of GRP78 positive cells was determined in ischemic limb sections. As is shown in FIG. 21, 7 days following induction of ischemia the mean number of GRP78 positive cells was increased as compared to untreated hind limbs. However, injection of Adopep1 resulted in a more significant increase in mean number of GRP78 positive cells as detected 14 days after induction of ischemia. The relatively low level of GRP78 positive cells at 21 days after ischemia probably represents recovery of the ischemia in the treated animas.

These results demonstrate that ADOPep1 increases GRP78 expression under hypoxia (in vitro) or ischemia (in vivo).

Example 6

ADOPep1 Binding Causes a GRP78 Receptor Internalization Response Under Hypoxic Conditions Experimental Results ADOPep1 binding causes a GRP78 receptor internalization response under hypoxic conditions—As is shown in FIG. 29, after 5 minutes of incubation, AdoPep1 induced GRP78 receptor internalization in endothelial cells under hypoxic conditions. The internalization response was demonstrated by inhibition of percent binding of AdoPep to membranes (less membrane GRP78 receptors) and increase in intracellular GRP78 mean fluorescence in the endothelial cells incubated for 5 minutes with AdoPep1.

Example 7

Identification of Minimal Motif Sequences from the ADOPep Peptides which Exhibit a Biological Activity Experimental Results Identification of novel angiogenesis or tumor related motif—The present inventors have identified a 4 amino-acid sequence, HWRR, as a common motif present on ADOPep1, 2 and 3 ADAM15 derived peptides, that induces angiogenesis and binds to the GRP78 receptor on EC (Table 6, hereinbelow).

TABLE 6

Amino acid sequences of the ADOPeptides of the invention

| Peptide number | Name | Sequence | SEQ ID NO: |
|---|---|---|---|
| 1 | ADOPep1 | H W R R A H L L P R L P | 2 |
| 2 | ADOPep2 | E N F L H W R R A H L L | 3 |
| 3 | ADOPep3 | A V T L E N F L H W R R | 4 |

Table 6: The bolded text in each peptide amino acid sequence corresponds to the common 4-amino acid motif HWRR (SEQ ID NO: 5).

The common motif HWRR (SEQ ID NO:5) of all ADOPeps was tested for its angiogenic activity.

To further test if the 5 amino acid motifs HWRRP (motif A; SEQ ID NO:7), HWRRA (motif B; SEQ ID NO:8) or AHLLP (motif C; SEQ ID NO:6) can bind to the GRP78 on EC, synthetic peptide having amino acid sequences corresponding to SEQ ID NOs:7, 8 and 9 were used in a competitive assay for the binding of biotinylated ADOPep1 to endothelial cells. As shown in FIG. 23, while the peptides having amino acid sequence corresponding to Motif A and B exhibited a significant inhibition of the binding of ADOPep1$^{Biot}$ to endothelial cells, the peptide corresponding to Motif C exhibited a moderate inhibition of binding.

In addition, endothelial cells were incubated under hypoxia conditions in the absence or presence of ADOPep1, Motif A or C and the Q1 level of apoptosis was determined using FACS analysis. As shown in FIGS. 24a-d and 25 while ADOPep1 and Motif A and B peptides were capable of inhibiting the hypoxia induced apoptosis, the motif C peptide exhibited no effect on hypoxia induced apoptosis.

To further test the biological activity of motifs A, B, C on endothelial cells, a migration assay was performed on EC under hypoxia. As shown in FIGS. 26a-b, while the ADOPep1, Motif A and B peptides induced endothelial cell migration at a concentration of about 10 ng/ml, motif C peptide exhibited no significant effect on endothelial cell migration.

Altogether, these results demonstrate the identification of minimal amino acid sequences from the ADOPeps which are capable of decreasing hypoxia induced apoptosis and inducing endothelial cell migration. These peptides (e.g., SEQ ID NOs:7 and 8) can be used to inhibit hypoxia induced apoptosis, induce angiogenesis and treat ischemic diseases.

Example 8

The ADOPeps Motifs are Capable of Tube Formation and Induction of ERK1/2 Phosphorylation Experimental Results ADOPep1 and motif A peptides are capable of forming tubes from endothelial cells—The ability of ADOPep1 or motif A peptides to form tubes was determined in vitro. As shown in FIG. 27, while the ADOPep1 and Motif A significantly increased the length of the network of connected cells in endothelial cells under starvation and normoxic conditions, the addition of the scrambled sROY peptide had no effect on tube formation.

AdoPep1 and Motif A peptides compete on the binding to the same receptor on endothelial cells—As shown in FIGS. 28a-d, AdoPep1 and Motif A peptides inhibited anti GRP78 binding to endothelial cells under hypoxic conditions. Ten micrograms of AdoPep1 and Motif A inhibited anti GRP78 binding in approximately 80% and 60% respectively, while motif C did not inhibit anti GRP78 binding to endothelial cells.

Incubation of endothelial cells with ADOPep1 and Motif A under hypoxia conditions increase ERK1/2 phosphorylation—As is shown in FIGS. 30a-b, incubation of endothelial cells with ADOPep1 and Motif A under hypoxia conditions resulted in a significant increase in ERK1/2 phosphorylation as measured after 20 minutes.

Induction of ERK1/2 phosphorylation by ADOPep1 and motif A peptides is specific—In order to assess that ERK phosphorylation is specific to AdoPep1 and Motif A activation, a specific pERK peptide inhibitor was added to the endothelial cells incubated with AdoPep1 and Motif A peptides. FIG. 31 shows Western blot analysis of ERK phosphorylation inhibition by the inhibitor peptide in endothelial cells incubated with AdoPep1 and Motif A for 20 minutes under hypoxic conditions.

ADOPep1 and ADOPep2, but not ADOPep3 are capable of inducing ERK1/2 phosphorylation in endothelial cells under hypoxia—As shown in FIGS. 32a-b, Western Blot analyses performed using anti Phospho ERK antibody (Santa Cruz Biotechnologies p-ERK(E-4),sc7383) revealed that while ADOPep1 and 2 induced ERK1/2 phosphorylation, ADOPep3 had not effect on ERK1/2 phosphorylation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the invention.

REFERENCES

Additional References are Cited in Text

1. Trochon V., Li H., Vasse M., Frankenne F., Thomaidis A., Soria J., Lu. H., Gardner C. and Soria C. Endothelial metalloprototease-disintegrin protein (ADAM) is implicated in angiogenesis in vitro. Angiogenesis 2: 277-285, 1998;
2. PCT Pub. WO2005/039616 to the present inventors
3. Koomaqi R., et al., 1999; Anticancer Res. 19(5B): 4333-6;
4. Dong D., et al., 2005, Cancer Res. 65(13): 5785-91;
5. Koshikawa N., et al., 2006, Oncogene 25(6):917-28;
6. Davidson D J., et al., 2005, Cancer Res. 65(11): 4663-72;

What is claimed is:

1. An isolated peptide consisting of the amino acid sequence HWRRP set forth in SEQ ID NO:7 or HWRRA set forth in SEQ ID NO:8.

2. An isolated peptide comprising an amino acid sequence HWRRP as set forth by SEQ ID NO:7 or HWRRA as set forth in SEQ ID NO:8, wherein the peptide consists of 12 or less amino acids.

3. The isolated peptide of claim 2, wherein said amino acid sequence is set forth by SEQ ID NO:2 or 3.

4. The isolated peptide of claim 2, wherein the peptide is a linear peptide.

5. The isolated peptide of claim 2, wherein the peptide is a cyclic peptide.

6. The isolated peptide of claim 2, wherein the peptide consists of 12 or less amino acids.

7. A composition-of-matter comprising at least one peptide of claim 2.

8. A pharmaceutical composition comprising as an active ingredient at least one peptide of claim 2 and a pharmaceutically acceptable carrier or diluent.

9. A method of inducing angiogenesis in a subject, the method comprising administering to the subject a therapeutically effective amount of at least one peptide of claim 2, to thereby induce angiogenesis in the subject.

10. A method of treating a pathology characterized by insufficient angiogenesis in a subject, the method comprising administering to the subject a therapeutically effective amount of at least one peptide of claim 2, to thereby treat the pathology characterized by insufficient angiogenesis in the subject.

11. The method of claim 10, wherein the pathology characterized by insufficient angiogenesis in the subject is selected from the group consisting of delayed wound-healing, delayed ulcer healing, reproduction associated disorder, arteriosclerosis, ischemic vascular disease, ischemic heart disease, myocardial ischemia, myocardial infarction, heart failure, myocardial dysfunction, myocardial remodeling, cardiomyopathies, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, critical leg ischemia, lower extremity ischemia, cerebral ischemia, cerebro vascular disease, retinopathy, retinal repair, remodeling disorder, von Hippel-Lindau syndrome, diabetes, hereditary hemorrhagic telengiectasia, ischemic vascular disease, Buerger's disease and ischemia associated with neurodegenerative disease such as Parkinson's and Alzheimer's disease.

12. The isolated peptide of claim 2, wherein said peptide binds a glucose-regulated protein (GRP78) as set forth by SEQ ID NO:9 on endothelial cells of the tissue.

13. A composition comprising an agent attached to the peptide of claim 2, wherein the peptide targets said agent to endothelial cells.

14. The composition of claim 13, wherein the agent is selected from the group consisting of a toxin, a chemotherapeutic agent and a radioisotope.

15. A pharmaceutical composition comprising as an active ingredient the composition of claim 13 and a pharmaceutically acceptable carrier or diluent.

16. A method of identifying a putative angiogenic molecule, the method comprising:
   (a) incubating the peptide of claim 2 with a glucose-regulated protein (GRP78) or cells expressing said GRP78 under conditions suitable for formation of a complex between the peptide and said GRP78 or said cells expressing GRP78, and
   (b) identifying a molecule capable of displacing the peptide from said complex, to thereby identify a putative angiogenic molecule.

17. A pharmaceutical composition comprising as an active ingredient at least one peptide of claim 1 and a pharmaceutically acceptable carrier or diluent.

18. A method of inducing angiogenesis in a subject, the method comprising administering to the subject a therapeutically effective amount of at least one peptide of claim 1 to thereby induce angiogenesis in the subject.

19. A pharmaceutical composition comprising as an active ingredient at least one peptide of claim 3 and a pharmaceutically acceptable carrier or diluent.

20. A method of inducing angiogenesis in a subject, the method comprising administering to the subject a therapeutically effective amount of at least one peptide of claim 3 to thereby induce angiogenesis in the subject.

21. A composition comprising an agent attached to the peptide of claim 1, wherein the peptide targets said agent to endothelial cells.

22. An isolated peptide consisting of the amino acid sequence set forth in SEQ ID NO:4.

23. A pharmaceutical composition comprising as an active ingredient the peptide of claim 22 and a pharmaceutically acceptable carrier or diluent.

24. A method of inducing angiogenesis in a subject, the method comprising administering to the subject a therapeutically effective amount of the peptide of claim 22, to thereby induce angiogenesis in the subject.

* * * * *